United States Patent
Arnold et al.

(10) Patent No.: US 7,524,664 B2
(45) Date of Patent: Apr. 28, 2009

(54) REGIO- AND ENANTIOSELECTIVE ALKANE HYDROXYLATION WITH MODIFIED CYTOCHROME P450

(75) Inventors: Frances H. Arnold, La Cañada, CA (US); Matthew W. Peters, Pasadena, CA (US); Peter Meinhold, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 319 days.

(21) Appl. No.: 10/869,825

(22) Filed: Jun. 15, 2004

(65) Prior Publication Data

US 2005/0059128 A1    Mar. 17, 2005

Related U.S. Application Data

(60) Provisional application No. 60/479,126, filed on Jun. 17, 2003.

(51) Int. Cl.
- C12N 9/02 (2006.01)
- C12N 15/00 (2006.01)
- C12N 1/20 (2006.01)
- C12P 7/00 (2006.01)
- C12P 21/04 (2006.01)
- C07H 21/04 (2006.01)
- C12Q 1/68 (2006.01)
- C12Q 1/00 (2006.01)
- C12Q 1/26 (2006.01)

(52) U.S. Cl. ............... 435/189; 435/4; 435/6; 435/69.1; 435/71.1; 435/25; 435/132; 435/440; 435/252.3; 435/320.1; 536/23.2

(58) Field of Classification Search ............... None
See application file for complete search history.

(56) References Cited

U.S. PATENT DOCUMENTS

| | | |
|---|---|---|
| 4,599,342 A | 7/1986 | LaHann |
| 5,605,793 A | 2/1997 | Stemmer |
| 5,741,691 A | 4/1998 | Arnold et al. |
| 5,785,989 A | 7/1998 | Stanley et al. |
| 5,811,238 A | 9/1998 | Stemmer et al. |
| 5,830,721 A | 11/1998 | Stemmer et al. |
| 5,837,458 A | 11/1998 | Minshull et al. |
| 5,906,930 A | 5/1999 | Arnold et al. |
| 5,945,325 A | 8/1999 | Arnold et al. |
| 5,965,408 A | 10/1999 | Short |
| 6,090,604 A | 7/2000 | Golightly et al. |
| 6,361,988 B1 | 3/2002 | Arnold et al. |
| 6,498,026 B2 | 12/2002 | Delagrave et al. |
| 6,524,837 B1 | 2/2003 | Arnold et al. |
| 6,537,746 B2 | 3/2003 | Arnold et al. |
| 6,643,591 B1 | 11/2003 | Korzekwa et al. |
| 2003/0077795 A1 | 4/2003 | Wilson et al. |
| 2003/0077796 A1 | 4/2003 | Croteau et al. |
| 2003/0100744 A1 | 5/2003 | Farinas et al. |
| 2005/0037411 A1 | 2/2005 | Arnold et al. |
| 2005/0202419 A1 | 9/2005 | Cirino et al. |

FOREIGN PATENT DOCUMENTS

| | | |
|---|---|---|
| EP | 0 505 198 A1 | 9/1992 |
| EP | 0 752 008 | 2/1997 |
| EP | 0 932 670 | 8/2000 |
| WO | WO 89/03424 A1 | 4/1989 |
| WO | WO 95/22625 | 8/1995 |
| WO | WO 97/16553 A1 | 5/1997 |
| WO | WO 97/20078 | 6/1997 |
| WO | WO 97/35957 A1 | 10/1997 |
| WO | WO 97/35966 A1 | 10/1997 |
| WO | WO 98/27230 | 6/1998 |
| WO | WO 98/31837 A1 | 7/1998 |
| WO | WO 98/41653 A1 | 9/1998 |
| WO | WO 98/42832 | 10/1998 |
| WO | WO 99/60096 A2 | 11/1999 |
| WO | WO 00/00632 A1 | 1/2000 |
| WO | WO 00/04190 A1 | 1/2000 |
| WO | WO 00/06718 A2 | 2/2000 |
| WO | WO 00/09679 A1 | 2/2000 |

(Continued)

OTHER PUBLICATIONS

Branden et al. Introduction to Protein Structure, Garland Publishing Inc., New York, p. 247, 1991.*

(Continued)

*Primary Examiner*—Yong D Pak
(74) *Attorney, Agent, or Firm*—Gavrilovich, Dodd & Lindsey LLP; Joseph R. Baker, Jr.

(57) ABSTRACT

Cytochrome P450 BM-3 from *Bacillus megaterium* was engineered using a combination of directed evolution and site-directed mutagenesis to hydroxylate linear alkanes regio- and enantioselectively using atmospheric dioxygen as an oxidant. Mutant 9-10A-A328V hydroxylates octane primarily at the 2-positio to form S-2-octanol (40% ee). Another mutant, 1-12G, hydroxylates alkanes larger than hexane primarily at the 2-position, but forms R-2-alcohols (40-55% ee). These biocatalysts are highly active for alkane substrates and support thousands of product turnovers. These regio- and enantio-selectivities are retained in whole-cell biotransformations with *E. coli*, where the engineered P450s can be expressed at high levels and the expensive cofactor is supplied endogenously.

26 Claims, 11 Drawing Sheets

FOREIGN PATENT DOCUMENTS

| WO | WO 00/18906 A3 | 4/2000 |
|---|---|---|
| WO | WO 00/31273 A2 | 6/2000 |
| WO | WO 01/62938 A2 | 8/2001 |
| WO | WO 03/008562 A2 | 1/2003 |
| WO | WO 03/008563 | 1/2007 |

OTHER PUBLICATIONS

Affholter et al. "Engineering a Revolution." *Chembytes e-zine* Apr. 1999 [Website] 10 pages, printed Apr. 14, 2004. http://www.chemsoc.org/chembytes/ezine/1999/arnold_arp99.htm.

Cirino & Arnold. "Protein engineering of oxygenases for biocatalysis." *Current Opinion in Chemical Biology*, 2002: 6:130-135.

Cirino & Arnold. "Regioselectivity and Activity of Cytochrome P450 BM-3 and Mutant F87A in Reactions Driven by Hydrogen Peroxide" *Adv. Synth Catal.* 2002: 344, No. 9, 932-937.

Glieder et al. "Laboratory evolution of a soluble, self-sufficient, highly active alkane hydroxylase." *Nature Biotechnology*, Nov. 2002, vol. 20, 1-5.

Grogan, Gideon J. "Biocatalytic Oxidation—An Overview." University of York. Powerpoint presentation. Undated. 6 pages.

Mayhew et al. "Benzocycloarene hydroxylation by P450 biocatalysis." *New J. Chem.*, 2002: 26, 35-42.

Murataliev et al. "Chimmeragenesis of the Fatty acid Binding Site of Cytochrome P450BM3. Replacement of Residues 73-84 with the Homologous Residues from the Insect Cytochrome P450 CYP4C7." *Biochemistry*, 2004: vol. 43, No. 7, 1771-1780.

"Superfamily name: Cytochrome P450." From the Cytochrome P450 Webpage, printed Apr. 5, 2004 http://dmelson.utmem.edu/PIR.P450.description.html 2 pages.

Beratan, et al., "The protein bridge between redox centres", The Protein Electron Transfer, 1996, pp. 23-42.

Govindaraj, et al., "Role of the linker region connecting the reductase and heme domains in cytochrome P450BM-3", Biochemistry, 1995, vol. 34, No. 35, pp. 11221-11226.

Lewis, et al., "Molecular modelling of CYP1 family enzymes CYP1A1, CYP1A2, CYP1A6 and CYP1B1 based on sequence homology with CYP102", Toxicology, 139, 1999, pp. 530-579.

Li, H. et al., "The structure of the cytochrome p450BM-3 haem domain complexed with the fatty acid substrate, palmitoleic acid," *Nature Structural Biology*, Feb. 1997, pp. 140-146, vol. 4, No. 2.

Li, et al. "Characterization of Recombinant Bacillus megaterium Cytochrome P-450BM-3 and ITs Two Functional Domains", The Journal of Biological Chemistry, vol. 266, No. 18, pp. 11909-11914.

Li, et al., "Critical Role of the Residue Size at Position 87 in H2O2-Dependent Substrate Hydroxylation Activity and H2O2 Inactivation of Cytochrome P450BM-3", Ideal, www.idealibrary.com, 2001, vol. 280, No. 5, pp. 1258-1261.

Lipman, et al., "Rapid and Sensitive Protein Similarity Searches", Science, vol. 227, 1985, pp. 1435-1441.

Matsunaga et al., "Fatty Acid-Specific, Regiospecific, and Stereospecific Hydroxylation by Cyctochrome P450 (CYP152B1) from Sphingomonas paucimobilis: Substrate Structure Required for a α-Hydroxylation", Lipids, vol. 35, No. 4, 2000, pp. 365-371.

Oliver, et al., "A Single Mutation in Cytochrome P450 BM3 Changes Substrate Orientation in a Catalytic Intermediate and the Regiospecificity of Hydroxylation", Biochemistry, vol. 36, No. 7, 1997, pp. 1567-1572.

Pearson et al., "Improved tools for biological sequence comparison", Proc. Natl. Acad. Sci. USA, 1988, vol. 85, pp. 2444-2448.

Roberts, "The power of evolution: accessing the synthetic potential of P450s", Chemistry & Biology, 1999, vol. 6, No. 10, pp. R269-R272.

Thomas, et al., "Molecular Sieve Catalysts for the Regioselective and shape-Selective Oxyfunctionalization of Alkanes in Air" Acc. Chem. Res. 2001, vol. 34, pp. 191-200.

van Deurzen et al.,"Selective Oxidations Catalyzed By Peroxidases", Tetrahedron Report No. 427, vol. 53, No. 39, 1997, pp. 13183-13220.

Yeom, et al., "The Role of Thr268 in oxygen activation of cytochrome P450BM-3", Biochemistry, 1995, vol. 34, No. 45, pp. 14733-14740.

Abecassis et al., Nucleic Acids Res., 2000, vol. 28, E88.

Abecassis et al., "Design and characterization of a novel "family-shuffling" technology adapted to membrane enzyme: application to P450s involved in xenobiotic metabolism," Adv. Exp. Med. Biol. 500, 2001, pp. 319-322.

Abecassis et al., "Exploration of natural and artificial sequence spaces: Towards a functional remodeling of membrane-bound cytochrome P450," Biocatal. Biotransform, 2003, vol. 21, No. 2, pp. 55-66.

Appel et al., "A P450 BM-3 mutant hydroxylates alkanes, cycloalkanes, arenes and heteroarenes," Journal of Biotechnology, 2001, vol. 88, No. 2, pp. 167-171.

Assis et al., "Hydrocarbon oxidation with iodosylbenzene catalysed by the sterically hindered iron(III) 5-(pentafluorophenyl)-10, 15, 20-tris(2,6-dichlorophenyl) porphyrin in homogeneous solution and covalently bound to silica," Journal of The Chemical Society-Perkin Transactions 2, 1998, vol. 10, pp. 2221-2226.

Barnes et al., "Expression and enzymatic activity of recombinant cytochrome P450 17α-hydroxylase in *Escherichia coli*," Proc. Natl. Acad. Sci. USA, Jul. 1991, vol. 88, pp. 5597-5601.

Bell et al., "Butane and propane oxidation by engineered cytochrome P450(cam)," Chemical Communications, 2002, vol. 5, pp. 490-491.

Bell et al., "Engineering cytochrome P450cam into an alkane hydroxylase," Dalton Transactions, 2003, vol. 11, pp. 2133-2140.

Blay et al., "Alkane oxidation by a carbonxylate-bridged dimanganese(III) complex," Chemical Comuunications, 2001, vol. 20, pp. 2102-2103.

Boddupalli et al., "Fatty acid monooxygenation by cytochrome P-450$_{BM-3}$," The Journal of Biological Chemistry, Mar. 15, 1990, vol. 265, No. 8, pp. 4233-4239.

Bogarad et al., "A hierarchical apparoach to protein molecular evolution," Proc Natl Acad Sci USA, 1999, vol. 96, pp. 2591-2595.

Branden et al., "Introduction to protein structure," 1991, pp. 247, Garland Publishing Inc., New York.

Campbell et al., "Chimeric proteins can exceed the sum of their parts: Implication for evolution and protein design," Nat. Biotechnol, May 1997, vol. 15, pp. 439-443.

Capdevila et al., "The highly stereoselective oxidation of polyunsaturated fatty acids by cytochrome P450BM-3," The Journal of Biological Chemistry, Sep. 13, 1996, vol. 271, No. 37, pp. 22663-22671.

Chavez et al., "Syntheses, structures, and reactivities of cobalt(III)-alkylperoxo complexes and their role in stoichiometric and catalytic oxidation of hydrocarbons," Journal of the American Chemical Society, 1998, vol. 120, No. 35, pp. 9015-9027.

Chen et al., "Sterospecific alkane hydroxylation by non-heme iron catalysts: mechanistic evidence for an Fe-V=O active speices," Journal of the American Chemical Society, 2001, vol. 123, No. 26, pp. 6327-6337.

Christians et al., Directed evolution of thymidine kinase for AZT phosphorylation using DNA family shuffling, 1999, Nat. Biotechnol, vol. 17, pp. 259-264.

Cirino et al., "A self- sufficient peroxide-driven hydroxylation biocatalyst," Angewandte Chemie International Edition, 2003, vol. 42, No. 28, pp. 3299-3301.

Cirino et al., "Exploring the diversity of heme enzymes through directed evolution," In *Directed Molecular Evolution of Proteins*, 2002, pp. 215-243, S. Brakmann and K. Johnsson, eds. (Germany: Wiley-VCH).

Coco et al., Nat. Biotechnol., 2001, vol. 19, pp. 354-359.

Crameri et al., "DNA shuffling of a family of genes from diverse species accelerates directed evolution," Nature, 1998, vol. 391, pp. 288-291.

Cui et al., "Recombinatoric exploration of novel folded structures: a heteropolymer-based model of protein evolutionary landscapes," Proc Natl Acad Sci USA, 2002, vol. 99, pp. 809-814.

de Visser et al., "Hydrogen bonding modulates the selectivity of enzymatic oxidation by P450: Chameleon oxidant behavior by compound I," Angewandte Chemie-International Edition, 2002, vol. 41, No. 11, pp. 1947-+.

de Visser et al., "What factors affect the regioselectivity of oxidation by cytochrome P450? A DFT study of allylic hydroxylation and double bond epoxidation in a model reaction," Journal of the American Chemical Society, 2002, vol. 124, No. 39, pp. 11809-11826.

Elliot et al., "Regio- and stereoselectivity of particulate methane monooxygenase from Methylococcus capsulatus (Bath)," Journal of the American Chemical Society, 1997, vol. 199, No. 42, pp. 9949-9955.

Farinas et al., "Directed evolution of a cytochrome P450 monooxygenase for alkane oxidation," Adv. Synth. Catal., 2001, vol. 343, pp. 601-606.

Fisher et al., "Positional specificity of rabbit CYP4B1 for omega-hydroxylation of short-medium chain fatty acids and hydrocarbons," Biochemical and Biophysical Research Communications, 1998, vol. 248, No. 2, pp. 352-355.

Gibbs et al., "Degenerate oligonucleotide gene shuffling (DOGS): a method for enhancing the frequency of recombination with family shuffling," Gene, 2001, vol. 271, pp. 13-20.

Glieder et al., "High-throughput screens based on NAD(P)H depletion," Directed Enzyme Evolution: Screening and Selection Methods, 2003, vol. 230.

Glieder et al., "Laboratory evolution of a soluble, self-sufficient, highly active alkane hydroxylase," Nature Biotech., 2002, vol. 20, pp. 1135-1139.

Gonzalez et al., "Evolution of the P450 gene superfamily: animal-plant 'warfare', molecular drive and human genetic differences in drug oxidation," Trends Genet, 1990, vol. 6, pp. 182-186.

Gotoh, Cytochrome P450, 2nd Edition, 1993, pp. 255-272.

Graham- Lorence et al., "An active site substitution, F87V, converts cytochrome P450 BM-3 into a region- and stereoselective (14S, 15R)-arachidonic acid epoxygenase," The Journal of Biological Chemistry, Jan. 10, 1997, vol. 272, No. 2, pp. 1127-1135.

Hansson et al., J. Mol. Biol., 1999, vol. 287, pp. 265-276.

Hiraga et al., "General method for sequence-independent site-directed chimeragenesis," J. Mol. Biol., 2003, vol. 330, pp. 287-296.

Hopps, H.B., "Purpaid: a reagent that turns aldehydes purple," Aldrichim. Acta, 2000, vol. 33, pp. 28-30.

Horton et al., "Engineering hybrid genes without the use of restriction enzymes: gene splicing by overlap extention," Gene, 1989, vol. 77, pp. 61-68.

Jaeger et al., "Enantioselective biocatalysts optimized by directed evolution," Current Opinion in Biotechnology, 2004, vol. 15, No. 4, pp. 305-313.

Joo et al., Nature, 1999, vol. 399, pp. 670-673.

Kikuchi et al., Gene, 2000, vol. 243, pp. 133-137.

Kumamaru et al., "Enhanced degradation of polychlorinated biphenyls by directed evolution of biphenyl dioxygenase," Nat. Biotechnol., 1998, vol. 16, pp. 663-666.

Li et al., Chemistry, 2000, vol. 6, pp. 1531-1536.

Li et al., "Rational evolution of a medium chain-specific cytochrome P450 BM-3 variant," Biochem Biophys. Acta., 2001, vol. 1545, pp. 114-121.

Li et al., "Residue size at position 87 of cytochrome P450 BM-3 determines its stereoselectivity in propylbenzene and 3-chlorostyrene oxidation," FEBS Lett 508, 2001, pp. 249-252.

Lutz et al., Proc Natl Acad Sci USA, 2001, vol. 98, pp. 11248-11253.

Mauersberger et al., Z Alig Mikrobiol., 1981, vol. 121, pp. 313-321.

Meyer et al., "Library analysis of SCHEMA-guided protein recombination," Prot. Sci., 2003, vol. 12, No. 8, pp. 1686-1693.

Munro et al., "P450 BM3: The very model of a modern flavocytochrome," Trends Biochem. Sci., 2002, vol. 27, pp. 250-257.

Narhi et al., "Characterization of catalytically self-sufficient 119,000-dalton cytochrome P-450 monooxygenase induced by barbiturates in Bacillus megaterium," The Journal of Biological Chemistry, Jun. 5, 1986, vol. 261, No. 16, pp. 7160-7169.

Narhi et al., "Identification and characterization of two functional domains in cytochrome P-450$_{BM-3}$, a catalytically self-sufficient monooxygenase induced by barbiturates in Bacillus megaterium," The Journal of Biological Chemistry, May 15, 1987, vol. 262, No. 14, pp. 6683-6690.

Neylon, C., "Chemical and biochemical strategies for the randomization of protein encoding DNA sequences: library construction methods for directed evolution," Nucleic Acids Res., 2004, vol. 32, No. 4, pp. 1448-1459.

Ohkuma et al., "Cyp52 (Cytochrome-P450alk) multigene family in candida-maltosa—Identification and characterization of 8 members," DNA and Cell Biology, 1995, vol. 14, No. 2, pp. 163-173.

Oliver et al., "Engineering the substrate specificity of Bacillus megaterium cytochrome P-450 BM3: hydroxylation of alkyl trimethylammonium compounds," Biochem. J., 1997, vol. 327, pp. 537-577.

O'Maille et al., Structure-based combinatorial protein engineering (SCOPE), J. Mol. Biol., 2002, vol. 321, pp. 677-691.

Otey et al., "Functional evolution and structural conservation in chimeric cytochromes P450: Calibrating a structure-guided approach," Chemistry and Biology, 2004, vol. 11, pp. 309-318.

Peterson et al., "The many faces of P450s and their structural and functional implications," Sixth International Symposium on Cytochrome P450 Biodiversity: University of California, Los Angeles, 2002.

Pompon et al., Protein engineering by cDNA recombination in yeasts: shuffling of mammalian cytochrome P-450 functions, Gene, 1989, vol. 83, pp. 15-24.

Porter et al., J. Biol. Chem., 1991, vol. 266, pp. 13469-13472.

Porter, "Cytochrome P450 reductase," printed Apr. 5, 2004, http://www.uky.edu/Pharmacy/ps/porter/CPR.htm.

Ramarao et al., "Identification by in Vitro mutagenesis of the interaction of two segments of C2MstC1, a chimera of cytochromes P450 2C2 and P450 2C1," The Journal of Biological Chemistry, Jan. 27, 1995, vol. 270, No. 4, pp. 1873-1880.

Ruettinger et al., "Epoxidation of unsaturated fatty acids by a soluble cytochrome P-450- dependent system from Bacillus megaterium," The Journal of Biological Chemistry, Jun. 10, 1981, vol. 256, No. 11, pp. 5728-5734.

Schneider et al., "Controlled regioselectivity of fatty acid oxidation by whole cells producing cytochrome P450(BM-3) monooxygenase under varied dissolved oxygen concentrations," Biotech. Bioeng., 1999, vol. 64, No. 3, pp. 333-340.

Schneider et al., "Production of chiral hydroxyl long chain fatty acids by whole cell biocatalysis of pentadecanoic acid with an E. coli recombinant containing cytochrome P450(BM-3) monooxygenase," Tetrahedron Asymmetry, 1998, vol. 9, No. 16, pp. 2833-2844.

Schwaneberg et al., "Cost-effective whole-cell assay for laboratory evolution of hydroxylases in Escherichia coli.," Journal of Biomolecular Screening, 2001, vol. 6, No. 2, pp. 111-117.

Seghezzi et al., "Identification of characterization of additional members of the cytochrome-P450 multigene family Cyp52 of candida-tropicalis," DNA and Cell Biology, 1992, vol. 11, No. 10, pp. 767-780.

Sieber et al., Nat Biotechnol, 2001, vol. 19, pp. 456-460.

Sono et al., "Heme-containing oxygenases," Chemical Reviews, 1996, vol. 96, No. 7, pp. 2841-2887.

Stemmer, Proc. Natl. Acad. Sci. USA, 1994, vol. 91, pp. 10747-10751.

Stevenson et al., "Engineering molecular recognition in alkane oxidation catalysed by cytochrome P450(cam)," New Journal of Chemistry, 1998, vol. 22, No. 6, pp. 551-552.

Stevenson et al., "The catalytic oxidation of linear and branched alkanes by cytochrome P450cam.," J. Am. Chem. Soc., 1996, vol. 1 118, pp. 12846-12847.

Taly et al., "A combinatorial approach to substrate discrimination in the P450 CYP1A subfamily," Biochimica et Biophysica Acta, 2007, vol. 1770, pp. 446-457.

Tsotsou et al., "High throughput assay for cytochrome P450BM3 for screening libraries of substrates and combinatorial mutants," Biosensors & Bioelectronics, 2002, vol. 17, No. 1-2, pp. 119-131.

Urlacher et al., "Biotransformations using prokaryotic P450 monooxygenases," Current Opinion in Biotechnology, 2002, vol. 13, pp. 557-564.

Voigt et al., "Protein building blocks preserved by recombination," Nat. Struct. Biol., 2002, vol. 9, pp. 553-558.00.

Volkov et al., "Recombination and chimeragenesis by in vitro heteroduplex formation and in vivo repair," Nucleic Acids Res., 1999, vol. 27, e18.

Wubbolts et al., "Enantioselective oxidation by non-heme iron monooxygenases from Pseudomonas," Chimia, 1996, vol. 50, No. 9, pp. 436-437.

Zhao et al., "Molecular evolution by staggered extension process (StEP) in vitro recombination," Nature Biotechnology, 1998, vol. 16, pp. 258-261.

"Enzymology of cytochrome P450 reductase," printed Apr. 5, 2004, http://www.uky.edu/Pharmacy/ps/porter/CPR_enzymology.htm.

"Researchers break electronics speed record. New diode may lead to new generation of faster, cheaper, smaller electronics," printed Apr. 14, 2004, http://www.nsf.gov/od/lpa/news/04/tip040115.htm.

Adam et al., "Microbial Asymmetric CH Oxidations of Simple Hydrocarbons: A Novel Monooxygenase Activity of the Topsoil Microorganism *Bacillus megaterium*," *Eur. J. Org. Chem.*, 2000, pp. 2923-2926, Wiley-VCH Verlag GmbH, Weinheim, Germany.

Aisaka et al., "Production of Galactose Oxidase by *Gibberella fujikuroi*," *Agric. Biol. Chem.*, 1981, pp. 2311-2316, 45(10).

Amaral et al., "Galactose Oxidase of *Polyporus circinatus*[1-4]," *Methods in Enzymology, Carbohydrate Metabolism*, 1966, pp. 87-92, vol. 9, Academic Press Inc., New York, NY, USA.

Anfinsen, "Principles that Govern the Folding of Protein Chains," *Science*, Jul. 20, 1973, pp. 223-230, vol. 181, No. 4096, American Asso for the Advancement of Science, Washington, DC, USA.

Arkin et al., "An algorithm for protein engine ring: Simulations of recursive ensemble mutagenesis," *Proc. Natl. Acad. Sci- USA*, Aug. 1992, pp. 7811-7815, vol. 89, Applied Biological Sciences.

Arnold, "Design by Directed Evolution," *Accounts of Chemical Research*, 1998, pp. 125-131, vol. 31, No. 3, American Chemical Society.

Arnold, "Engineering proteins for nonnatural environments," *The FASEB Journal*, Jun. 1993, pp. 744-749, vol. 7, No. 6, FASEB, Bethesda, MD, USA.

Arnold et al., "Optimizing Industrial Enzymes by Directed Evolution," *Advances in Biochemical Engineering/Biotechnology*, 1997, pp. 1-14, vol. 58, Springer-Verlag, Berlin, Germany.

Arts et al., "Hydrogen Peroxide and Oxygen in Catalytic Oxidation of Carbohydrates and Related Compounds," *Synthesis Journal of Synthetic Organic Chemistry*, Jun. 1997, pp. 597-613.

Ashraf et al., "Bacterial oxidation of propane," *FEMS Microbiology Letters*, 1994, pp. 1-6, Federation of European Microbiological Societies, Elsevier.

Avigad, "Oxidation Rates of Some Desialylated Glycoproteins by Galactose Oxidase," *Archives of Biochemistry and Biophysics*, Jun. 1985, pp. 531-537, vol. 239, No. 2, Academic Press, Inc.

Avigad, "An NAHD Coupled Assay System for Galactose Oxidase," *Analytical Biochemistry*, 1978, pp. 470-476, 86, Academic Press, Inc.

Avigad et al., "The $_D$-Galactose Oxidase of *Polyporus circinatus*," *Journal of Biological Chemistry*, Sep. 1962, pp. 2736-2743, vol. 237, No. 9, American Society of Biological Chemists, Baltimore, MD, USA.

Barnes, "Maximizing Expression of Eukaryotic Cytochrome P450s in *Escherichia coli*," Methods in Enzymology, Cytochrome P450, Part B, 1996, pp. 3-14, vol. 272, Academic Press, Inc., San Diego, CA, USA.

Baron et al., "Structure and Mechanism of Galactose Oxidase," *The Journal of Biological Chemistry*, Sep. 23, 1994, pp. 25095-25105, vol. 269, No. 38, American Soc for Biochemistry and Molecular Biology.

Benson et al., "Regulation of Membrane Peptides by the *Pseudomonas* Plasmid *alk* Regulon," *Journal of Bacteriology*, Dec. 1979, pp. 754-762, vol. 140, No. 3.

Better et al., "*Escherichia coli* Secretion of an Active Chimeric Antibody Fragment," *Science*, May 20, 1988, pp. 1041-1043, vol. 240, American Asso for the Advancement of Science, Washington, DC, USA.

Boddupalli et al., "Fatty Acid Monooxygenation by P450$_{BM-3}$: Product Identification and Proposed Mechanisms for the Sequential Hydroxylation Reactions," Archives of Biochemistry and Biophysics, Jan. 1992, pp. 20-28, vol. 292, No. 1, Academic Press, Inc.

Borman et al., "Kinetic studies on the reactions of *Fusarium* galactose oxidase with five different substrates in the presence of dioxygen," *Journal of Biological Inorganic Chemistry*, 1997, pp. 480-487, Society of Biological Inorganic Chemistry.

Bradford, "A Rapid and Sensitive Method for the Quantitation of Microgram Quantities of Protein Utilizing the Principle of Protein-Dye Binding," *Analytical Biochemistry*, pp. 248-254.

Calderhead, D. et al., "Labeling of Glucose Transporters at the Cell Surface in 3T3-L1 Adipocytes," *The Journal of Biological Chemistry*, Sep. 5, 1988, pp. 12171-12174, vol. 263, No. 25, The American Society for Biochemistry and Molecular Biology.

Calvin, N. et al., "High-Efficiency Transformation of Bacterial Cells by Electroporation," *Journal of Bacteriology*, Jun. 1988, pp. 2796-2801, vol. 170, No. 6, American Society for Microbiology.

Cameron, A., "Two cradles for the heavy elements," *Nature*, Jan. 15, 1998, pp. 228-231, Vol. 39.

Carmichael, A. et al., "Protein engineering of *Bacillus megaterium* CYP102," *Eur. J. Biochem.*, 2001, pp. 3117-3125, vol. 268, FEBS.

Castelli, L. et al., "High-level secretion of correctly processed β-lactamase from *Saccharomyces cerevisiae* using a high-copy-number secretion vector," *Gene*, 1994, pp. 113-117, vol. 142, Elsevier Science B.V.

Chang, C. et al., "Evolution of a cytokine using DNA family shuffling," *Nature Biotechnology*, Aug. 1999, pp. 793-797, vol. 17.

Chang, Y. et al.., "Homology Modeling, Molecular Dynamics Simulations, and Analysis of CYP119, a P450 Enzyme from Extreme Acidothermophilic Archaeon *Sulfolobus solfataricus*," *Biochemistry*, 2000, pp. 2484-2498, vol. 39, No. 10, American Chemical Society.

Chen, H. et al., "Thermal, Catalytic, Regiospecific Functionalization of Alkanes," *Science*, Mar. 17, 2000, pp. 1995-1997, vol. 287.

Chen, K. et al., "Tuning the activity of an enzyme for unusual environments: Sequential random mutagenesis of subtilisin E for catalysis in dimethylformamide," *Proc. Natl. Acad. Sci. USA*, Jun. 15, 1993, pp. 5618-5622, vol. 90, No. 12.

Cherry, J. et al., "Directed evolution of a fungal peroxidase," *Nature Biotechnology*, Apr. 1999, pp. 379-384, vol. 17, Nature America Inc., New York, NY, USA.

Cleland, J. et al., "Cosolvent Assisted Protein Refolding," *Biotechnology*, Dec. 1990, pp. 1274-1278, vol. 8.

Crameri, A. et al., "Molecular evolution of an arsenate detoxification pathway by DNA shuffling," *Nature Biotechnology*, May 1997, pp. 436-438, vol. 15, Nature America Inc., New York, NY, USA.

Crameri, A. et al., "Improved Green Fluorescent Protein by Molecular Evolution Using DNA Shuffling," *Nature Biotechnology*, Mar. 1996, pp. 315-319, vol. 14, Nature America Inc., New York, NY, USA.

Crameri, A. et al., "Construction and evolution of antibody-phage libraries by DNA shuffling," *Nature Medicine*, Jan. 1996, pp. 100-106, vol. 2, No. 1.

Dahlhoff, W. et al., "$_L$-Glucose or $_D$-*gluco*-Hexadialdose from $_D$-Glucurono-6,3- lactone by Controlled Reductions," *Angew. Chem. Int. Ed. Engl.*, 1980, pp. 546-547, 19 No. 7, Verlag Chemie, GmbH, Weinheim, Germany.

Danon, A., et al. "Enrichment of Rat Tissue Lipids with Fatty Acids that are Prostaglandin Precursors" *Biochimica et Biophysica Acta*, 1975, 388: 318-330.

De Bernardez-Clark, E. et al., "Inclusion Bodies and Recovery of Proteins from the Aggregated State," *ACS Symposium Series Protein Refolding, 199th Natl Mtg American Chemical Society*, Apr. 22-27, 1990, pp. 1-20, American Chemical Society, Washington, DC, USA.

Deacon, S. et al., "Enhanced Fructose Oxidase Activity in a Galactose Oxidase Variant," *ChemBioChem: A European Journal of Chemical Biology*, 2004, pp. 971-979, 5, Wiley-VCH Verlag GmbH & Co., Weinheim, Germany.

Delagrave, S. et al., "Recursive ensemble mutagenesis," *Protein Engineering*, Apr. 1993, pp. 327-331, vol. 6, No. 3, Oxford University Press.

Delagrave, S. et al., "Searching Sequence Space to Engineer Proteins: Exponential Ensemble Mutagenesis," *Bio/Technology*, Dec. 1993, pp. 1548-1552, vol. 11, American Society for Cell Biology, New Orleans, LA, USA.

Dordick, J., "Designing Enzymes for Use in Organic Solvents," *Biotechnol. Prog.*, 1992, pp. 259-267, 8, American Chemical Society and American Institute of Chemical Engineers.

Dower, W. et al., "High efficiency transformation of *E. coli* by high voltage electroporation," *Nucleic Acids Research*, 1988, pp. 6127-6145, vol. 16, No. 13, IRL Press Limited, Oxford, England.

Fiedler, K., et al., The Role of N-Glycans in the Secretory Pathway, *Cell*, May 5, 1995, pp. 309-312, vol. 81, Cell Press.

Fox, B., et al., "Methane Monooxygenase from *Methylosinus trichosporium* OB3b," *Methods in Enzymology*, 1990, pp. 191-202, vol. 188, Academic Press, Inc.

Fox, B., et al., "Methane Monooxygenase from *Methylosinus trichosporium* OB3b Purification and Properties of a Three-Component System with High Specific Activity from a Type II Methanotroph," *The Journal of Biological Chemistry*, Jun. 15, 1989, pp. 10023-10033, vol. 264, No. 17, The American Society for Biochemistry and Molecular Biology, Inc.

Fruetel, J., et al., "Relationship of Active Site Topology to Substrate Specificity for Cytochrome P450$_{terp}$ (CYP108)," *The Journal of Biological Chemistry*, Nov. 18, 1994, pp. 28815-28821, vol. 269, No. 46, The American Society for Biochemistry and Molecular Biology, Inc.

Gahmberg C., et al., "Nonmetabolic Radiolabeling and Taggin of Glycoconjugates," *Methods in Enzymology*, 1994, pp. 32-44, vol. 230, Academic Press, Inc.

Gazaryan, I.G., "Heterologous Expression of Heme-Containing Peroxidases," *Plant Peroxidase Newsletter*, Sep. 1994, pp. 11-13, No. 4, LABPV Newsletters.

Gietz, R., et al., "Studies on the Transformation of Intact Yeast Cells by the LiAc/SS-DNA/PEG Procedure," *Yeast*, Apr. 15, 1995, pp. 355-360, vol. 11, No. 4, John Wiley & Sons Ltd.

Gillam, E., et al., "Expression of Cytochrome P450 2D6 in *Escherichia coli*, Purification, and Spectral and Catalytic Characterization," *Archives of Biochemistry and Biophysics*, Jun. 1, 1995, pp. 540-550, vol. 319, No. 2, Academic Press, Inc.

Giver, L., et al., "Combinatorial Protein Design by In Vitro Recombination," *Current Opinion in Chemical Biology*, 1998, pp. 335-338, vol. 2, Current Biology Ltd.

Giver, L., et al., "Directed Evolution of a Thermostable Esterase," *Proc. Natl. Acad. Sci. USA*, Oct. 1998, pp. 12809-12813, vol. 95.

Goldman, E., et al., "An Algorithmically Optimized Combinatorial Library Screened by Digital Imaging Spectroscopy," *Biotechnology*, Dec. 1992, pp. 1557-1561, vol. 10.

Gram, H., et al., "In Vitro Selection and Affinity Maturation of Antibodies from a Naive Combinatorial Immunoglobulin Library," *Proc. Natl. Acad. Sci. USA*, Apr. 1992, pp. 3576-3580, vol. 89.

Green, J., et al., "Substrate Specificity of Soluble Methane Monooxygenase Mechanistic Implications," *The Journal of Biological Chemistry*, Oct. 25, 1989, pp. 17698-17703, vol. 264, No. 30, The American Society for Biochemistry and Molecular Biology, Inc.

Griebenow, K., et al., Lyophilization-Induced Reversible Changes in the Secondary Structure of Proteins, *Proc. Natl. Acad. Sci. US*, Nov. 1995, pp. 10969-10976, vol. 92.

Groves, J., et al., "Models and Mechanisms of Cytochrome P450 Action," *Cytochrome P450: Structure, Mechanism, and Biochemistry (Second Edition)*, 1995, pp. 3-48, Plenum Press, New York.

Guengerich, F., et al., "Purification of Functional Recombinant P450s from Bacteria," *Methods in Enzymology*, 1996, pp. 35-44, vol. 272, Academic Press, Inc.

Güssow, D., et al., "Direct Clone Characterization from Plaques and Colonies by the Polymerase Chain Reaction," *Nucleic Acids Research*, 1989, p. 4000, vol. 17, No. 10, IRL Press.

Haines, D., et al., "Pivotal Role of Water in the Mechanism of P450BM-3," *Biochemistry*, 2001, pp. 13456-13465, vol. 40, No. 45, American Chemical Society.

Hamilton, G.A., et al., "Galactose Oxidase: The Complexities of a Simple Enzyme," *Oxidases and Related Redox Systems*, 1973, pp. 103-124, vol. 1, University Park Press.

Hamilton, G.A., et al., "Trivalent Copper, Superoxide, and Galactose Oxidase," *Journal of the American Chemical Society*, Mar. 15, 1978, pp. 1899-1912, vol. 100, No. 6, American Chemical Society.

Hartmann, M., et al., "Selective Oxidations of Linear Alkanes with Molecular Oxygen on Molecular Sieve Catalysts—A Breakthrough?," *Agnew. Chem. Int. Ed. 2000*, pp. 888-890, vol. 39, No. 5.

Haschke, R., et al., "Calcium-Related Properties of Horseradish Peroxidase," *Biochemical and Biophysical Research Communications*, Feb. 28, 1978, pp. 1039-1042, vol. 80, No. 4, Academic Press, Inc.

Helenius, A., "How N-linked Oligosaccharides Affect Glycoprotein Folding in the Endoplasmic Reticulum," *Molecular Biology of the Cell*, Mar. 1994, pp. 253-265, vol. 5, No. 3, The American Society for Cell Biology.

Hermes, J., et al., "Searching Sequence Space by Definably Random Mutagenesis: Improving the Catalytic Potency of an Enzyme," *Proc. Natl. Acad. Sci. USA*, Jan. 1990, pp. 696-700, vol. 87.

Ito, N. et al., "X- Ray Crystallographic Studies of Cofactors in Galactose Oxidase," *Methods in Enzymology, Redox-Active Amino Acids in Biology*, 1995, pp. 235-262, vol. 258, Academic Press, Inc.

Ito, N. et al., "Crystal Structure of a Free Radical Enzyme, Galactose Oxidase," *Journal of Molecular Biology*, 1994, pp. 794-814, vol. 238, No. 5, Academic Press Limited.

Ito, N. et al., "Novel thioether bond revealed by a 1.7 Å crystal structure of galactose oxidase," *Nature*, Mar. 7, 1991, pp. 87-90.

Joo, H. et al., "A high-throughput digital imaging screen for the discovery and directed evolution of oxygenases," *Chemistry & Biology*, Oct. 1999, pp. 699-706, vol. 6, No. 10.

Khoslat, C. et al., "Expression of Intracellular Hemoglobin Improves Protein Synthesis in Oxygen-Limited *Escherichia coli*," *Bio/Technology*, Sep. 1990, pp. 849-853, American Society for Cell Biology, New Orleans, LA, USA.

Kiba, N. et al., "A post-column co-immobilized galactose oxidase/peroxidase reactor for fluorometric detection of saccharides in a liquid chromatographic system," *Journal of Chromatography*, 1989, pp. 183-187, vol. 463, Elsevier Science Publishes B.V., Amsterdam, The Netherlands.

Kim, J. et al., "Use of 4-(Nitrobenzyl)Pyridine (4-NBP) To Test Mutagenic Potential of Slow-Reacting Epoxides, Their Corresponding Olefins, and Other Alkylating Agents," *Bull. Environ. Contam. Toxicol.*, 1992, pp. 879-885, vol. 49, Springer-Verlag New York Inc.

Klibanov, A. et al., "Stereospecific Oxidation of Aliphatic Alcohols Catalyzed by Galactose Oxidase," *Biochemical and Biophysical Research Communications*, 1982, pp. 804-808, vol. 108, No. 2, Academic Press, Inc.

Knappik, A. et al., "Engineered turns of a recombinant antibody improve its in vivo folding," *Protein Engineering*, Jan. 1995, pp. 81-89, vol. 8, No. 1, Oxford University Press.

Koroleva, O. et al., "Properties of *Fusarium graminearum* Galactose Oxidase," 1984, pp. 500-509, Plenum Publishing Corporation.

Kosman, D., "Chapter 1 Galactose Oxidase," in Lontie, R., Eds., *Copper Proteins and Copper Enzymes* vol. II, pp. 1-26, CRC Press, Inc., Boca Raton, FL, USA.

Koster, R. et al., "Organoboron Monosaccharides; XII[1]. Quantitative Preparation of $_D$-*gluco*-Hexodialdose from Sodium $_D$-Glucuronate or $_D$-Glucuronic acid," *Synthesis*, Aug. 1982, pp. 650-652, No. 8, Georg Thieme Verlag.

Kuchner, O. et al., "Directed evolution of enzyme catalysts," *Biotechnology*, Dec. 1997, pp. 523-530, vol. 15, Elsevier Science Ltd.

Kuhn-Velten, W., "Effects of Compatible Solutes on Mammalian Cytochrome P450 Stability," 1997, pp. 132-135, Verlag der Zeitschrift für Naturforschung.

Kvittingen, L. et al., "Use of Salt Hydrates to Buffer Optimal Water Level During Lipase Catalysed Synthesis in Organic Media: A Practical Procedure for Organic Chemists," *Tetrahedron*, 1992, pp. 2793-2802, vol. 48, No. 13, Pergamon Press Ltd., Great Britain.

Lei, S. et al., "Characterization of the *Erwinia carotovora pelB* Gene and Its Product Pectate Lyase," *Journal of Bacteriology*, Sep. 1987, pp. 4379-4383, vol. 169, No. 9, American Society for Microbiology.

Leadbetter, E. R., et al. "Incorporation of Molecular Oxygen in Bacterial Cells Utiizing Hydrocarbons for Growth" Natures; Oct. 31, 1959; vol. 184, pp. 1428-1429.

Leung, D. et al., "A Method for Random Mutagenesis of a Defined DNA Segment Using a Modified Polymerase Chain Reaction," *Technique, A Journal of Methods in Cell and Molecular Biology*, Aug. 1989, pp. 11-15, vol. 1, No. 1, Saunders Scientific Publications.

Lewis, D., "P450 Substrate Specificity and Metabolism," *Cytochromes P450: Structure, Function and Mechanism*, Aug. 2001, pp. 115-166, Taylor & Francis Publishers.

Li, H. et al., "The structure of the cytochrome p450BM-3 haem domain complexed with the fatty acid substrate, palmitoleic acid," *Nature Structural Biology*, Feb. 1997, pp. 140-146, vol. 4, No. 2.

Lis, M. et al., "Galactose Oxidase-Glucan Binding Domain Fusion Proteins as Targeting Inhibitors of Dental Plaque Bacteria," *Antimicrobial Agents & Chemotherapy*, May 1997, pp. 999-1003, vol. 41, No. 5, American Society for Microbiology.

Liu, C. et al., "Sugar-containing Polyamines Prepared Using Galactose Oxidase Coupled with Chemical Reduction," *J. Am. Chem. Soc.*, Jan. 20, 1999, pp. 466-467, vol. 121, No. 2, American Chemical Society.

Mannino, S. et al., "Simultaneous Determination of Glucose and Galactose in Dairy Products by Two Parallel Amperometric Biosensors," *Italian Journal of Food Science*, 1999, pp. 57-65, vol. 11, No. 1, Chiriotti Editori, s.p.a., Pinerolo, Italy.

Maradufu, A. et al., "A Non-Hydrogen-Bonding Role for the 4-Hydroxyl Group of $_D$-Galactose in its Reaction with $_D$-Galactose Oxidase," *Carbohydrate Research*, 1974, pp. 93-99, 32, Elsevier Scientific Publishing Company, Amsterdam, The Netherlands.

Maradufu, A. et al., "Stereochemistry of Dehydrogenation by $_D$-Galactose Oxidase," *Canadian Journal of Chemistry*, Oct. 1971, pp. 3429-3437, vol. 49, No. 19, NCR Research Press, Ottawa, Canada.

March, J., *Advanced Organic Chemistry: Reactions, Mechanisms, and Structure, 4$^{th}$ Edition*, 1992, pp. 882-884, Wiley and Sons, NY.

March, J., *Advanced Organic Chemistry: Reactions, Mechanisms, and Structure, 4$^{th}$ Edition*, 1992, pp. 1072-1074, Wiley and Sons, NY.

Martin, B. et al., "Highly swelling hydrogels from ordered galactose-based polyacrylates," *Biomaterials*, 1998, pp. 69-76, 19(1-3), Elsevier.

Martin, I. et al., "Detection of honey adulteration with beet sugar using stable isotope methodology," *Food Chemistry*, 1998, pp. 281-286, vol. 61, No. 3, Elsevier Science Ltd.

Martineau, P. et al., "Expression of an Antibody Fragment at High Levels in the Bacterial Cytoplasm," *J. Mol. Biol.*, 1998, pp. 117-127, vol. 280, No. 1, Academic Press.

Martinez, C. et al., "Cytochrome P450's: Potential Catalysts for Asymmetric Olefin Epoxidations," *Current Organic Chemistry*, 2000, pp. 263-282, vol. 4, No. 3, Bentham Science Publishers B.V.

Matson, R. et al., "Characteristics of a Cytochrome P-450-Dependent Fatty Acid ω-2 Hydroxylase From *Bacillus Megaterium*," *Biochimica et Biophysica Acta*, 1977, pp. 487-494, 487, Elsevier/North Holland Biomedical Press.

Mazur, A., "Chapter 8, Galactose Oxidase," *ACS Symposium Series 466—Enzymes in Carbohydrate Synthesis*, 1991, pp. 99-110, American Chemical Society, Washington, DC, USA.

Mazur, A., et al., "Chemoenzymic Approaches to the Preparation of 5-C-(Hydroxymethyl)hexoses," *J. Org. Chem.*, 1997, pp. 4471-4475, vol. 62, No. 13, American Chemical Society, Washington, DC, USA.

McPherson, M. et al., "Galactose oxidase of *Dactylium dendroides*. Gene cloning and sequence analysis," *Chemical Abstract Service*, XP-002298547, Database accession No. M86819.

McPerson, M. et al., "Galactose Oxidase of *Dactylium dendroides*," Apr. 1992, pp. 8146-8152, *The Journal of Biological Chemistry*, vol. 267, No. 12, The American Society for Biochemistry and Molecular Biology, Inc.

McPherson, M. et al., "Galactose oxidase: Molecular analysis and mutagenesis studies," *Biochemical Society Transactions, 646$^{th}$ Meeting Leeds*, 1993, pp. 1992-1994, vol. 21, The Biochemical Society, Portland Press.

Meinhold, P. et al., "Direct Conversion of Ethane to Ethanol by Engineered Cytochrome P450 BM3," *ChemBioChem*, 2005, pp. 1-4, vol. 6, Wiley-VCH Verlag GmbH & Co. Weinheim, Germany.

Mendonca, M. et al., "Purification and Characterization of Intracellular Galactose Oxidase from *Dactylium dendroides*," *Archives of Biochemistry and Biophysics*, Feb. 1987, pp. 507-514, vol. 252, No. 2, Academic Press, Inc.

Mendonca, M. et al., "Role of Carbohydrate Content on the Properties of Galactose Oxidase from *Dactylium dendroides*," *Archives of Biochemistry and Biophysics*, Nov. 1988, pp. 427-434, vol. 266, No. 2, Academic Press, Inc.

Miele, R., et al., "Glycosylation of Asparagine-28 of Recombinant Staphylokinase with High-Mannose-type Oligosaccharides Results in a Protein with Highly Attenuated Plasminogen Activator Activity," *Journal of Biological Chemistry*, Mar. 1999, pp. 7769-7776, vol. 274, No. 12, The American Society for Biochemistry and Molecular Biology, Inc.

Miles, C. et al., "Protein engineering of cytochromes P-450," *Biochimica et Biophysica Acta*, 2000, pp. 383-407, 1543, Elsevier Science B.V.

Minshull, J. et al., "Protein evolution by molecular breeding," *Chemical Biology*, 1999, pp. 284-290, 3, Elsevier Science Ltd.

Mitraki, A. et al., "Amino acid substitutions influencing intracellular protein folding pathways," *FEBS Letters*, Jul. 1992, pp. 20-25, vol. 307, No. 1, Elsevier Science Publishers B.V.

Miura, Y. et al., "ω-1, ω-2 and ω-3 Hydroxylation of Long-Chain Fatty Acids, Amides and Alcohols by a Soluble Enzyme System from *Bacillus Megaterium*," *Biochimica et Biophysica Acta*, 1975, pp. 305-317, 388, Elsevier Scientific Publishing Company, Amsterdam, The Netherlands.

Miyazaki, K. et al., "Directed Evolution Study of Temperature Adaptation in a Psychrophilic Enzyme," *Journal Mol. Biol.*, 2000, pp. 1015-1026, 297, Academic Press.

Modi, S. et al., "NMR Studies of Substrate Binding to Cytochrome $P_{450\ BM3}$: Comparisons to Cytochrome $P_{450\ cam}$," *Biochemistry*, 1995, pp. 8982-8988, vol. 34, No. 28, American Chemical Society.

Moore, J. et al., "Directed evolution of a *para*-nitrobenzyl esterase for aqueous-organic solvents," *Nature Biotechnology*, Apr. 1996, pp. 458-467, vol. 14.

Moore, J. et al., "Strategies for the in vitro Evolution of Protein Function: Enzyme Evolution by Random Recombination of Improved Sequences," *J. Mol. Biol.*, 1997, pp. 336-347, 272, Academic Press Limited.

Moser, C. et al., "Biological Electron Transfer," *Journal of Bioenergetics and Biomembranes*, Jun. 1995, pp. 263-274, vol. 27, No. 3, Plenum Publishing Corporation.

Munro, A. et al., "Probing electronic transfer in flavocytochrome P-450 BM3 and its component domains," *Eur. J. Biochem.*, 1996, pp. 403-409, 239, FEBS.

Munro, A. et al., "Alkane Metabnolism by Cytochrome P450 BM3," *Biochemical Society Transactions*, 1993, p. 412S, 21.

Murrell, J. et al., "Molecular biology and regulation of methane monooxygenase," *Arch. Microbiol.*, 2000, pp. 325-332, 173o.

Nagayama, Y. et al., "Role of Asparagine-linked Oligosaccharides in Protein Folding, Membrane Targeting, and Thyrotropin and Autoantibody Binding of the Human Thyrotropin Receptor," *Journal of Biological Chemistry*, Dec. 1998, pp. 33423-33428, vol. 273, No. 5, The American Society for Biochemistry and Molecular Biology, Inc.

Nakagawa, S. et al., "Construction of Catalase Deficient *Escherichia coli* Strains for the Production of Uricase," *Biosci. Biotech. Biochem.*, 1996, pp. 415-420, 60 (3), Japanese Society for Bioscience, Biotechnology and Agrochemistry.

Nakajima, H. et al., "Industrial Application of Adenosine 5'-Triphosphate Regeneration to Synthesis of Sugar Phosphates," ACS Symposium Series 466, Enzymes in Carbohydrate Synthesis, Chapter 9, pp. 110-120, American Chemical Society, Washington DC, 1991, Bednarski & Simon, Editors.

Narhi, L. et al., "Identification and Characterization of Two Functional Domains in Cytochrome $P-450_{BM-3}$, a Catalytically Self-sufficient Monooxygenase Induced by Barbiturates in *Bacillus megaterium*," *The Journal of Biological Chemistry*, May 1987, pp. 6683-6690, vol. 262, No. 14, The American Society of Biological Chemists, Inc.

Nelson, D., "Appendix A—Cytochrome P450 Nomenclature and Alignment of Selected Sequences," *Cytochrome P450: Structure, Mechanism, and Biochemistry, Second Ed.*, 1995, pp. 575-606, Plenum Press, NY.

Ness, J. et al., "DNA shuffling of subgenomic sequences of subtilisin," *Nature Biotechnology*, Sep. 1999, pp. 893-896, vol. 17, No. 9, Nature Publishing Group.

Noble, M. et al., "Roles of key active-site residues in flavocytochrome P450 BM3," *Biochem. J.*, 1999, pp. 371-379, 339, Biochemical Society.

Oliphant, A. et al., "Cloning of random-sequence oligodeoxynucleotides," *Gene*, 1986, pp. 177-183, 44, Elsevier Science Publishers B.V.

Omura, T. et al., "The Carbon Monoxide-binding Pigment of Liver Microsomes," *The Journal of Biological Chemistry*, Jul. 1964, pp. 2370-2378, vol. 239, No. 7, The American Society for Biochemistry and Molecular Biology.

Ortlepp, S. et al., "Expression and characterization of a protein specified by a synthetic horseradish peroxidase gene in *Escherichia coli*," *Journal of Biotechnology*, 1989, pp. 353-364, 11, Elsevier Science Publishers B.V.

Ost, T. et al., "Rational re-design of the substrate binding site of flavocytochrome P450 BM3," *FEBS Letters*, 2000, pp. 173-177, 486, Elsevier Science B.V.

Ostermeier, M. et al., "Incremental Truncation as a Strategy in the Engineering of Novel Biocatalysts," *Bioorganic & Medicinal Chemistry*, 1999, pp. 2139-2144, 7, Elsevier Science Ltd.

Parekh, R. et al., "Multicopy Overexpression of Bovine Pancreatic Trypsin Inhibitor Saturates the Protein Folding and Secretory Capacity of *Saccharomyces cerevisiae*," *Protein Expression and Purification*, 1995, pp. 537-545, 6, Academic Press.

Patten, P. et al., "Applications of DNA shuffling to pharmaceuticals and vaccines," *Biotechnology*, 1997, pp. 724-733, vol. 8, Elsevier Science Ltd.

Paulsen, M. et al., "Dramatic Differences in the Motions of the Mouth of Open and Closed Cytochrome P450BM-3 by Molecular Dynamics Simulations," *Proteins: Structure, Function and Genetics*, 1995, pp. 237-243, Wiley-Liss, Inc.

Peterson, J. et al., "Chapter 5—Bacterial P450s," *Cytochrome P450: Structure, Mechanism, and Biochemistry, Second Ed.*, 1995, pp. 151-180, Plenum Press, New York.

Rathore, D., et al., "Expression of Ribonucleolytic Toxin Restrictocin in *Escherichia coli*: Purification and Characterization," *FEBS Letters*, 1996, pp. 259-262, vol. 392, Federation of European Biochemical Societies.

Reynolds, M., et al., "Structure and Mechanism of Galactose Oxidase: Catalytic Role of Tyrosine 495," *JBIC*, 1997, pp. 327-335, vol. 2.

Rodriguez-Lopez, J., et al., "Role of Arginine 38 in Horseradish Peroxidase—A Critical Residue for Substrate Binding and Catalysis," *The Journal of Biological Chemistry*, Feb. 23, 1996, pp. 4023-4030, vol. 271, No. 8, The American Society for Biochemistry and Molecular Biology.

Romanos, M., et al., "Foreign Gene Expression in Yeast: a Review," *Yeast*, Jun. 1992, pp. 423-488, vol. 8, No. 6, John Wiley & Sons Ltd.

Root, R., et al., "Enzymatic Synthesis of Unusual Sugars: Galactose Oxidase Catalyzed Stereospecific Oxidation of Polyols," *Journal of the American Chemical Society*, 1985, pp. 2997-2999, vol. 107, No. 10, American Chemical Society.

Ruettinger, R., et al., "Coding Nucleotide, 5' Regulatory, and Deduced Amino Acid Sequences of P-450$_{BM-3}$, a Single Peptide Cytochrome P-450:NADPH-P-450 Reductase from *Bacillus megaterium*," *The Journal of Biological Chemistry*, Jul. 5, 1989, pp. 10987-10995, vol. 264, No. 19, The American Society for Biochemistry and Molecular Biology, Inc.

Said, I.T., et al., "Comparison of Different Techniques for Detection of Gal-GalNAc, an Early Marker of Colonic Neoplasia," *Histology and Histopathology*, Apr. 1999, pp. 351-357, vol. 14, No. 2, Jiménez Godoy, S.A.

Savenkova, M., et al. "Improvement of Peroxygenase Activity by Relocation of a Catalytic Histidine within the Active Site of Horseradish Peroxidase," *Biochemistry*, 1998, pp. 10828-10836, vol. 37, American Chemical Society.

Saysell, C., et al., "Properties of the Trp290His Variant of *Fusarium* NRRL 2903 Galactose Oxidase: Interactions of the GOase$_{semi}$ State with Different Buffers, Its Redox Activity and Ability to Bind Azide," *JBIC*, 1997, pp. 702-709, vol. 2.

Schatz, P., et al., "Genetic Analysis of Protein Export in *Escherichia coli*," *Annual Review of Genetics*, 1990, pp. 215-248, vol. 24, Annual Reviews, Inc., Palo Alto, CA.

Schein C., "Solubility as a Function of Protein Structure and Solvent Components," *Bio/Technology*, Apr. 1990, pp. 308-317, vol. 8, No. 4.

Scheller, U., et al., "Characterization of the *n*-Alkane and Fatty Acid Hydroxylating Cytochrome P450 Forms 52A3 and 52A4," *Archives of Biochemistry and Biophysics*, Apr. 15, 1996, pp. 245-254, vol. 328, No. 2, Academic Press, Inc.

Schlegel, R., et al., "Substrate Specificity of $_D$-Galactose Oxidase," *Carbohydrate Research*, Jun. 1968, pp. 193-199, vol. 7, No. 2, Elsevier Publishing Company, Amsterdam.

Schmid, A., et al., "Industrial Biocatalysis Today and Tomorrow," *Nature*, Jan. 11, 2001, pp. 258-268, vol. 409, Macmillian Magazines Ltd.

Schwaneberg, U., et al., "A Continuous Spectrophotometric Assay for P450 BM-3, a Fatty Acid Hydroxylating Enzyme, and Its Mutant F87A," *Analytical Biochemistry*, 1999, pp. 359-366, vol. 269, Academic Press.

Schwaneberg, U., et al., "P450 Monooxygenase in Biotechnology—Single-Step, Large-Scale Purification Method for Cytochrome P450 BM-3 by Anion-Exchange Chromatography," *Journal of Chromatography*, 1999, pp. 149-159, vol. 848, Elsevier Science B.V.

Shafikhani, S., et al., "Generation of Large Libraries of Random Mutants in *Bacillus subtilis* by PCR-Based Plasmid Multimerization," *BioTechniques*, Aug. 1997, pp. 304-310, vol. 23, No. 2.

Shanklin, J., et al., "Mössbauer Studies of Alkane ω-Hydroxylase: Evidence for a Diiron Cluster in an Integral-Membrane Enzyme," *Proc. Natl. Acad. Sci. USA*, Apr. 1997, pp. 2981-2986, vol. 94.

Shao, Z., et al., "Random-priming In Vitro Recombination: An Effective Tool for Directed Evolution," *Nucleic Acids Research*, Jan. 15, 1998, pp. 681-683, vol. 26, No. 2, Oxford University Press.

Shilov, A., et al., "Activation of C-H Bonds by Metal Complexes," *Chem. Rev.*, 1997, pp. 2879-2932, vol. 97, American Chemical Society.

Shindler, J., et al., "Peroxidase from Human Cervical Mucus—The Isolation and Characterisation," *European Journal of Biochemistry*, Jun. 1976, pp. 325-331, vol. 65, No. 2.

Sirotkin, K., "Advantages to Mutagenesis Techniques Generating Populations Containing the Complete Spectrum of single Codon Changes," *J. Theor. Biol.*, 1986, pp. 261-279, vol. 123, Academic Press Inc. (London) Ltd.

Smith, A., et al., "Expression of a Synthetic Gene for Horseradish Peroxidase C in *Escherichia coli* and Folding and Activation of the Recombinant Enzyme with $Ca^{2+}$ and Heme," *The Journal of Biological Chemistry*, Aug. 5, 1990, pp. 13335-13343, vol. 265, No. 22, The American Society for Biochemistry and Molecular Biology.

Smith, A., et al., "Substrate Binding and Catalysis in Heme Peroxidases," *Current Opinion in Chemical Biology*, (1998), pp. 269-278, vol. 2.

Spiro, T., et al., "Is the CO Adduct of Myoglobin Bent, and Does It Matter?," *Accounts of Chemical Research*, 2001, pp. 137-144, vol. 34, No. 2, American Chemical Society.

Staijen, I., et al., "Expression, Stability and Performance of the Three-Component Alkane Mono-oxygenase of *Pseudomonas oleovorans* in *Escherichia coli*," *Eur. J. Biochem.*, 2000, pp. 1957-1965, vol. 267.

Stemmer, W., "Rapid Evolution of a Protein In Vitro by DNA Shuffling," *Nature*, Aug. 4, 1994, pp. 389-391, vol. 370, No. 6488.

Stemmer, W., et al., "Selection of an Active Single Chain Fv Antibody from a Protein Linker Library Prepared by Enzymatic Inverse PCR," *BioTechniques*, 1993, pp. 256-265, vol. 14, No. 2.

Stevenson, J., et al., "The Catalytic Oxidation of Linear and Branched Alkanes by Cytochrome P450$_{cam}$," *J. Am. Chem. Soc.*, 1996, pp. 12846-12847, vol. 118, No. 50, American Chemical Society.

Studier, F., et al., "Use of T7 RNA Polymerase to Direct Expression of Cloned Genes," *Methods in Enzymology*, 1990, pp. 60-89, vol. 185, Academic Press, Inc.

Sun, L., et al., "Expression and Stabilization of Galactose Oxidase in *Escherichia coli* by Directed Evolution," *Protein Engineering*, Sep. 2001, pp. 699-704, vol. 14, No. 9, Oxford University Press.

Sun, L., et al., "Modification of Galactose Oxidase to Introduce Glucose 6-Oxidase Activity," *ChemBioChem: A European Journal of Chemical Biology*, Aug. 2, 2002, pp. 781-783, vol. 3, No. 8, Wiley-VCH-Vertag GmbH, Weinheim, Germany.

Szabó, E., et al., "Application of Biosensor for Monitoring Galactose Content," *Biosensors & Bioelectronics*, 1996, pp. 1051-1058, vol. 11, No. 10, Elsevier Science Limited.

Tams, J., et al., "Glycosylation and Thermodynamic Versus Kinetic Stability of Horseradish Peroxidase," *FEBS Letters*, 1998, pp. 234-236, vol. 421, Federation of European Biochemical Societies.

Thatcher, D., et al., "Protein Folding in Biotechnology," *Mechanisms of Protein Folding*, 1994, pp. 229-261, IRL Press, Oxford.

Tkac, J., et al., "Rapid and Sensitive Galactose Oxidase-Peroxidase Biosensor for Galactose Detection with Prolonged Stability," *Biotechnology Techniques*, 1999, pp. 931-936, Kluwer Academic Publishers.

Tonge, G., et al., "Purification and Properties of the Methane Monooxygenase nzyme System from *Methylosinus trichosporium* OB3b," *Biochem. J.*, 1977, pp. 333-344, vol. 161.

Tressel, P., et al., "A Simplified Purification Procedure for Galactose Oxidase," *Analytical Biochemistry*, Jun. 1980, pp. 150-153, vol. 105, No. 1, Academic Press, Inc.

Tressel, P., et al., "Galactose Oxidase from *Dactylium dendroides*," *Methods in Enzymology*, 1982, pp. 163-171, vol. 89, Academic Press.

Truan, G., et al., "Thr268 in Substrate Binding and Catalysis in P450BM-3," *Archives of iochemistry and Biophysics*, Jan. 1, 1998, pp. 53-64, vol. 349, No. 1, Academic Press.

Vega, F., et al., "On-line Monitoring of Galactoside Conjugates and Glycerol by Flow Injection Analysis," *Analytica Chimica Acta*, 1998, pp. 57-62, vol. 373, Elsevier Science B.V.

Vrbová, E., et al., "Preparation and Utilization of a Biosensor Based on Galactose Oxidase," *Collect. Czech. Chem. Commun.*, 1992, pp. 2287-2294, vol. 57.

Wachter, R., et al., "Molecular Modeling Studies on Oxidation of Hexopyranoses by Galactose Oxidase. An Active Site Topology Apparently Designed to Catalyze Radical Reactions, Either Concerted or Stepwise," *Journal of the American Chemical Society*, Mar. 9, 1996, pp. 2782-2789, vol. 118, No. 9.

Watkinson, R., et al., "Physiology of Aliphatic Hydrocarbon-Degrading Microorganisms," *Biodegradation*, 1990, pp. 79-92, vol. 1, Nos. 2/3, Kluwer Academic Publishers.

Welinder, K., "Amino Acid Sequence Studies of Horseradish Peroxidase," *European Journal of Biochemistry*, 1979, pp. 483-502.

Welinder, K., "Supplement to Amino Acid Sequence Studies of Horseradish Peroxidase," pp. 495-502.

Wetzel, R., et al., "Mutations in Human Interferon Gamma Affecting Inclusion Body Formation Identified by a General Immunochemical Screen," *Bio/Technology*, Aug. 1991, pp. 731-737, vol. 9.

Whittaker, M., et al., "The Active Site of Galactose Oxidase," *The Journal of Biological Chemistry*, 1988, pp. 6074-6080, vol. 263, No. 13, The American Society for Biochemistry and Molecular Biology, Inc.

Whittaker, M., et al., "Kinetic Isotope Effects as probes of the Mechanism of Galactose Oxidase," *Biochemistry*, 1998, pp. 8426-8436, vol. 37, American Chemical Society.

Wilkinson, D., et al., "Structural and Kinetic Studies of a Series of Mutants of Galactose Oxidase Identified by Directed Evolution," *Protein Engineering, Design & Selection*, Jan. 12, 2004, pp. 141-148, vol. 17, No. 2, Oxford University Press.

Yang, G., et al., "Gal-GalNAc: A biomarker of Colon Carcinogenesis," *Histology and Histopathology*, 1996, pp. 801-806, vol. 11.

Yano, T., et al., "Directed Evolution of an Aspartate Aminotransferase with New Substrate Specificities," *Proc. Natl. Acad. Sci. USA*, May 1998, pp. 5511-5515, vol. 95.

Yeom, H., et al., "Oxygen Activation by Cytochrome $P450_{BM-3}$: Effects of Mutating an Active Site Acidic Residue," *Archieves of Biochemistry and Biophysics*, Jan. 15, 1997, pp. 209-216, vol. 337, No. 2, Academic Press.

You, L., et al., "Directed Evolution of Subtilisin E in *Bacillus subtilis* to Enhance Total Activity in Aqueous Dimethylformamide," *Protein Engineering*, 1996, pp. 77-83, vol. 9, Oxford University Press.

Zhang, J., et al., "Directed Evolution of a Fucosidase from a Galactosidase by DNA Shuffling and Screening," *Proc. Natl. Acad. Sci. USA*, Apr. 1997, pp. 4504-4509, vol. 94.

Zhang, T., et al., "Circular Permutation of T4 Lysozyme," *Biochemistry*, 1993, pp. 12311-12318, vol. 32, No. 46, American Chemical Society.

Zhao, H., et al., "Directed Evolution Converts Subtilisin E into a Functional Equivalent of Thermitase," *Protein Engineering*, 1999, pp. 47-53, vol. 12, No. 1, Oxford University Press.

Zhao, H., et al., "Methods for Optimizing Industrial Enzymes by Directed Evolution," *Manual of Industrial Microbiology and Biotechnology (2d Ed.)*, 1999, pp. 597-604, ASM Press, Washington, D.C.

Zhao, H., et al., "Optimization of DNA Shuffling for High Fidelity Recombination," *Nucleic Acids Research*, 1997, pp. 1307-1308, vol. 25, No. 6, Oxford University Press.

Zimmer, T., et al., "The CYP52 Multigene Family of *Candida maltosa* Encodes Functionally Diverse *n*-Alkane-Inducible Cytochromes P450," *Biochemical and Biophysical Research Communications*, 1996, pp. 784-789, vol. 224, No. 3, Academic Press, Inc.

XP-002298548, "Protein Sequence," Database accession No. 355884-87-6.

\* cited by examiner

REGIO- AND ENANTIOSELECTIVE ALKANE HYDROXYLATION WITH MODIFIED CYTOCHROME P450

CROSS REFERENCE TO RELATED APPLICATIONS

This Application claims priority to U.S. Provisional Application No. 60/479,126 filed Jun. 17, 2003, herein incorporated by reference in its entirety.

STATEMENT REGARDING FEDERALLY SPONSORED RESEARCH

This invention was made with government support under Grant Number BES 9981770 awarded by National Science Foundation. The government has certain rights in the invention.

FIELD OF THE INVENTION

The invention relates to variants of cytochrome P450 enzymes that display altered and improved enantio- and regioselectivity in their hydroxylation of alkanes. The invention also relates to novel variants of cytochrome P450 enzymes that are capable of hydroxylating ethanes.

BACKGROUND

Cytochrome P450s are a large superfamily of enzymes that primarily hydroxylate substrates using dioxygen, although other redox-type reactions, including some reductions, have been reported. One variant, cytochrome P450 BM-3 is found in the bacterium *Bacillus megaterium* (EC 1.14.14.1). This variant, also known as CYP102, is a water-soluble, catalytically self-sufficient P450 containing a monooxygenase domain (64 kD) and a reductase domain (54 kD) in a single polypeptide chain (Narhi and Fulco, Journal of Biological Chemistry, 261 (16): 7160-7169 (1986) and Journal of Biological Chemistry, 262 (14): 6683-6690 (1987); Miura and Fulco, Biochimica et Biophysica ACTA, 388 (3): 305-317 (1975); Ruettinger et al., 1989). The minimum requirements for activity of the BM-3 variant are substrate, dioxygen and the cofactor nicotinamide adenine dinucleotide phosphate (NADPH). Nucleotide and amino acid sequences for P450 BM-3 can be found in, and are hereby incorporated by reference from, the GenBank database under the accession Nos. J04832 (SEQ ID NO: 1) and P14779 (SEQ ID NO: 2), respectively.

P450 BM-3 hydroxylates fatty acids of chain lengths between C12 and C18 at subterminal positions, and the regioselectivity of oxygen insertion depends on the chain length (Miura and Fulco, Biochimica et Biophysica ACTA 388 (3): 305-317 (1975); Boddupalli et al., Journal of Biological Chemistry 265 (8): 4233-4239 (1990)). The natural substrates of P450 BM-3 are hydroxylated at their ω-1, ω-2, and ω-3 positions using atmospheric dioxygen and nicotinamide adenine dinucleotide phosphate (NADPH) as shown in FIG. 1. (Ost et al., *Biochemistry*, 40, 13430-13438 (2001)). Substrate is bound and hydroxylated in a hydrophobic binding pocket that is positioned directly above a heme cofactor which is located in its own domain of the protein. A single peptide chain connects this heme domain to the reductase domain of the protein where NADPH is reduced and flavin mononucleotide (FMN) and flavin adenine dinucleotide (FAD) cofactors are used to transfer electrons to the heme active site for catalysis. The resulting products of the catalysis can be seen in FIG. 1. The hydroxylation of myristic acid by cytochrome P450 BM-3 results in 53.6% ω-1 hydroxylation product, 24.5% ω-2 hydroxylation product, and 20.0% ω-3 hydroxylation product. However, none of these substrates of P450 BM-3 are alkanes.

The optimal chain length of saturated fatty acid substrates for P450 BM-3 is 14-16 carbons, and the enzyme was initially believed to have no activity towards fatty acids smaller than C12 (Miura and Fulco, Biochimica et Biophysica ACTA, 388 (3): 305-317 (1975)). The activity of P450 BM-3 on saturated fatty acids follows the order C15=C16>C14>C17>C13>C18>C12 (Oliver et al., Biochemical Journal, 327: 537-544 Part 2 (1997)). On the C16 fatty acid, $k_{cat}=81$ s$^{-1}$ and $K_m=1.4\times10^{-6}$ M ($k_{cat}/K_m=6.0\times10^7$ M$^{-1}$s$^{-1}$). With the C12 fatty acid, $k_{cat}=26$ s$^{-1}$, $K_m=136\times0^{-6}$ M and $k_{cat}/K_m=1.9\times0^5$ M$^{-1}$s$^{-1}$ (Oliver et al., Biochemical Journal, 327: 537-544 Part 2 (1997)). P450 BM-3 is also known to hydroxylate the corresponding fatty acid amides and alcohols and forms epoxides from unsaturated fatty acids (Miura and Fulco, Biochimica et Biophysica ACTA, 388 (3): 305-317 (1975); Capdevila et al., J. Biol. Chem. 271:22663-22671 (1996); Graham-Lorence et al., J. Biol. Chem., 272:1127-1135 (1997); Ruettinger and Fulco, Journal of Biological Chemistry, 256 (11): 5728-5734 (1981)). The enzyme was reported to be inactive towards alkanes and methyl esters lacking the polar functionality of the natural substrates (Miura and Fulco, Biochimica et Biophysica ACTA, 388 (3): 305-317 (1975)). However, there were indications that P450 BM-3 could accept shorter-chain alkanes, although with very low activity (Munro et al., Biochem Soc Trans, 21 (4): 411S (1993)). However, wild type BM-3 was ineffective in its ability to hydroxylate alkanes, as the turnover of the enzyme was less than 100 total, and the rate was reported to be at 80 min$^{-1}$.

Additionally, relative to other enzymes that hydroxylate linear alkanes, wild type BM-3 was also ineffective. For example, *Pseudomonas oleovorans* is able to oxidize n-alkanes using hydroxylase machinery comprising an integral membrane oxygenase (omega-hydroxylase), a soluble NADH-dependent reductase and a soluble metalloprotein (rubredoxin) which transfers electrons from the reductase to the hydroxylase (Staijen et al., European Journal of Biochemistry, 267 (7): 1957-1965 (2000)). The omega-hydroxylase has been cloned from *P. oleovorans* into *E. coli*, where it has been expressed and purified (Shanklin et al., Proceedings of the National Academy of Sciences of the United States of America, 94 (7): 2981-2986 (1997)). The specific activity of this omega-hydroxylase for octane (5.2 units/mg hydroxylase (Shanklin et al., Proceedings of the National Academy of Sciences of the United States of America, 94 (7): 2981-2986 (1997)) is about 13 times greater than that of P450 BM-3 (0.4 units/mg enzyme). (The specific activity of the complete *P. oleovorans* system, including the rubredoxin and the reductase, is less than 5.2 units/mg). Thus, wildtype P450 BM-3 was inefficient relative to this (and other) naturally occurring enzymes for alkane hydroxylation.

While the wild-type P450 was found to be ineffective in alkane hydroxylation, this inefficiency has been overcome in previous work by one of the Inventors. In this work, directed evolution was used to convert wild type BM-3 into a fast, but non-selective, alkane hydroxylase, dubbed "139-3." (Farinas et al., *Adv. Synth. Catal.*, 343, 601-606 (2001); Glieder et al., *Nature Biotech.*, 20, 1135-1139 (2002)). The P450 139-3 was found to have an increased oxidation activity towards alkanes, and was found to be active on alkanes as small as propane. In comparison to the P450 BM-3, the evolved 139-3 protein has 11 amino acid substitutions in its heme domain.

SUMMARY

Cytochrome P450 BM-3 from *Bacillus megaterium* was engineered using a combination of directed evolution and site-directed mutagenesis to hydroxylate linear alkanes regio- and enantioselectively using atmospheric dioxygen as an oxidant. Mutant 9-10A-A328V hydroxylates octane primarily at the 2-positio to form S-2-octanol (40% ee). Another mutant, 1-12G, hydroxylates alkanes larger than hexane primarily at the 2-position, but forms R-2-alcohols (40-55% ee). These biocatalysts are highly active for alkane substrates and support thousands of product turnovers. These regio- and enantio-selectivities are retained in whole-cell biotransformations with *E. coli*, where the engineered P450s can be expressed at high levels and the expensive cofactor is supplied endogenously.

One embodiment is an isolated mutant P450 enzyme with a first mutation that allows the mutant P450 enzyme to hydroxylate an alkane to produce a first product with a first hydroxylation profile. Without the mutation, the enzyme would hydroxylate an alkane to produce a second product with a different hydroxylation profile.

In another embodiment a method of making a mutant P450 enzyme having altered selective hydroxylation abilities is provided. The method involves providing a first mutant P450 that is capable of alkane hydroxylation of a substrate to produce a product with a first hydroxylation profile, and modifying at least one amino acid in the first mutant P450 to produce a second mutant P450, wherein said second mutant P450 is capable of alkane hydroxylation of the substrate to produce a product with a second hydroxylation profile.

In another embodiment, a method of making a P450 enzyme with regioselective alkane hydroxylation activity is provided. The method involves selecting residues to alter to reduce the volume of the active site of a P450 enzyme, replacing small hydrophobic residues in the active site with larger hydrophobic residues to create a mutant P450, testing the resulting mutant P450 for regioselectivity, and repeating the steps if no such P450 mutant is made. These steps result in the creation of a P450 enzyme with regioselective alkane hydroxylation activity.

In another embodiment, a method of making a P450 enzyme with enantioselective alkane hydroxylation activity is provided. The method involves selecting residues to alter to reduce the volume of the active site of a P450 enzyme, replacing small hydrophobic residues in the active site with larger hydrophobic residues to create a mutant P450, testing the resulting mutant P450 for enantioselectivity, and repeating the steps if no such P450 mutant is made. These steps result in the creation of a P450 enzyme with enantioselective alkane hydroxylation activity.

In another embodiment, a method for making a P450 enzyme with alkane hydroxylation activity towards ethane is provided. The method involves selecting residues to alter to reduce the volume of the active site of a P450 enzyme, replacing small hydrophobic residues in the active site with larger hydrophobic residues to create a mutant P450, testing the resulting mutant P450 for ethane hydroxylation activity, and repeating the steps if no such P450 mutant is made. These steps result in the creation of a P450 enzyme with ethane hydroxylation activity.

In another embodiment, an isolated nucleic acid encoding a cytochrome P450 mutant that has a higher capability than the corresponding wild-type cytochrome P450 to oxidize at least one substrate selected from an alkane comprising a carbon-chain of no more than 8 carbons is provided. The wild-type cytochrome P450 comprises an amino acid sequence identical to SEQ ID NO: 2, and the cytochrome P450 mutant is at least 80% identical to the sequence in SEQ ID NO: 2. The mutant P450 has an amino acid substitution at a residue corresponding to a core residue selected from V78, H236, and E252. Additionally, the mutant has an amino acid substitution at a residue corresponding to a selective hydrolysis residue of SEQ ID NO: 2 selected from R47C, A82L, K94I, P142S, C205V, S226R, A290V, and A328V.

In another embodiment, a method of creating a regio- and enantioselective hydroxylation P450 is provided. The method involves performing directed evolution on a P450 to obtain a mutant P450, and modifying an active site of said mutant P450 so as to reduce the size of the active site of the mutant P450. This results in the creation of a regio- and enantioselective hydroxylation P450.

In another embodiment, an isolated mutant P450 enzyme with regioselective alkane hydroxylation activity that has a higher degree of regiospecificity for the hydroxylation of octane than the wild-type and 139-3 mutant is provided.

In another embodiment, an isolated mutant P450 enzyme that predominantly hydroxylates a substrate at a first position, having an altered enantiospecificity for alkanes, is provided. The mutant P450 enzyme comprises a selective hydroxylation mutation which allows the mutant P450 enzyme with the selective hydroxylation mutation to predominantly hydroxylate the substrate at a second position.

In another embodiment, a method of hydroxylating an alkane in a selective manner is provided. The method involves providing an isolated mutant P450 enzyme that has selective hydroxylation activity towards an alkane, and contacting the isolated mutant P450 with said alkane. This allows the isolated mutant P450 hydroxylates said alkane in a selective manner.

DETAILED DESCRIPTION

Figure 1:
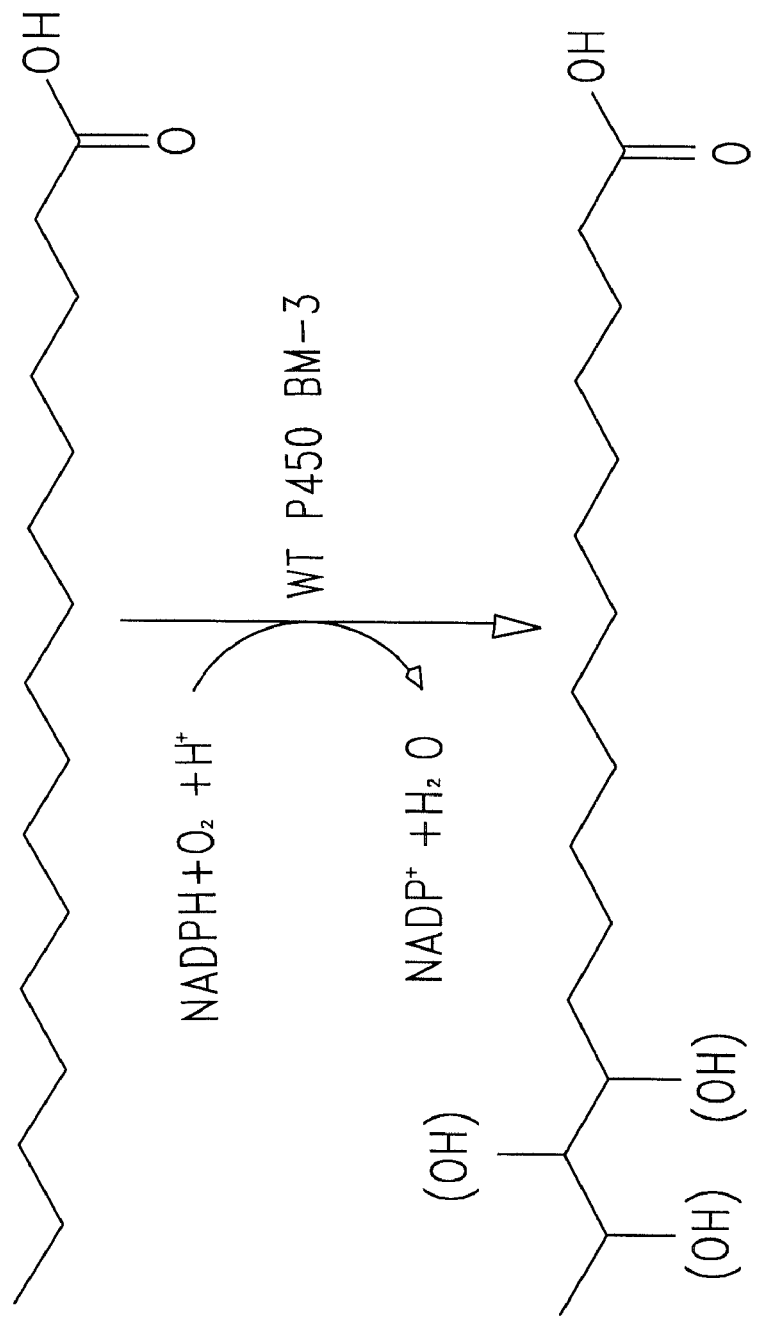
FIG. 1 is an illustration of a prior art general hydroxylation reaction of myristic acid catalyzed by cytochrome P450s.
Figure 2A:
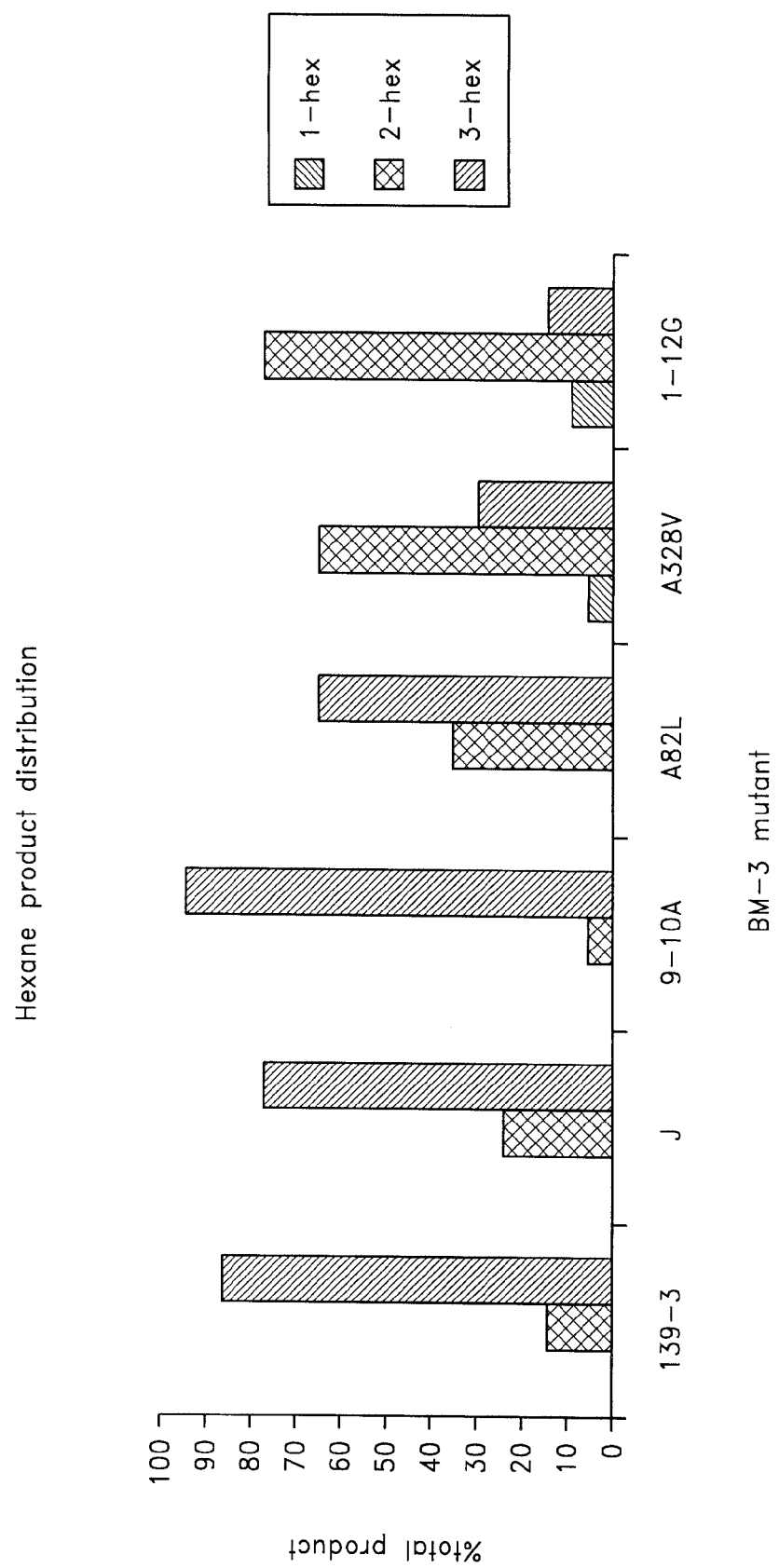
FIG. 2A is a bar graph displaying the products of hexane catalysis of various BM-3 mutants.
Figure 2B:
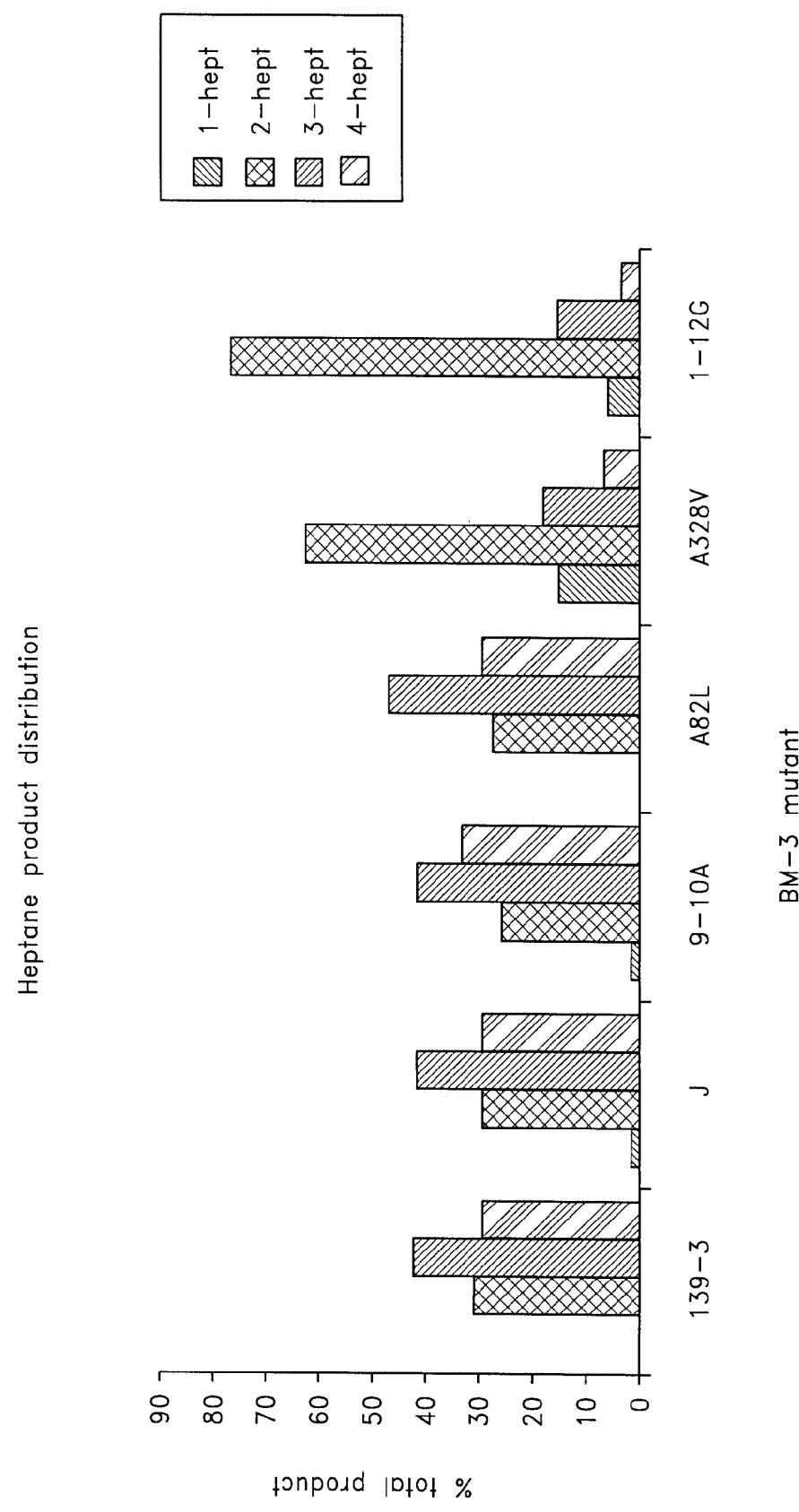
FIG. 2B is a bar graph displaying the products of heptane catalysis of various BM-3 mutants.
Figure 2C:
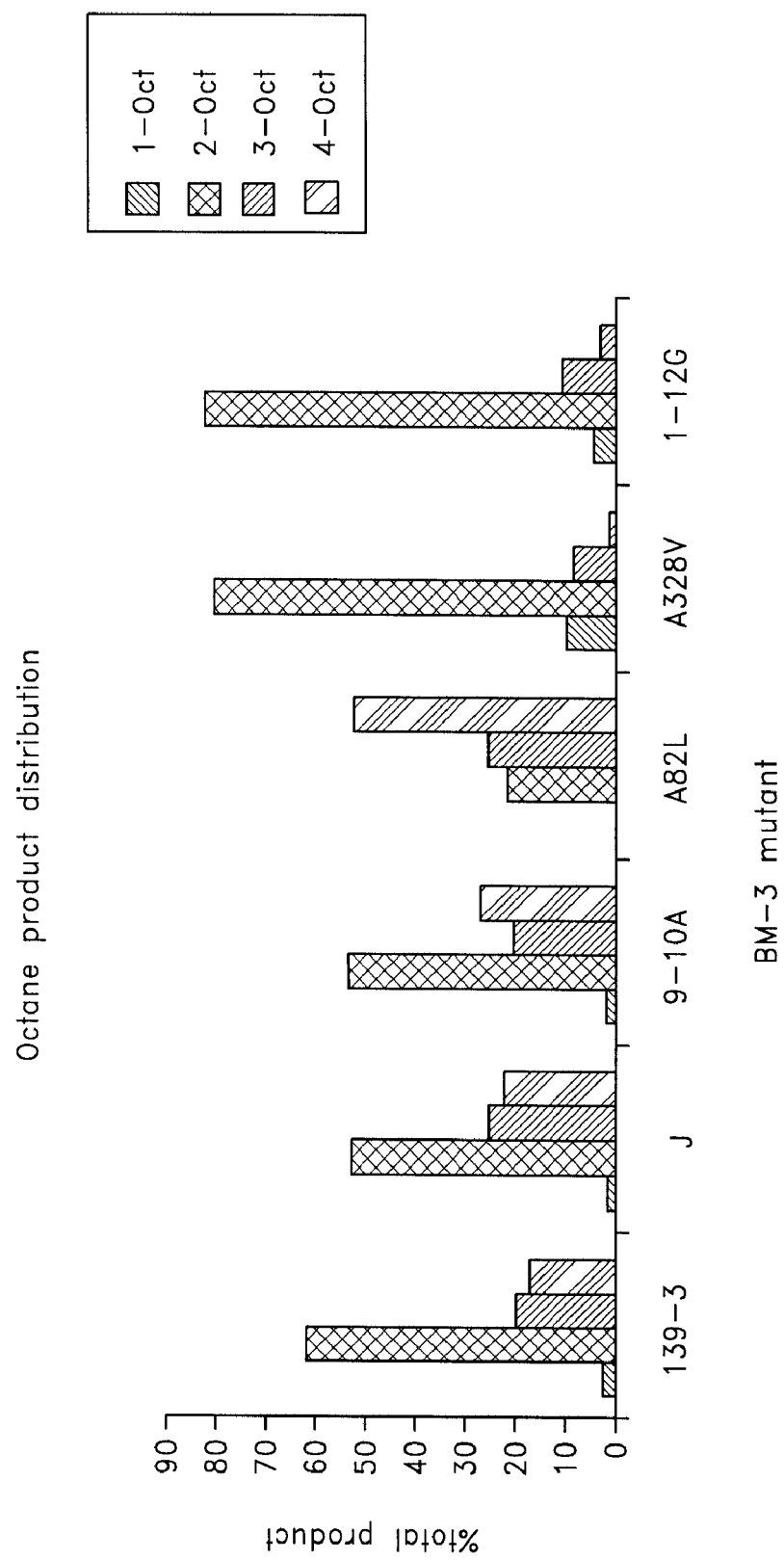
FIG. 2C is a bar graph displaying the products of octane catalysis of various BM-3 mutants.
Figure 2D:
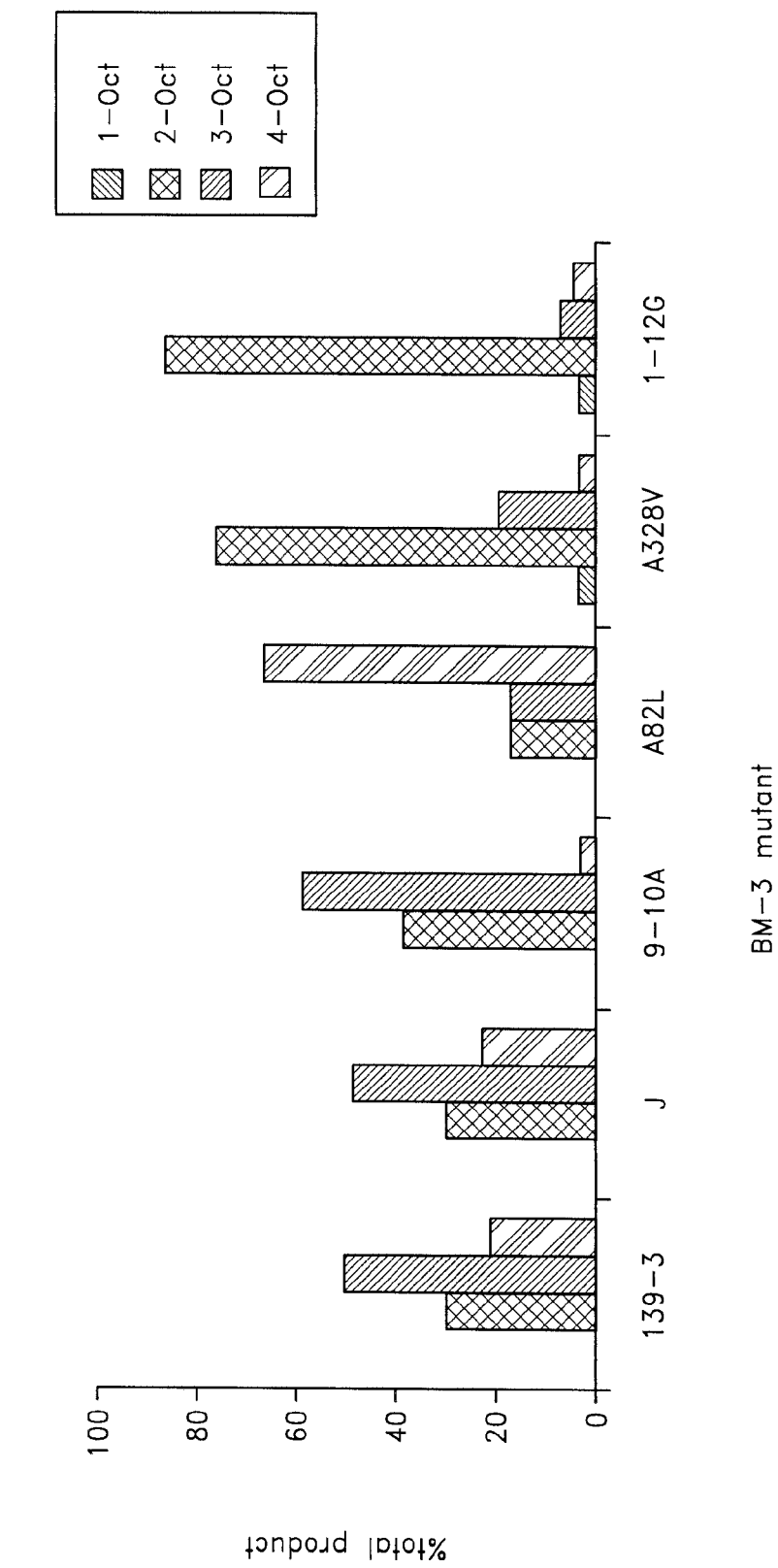
FIG. 2D is a bar graph displaying the products of nonane catalysis of various BM-3 mutants.
Figure 2E:
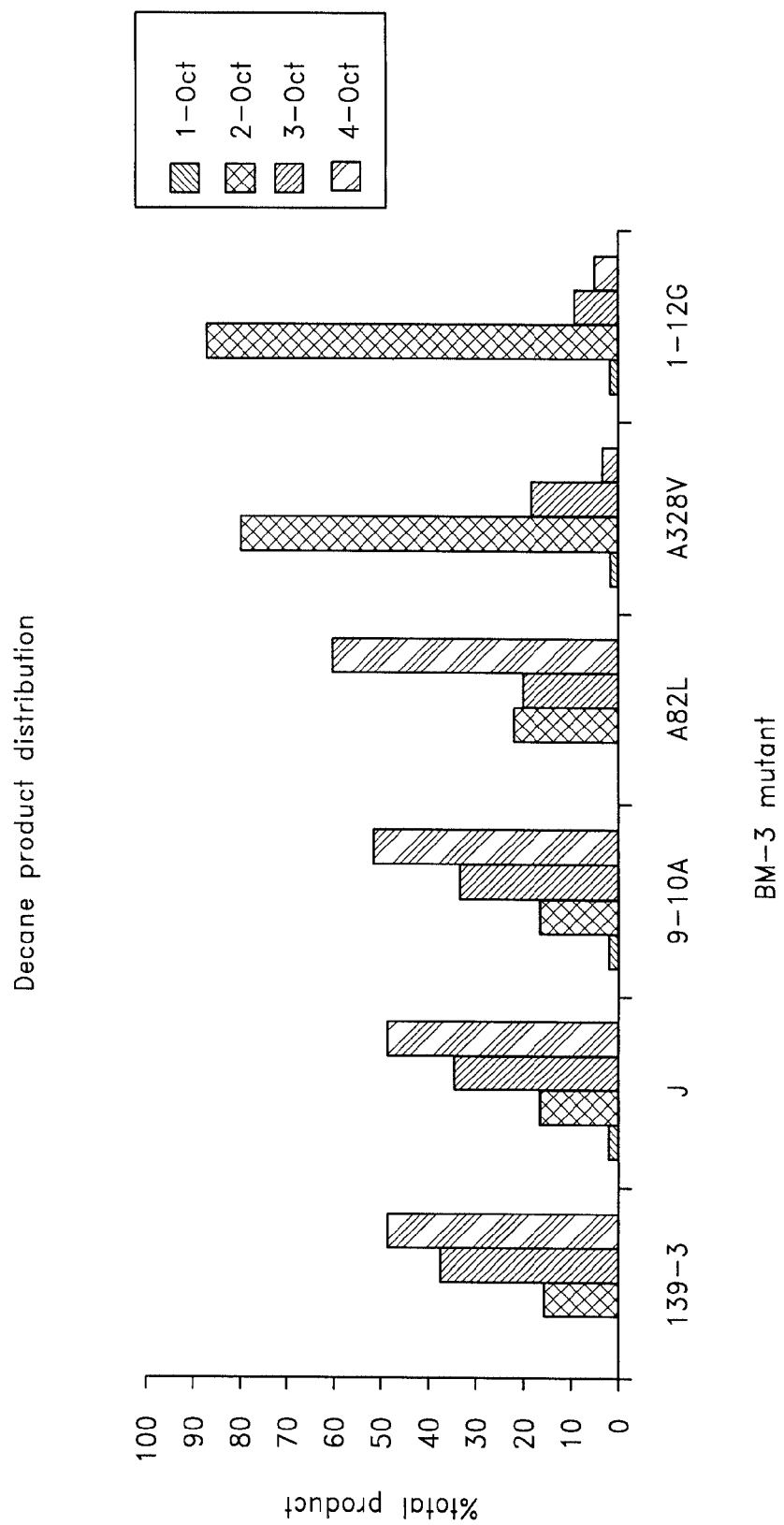
FIG. 2E is a bar graph displaying the products of decane catalysis of various BM-3 mutants.

Embodiments of the invention include mutant and altered forms of cytochrome P450 proteins. In one embodiment, mutants of cytochrome P450 BM-3 from *Bacillus megaterium* were engineered using an initial mutant P450 and a combination of directed evolution and site-directed mutagenesis, as discussed more completely below. The starting mutant was a P450 enzyme with 11 mutations that allowed it to hydroxylate alkanes to produce certain amounts of particular enantiomeric and regiospecific alkane products. The starting mutant was then engineered to display altered regio- and enantioselectivity towards various substrates (e.g., the new mutants have an altered hydroxylation profile). The resulting enzymes were found to be capable of hydroxylating linear alkanes in an altered regio- and enantioselective manners. The turnover number was high. Each of the resulting P450 mutants produced regio- and enantiomeric products in different amounts. Simply put, the products of the initial P450 mutant were hydroxylated at particular positions in particular amounts, and the products of the new P450 mutants were hydroxylated at these particular positions, or in novel positions, in different amounts. Thus, by choosing the proper mutant enzyme, with these described characteristics, one can regio- and enantioselectively hydroxylate substrates in a desired manner. This provides tremendous benefits for specifically hydroxylating target substrates in a predefined manner.

Embodiments of the invention include mutant P450s with regio- and/or enantioselectivity. For example, one mutant P450, 9-10A-A328V, was found to hydroxylate octane primarily at the 2-position to form S-2-octanol (40% ee). Another mutant P450, 1-12G, was found to hydroxylate alkanes larger than hexane primarily at the 2-position, but also formed R-2-alcohols (40-55% ee). These two mutants were discovered to have enhanced and altered regio- and enantiospecificity compared to other P450 enzymes, including the original 139-3 mutant from which they were derived.

Embodiments of the invention further include mutant P450s that are capable of hydroxylating substrates as small as ethane. For example, one of the discovered mutants, termed "1-12G" was advantageously found capable of hydroxylating ethane as a substrate.

Another embodiment of the invention includes regio-and enantioselective enzymes that are retained in whole-cell biotransformations with *E. coli*, where the engineered P450 enzymes are expressed at high levels, and the required cofactor is supplied endogenously.

Other embodiments of the invention include methods of using these mutants for the selective hydroxylation of alkanes to product well characterized products in known quantities. As the mutant enzymes produce known products in a known amount, all that is required to create a desired product is to select an appropriate mutant P450 enzyme that catalyzes a reaction to produce a desired enantio- or regiospecific product and then apply the substrate to the enzyme under conditions which allow for catalysis. Methods of selecting and isolating the desired product from the products created are also known and disclosed herein.

Embodiments of the invention also include methods of creating mutant P450s that are capable of hydroxylating alkanes in a regio- and enantioselective manner.

DEFINITIONS

Unless defined otherwise herein, all technical and scientific terms used herein have the same meaning as commonly understood by one of ordinary skill in the art to which this invention belongs. Singleton et al. (2001) Dictionary of Microbiology and Molecular Biology, third edition, John Wiley and Sons (New York), and Hale and Marham (1991) The Harper Collins Dictionary of Biology, Harper Perennial, N.Y. provide one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "identical" in the context of two nucleic acid or polypeptide sequences refers to the residues in the two sequences which are the same when aligned for maximum correspondence over a specified comparison window. When percentage of sequence identity is used in reference to proteins or peptides it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11-17 (1988) e.g., as implemented in the program PC/GENE (Intelligenetics, Mountain View, Calif., USA).

A "mutant" form of a protein or DNA molecule is a form that is altered from its wild-type composition. Mutant proteins typically have amino acid substitutions at one or more positions. Mutant DNA molecules typically have nucleotide substitutions in one or more positions. Mutant forms of a protein or DNA molecule can have the same, or altered, functions in comparison to the wild-type. For ease of discussion, mutants may be referred to by their variation from the single amino acid code from which the mutation arose. For example, in one format the mutant is referred to as XPOSY, where "X" refers to the single letter code of the amino acid in the original sequence, "POS" refers to the position of the mutation in the sequence, and Y refers to the single letter code for the new amino acid appearing at the mutation's position. For example, V175I would mean that in the original protein, the amino acid at position 175 is a valine ("V"), but in the mutant, the valine is replaced with an isoleucine ("I").

As used herein, a "core mutation" is a mutation of a wild-type cytochrome P450 protein that provides the protein with enhanced alkane hydroxylase activity. In one embodiment, the cytochrome P450 protein is a P450 BM-3 protein. It should be realized that any mutation, or set of mutations, that enhance the ability of a cytochrome P450 protein to hydroxylate alkanes are considered core mutations.

A "core mutant" is a cytochrome P450 protein that has been altered to contain one or more core mutations. In one embodiment, a core mutant is the cytochrome P450 139-3 protein which was derived from mutations of P450 BM-3, and includes V78A, H138Y, T175I, V178I, A184V, H236Q, E252G, R255S, A295T, and L353V core mutations. In one embodiment, those mutations that revert the amino acid sequence back to the wild type sequence for the selective hydroxylation mutations are not considered core mutations. Examples of which are H138, V178, and A295. Thus, in one embodiment, when the core mutations are combined with a selective mutation, the core mutations will consist of V78A, T175I, A184V, H236Q, E252G, R255S, and L353V.

As used herein, the terms "selective hydroxylation mutations" or "selective mutations" are used interchangeably and refer to mutations that provide a P450 protein with altered regio- or enantio-selectivity towards substrates. A protein having such mutations is termed a "selective hydroxylation mutant" or a "selective mutant". In one embodiment, the target substrate of such mutants is an alkane. Examples of types or categories of selective hydroxylation mutants are discussed below, particularly in Tables 1-4. The selective hydroxylation mutations may simply alter the selectivity of the P450 towards a single substrate, or across many substrates. The selective mutation may alter both the selectivity and increase the functional ability of the enzyme, so that more regio or enantioselective end product is produced.

Non-limiting general examples of selective hydroxylation mutations include cytochrome P450 139-3 proteins having one or more of the following additional mutations: A328V, L75I, F87I and A82L. Non-limiting examples of selective hydroxylation mutants showing altered or enhanced regioselective hydroxylation include cytochrome P450 139-3 proteins having one or more of the following additional mutations: A82I, and T260L. Examples of altered and enhanced regioselective and enantioselective mutants of cytochrome P450 139-3 can be found within Tables 1-4 and FIGS. 2A-2E.

In some embodiments, more than a single mutation may be required in order for the desired result to occur, in such situations, each of the required mutations will be considered as either core, selective, or both, as appropriate. Mutants may also be both enantioselective and regioselective.

An enzyme is "regioselective" if the product that results from the enzymatic reaction is positioned in an altered position. In one embodiment, the enzyme is an alkane hydroxylase and the hydroxylation reaction results in a hydroxyl group positioned in an altered position. This means that while the original P450 may have created a first amount of product A and a second amount of product B, the regioselective enzyme could produce a third amount of product A and a fourth amount of product B. Thus, while the initial 139-3 mutant could be considered regioselective for particular substrates, the regioselective mutants described herein display different regioselectivity from the 139-3 mutant. In one embodiment, the product of a regioselective hydroxylase contains a hydroxy group at the 2 position predominantly, rather than the 1 or the 3 position. In another embodiment, a distribution of hydroxyl groups in the final product that differs from the product of the wild-type enzyme is sufficient to demonstrate that the enzyme is regioselective. In another embodiment, an increase of 1, 1-2, 2-5, 5-10, 10-20, 20-30, 30-40, 40-50, 50-60, 60-70, 70-80, 80-90, 90-100, 100-200, 200-500 percent or more in the concentration of one product over another product is sufficient to demonstrate that the enzyme is regioselective. In one embodiment, an enzyme is regioselective when its selectivity is greater than the wild-type or 139-3 mutant P450 regioselectivity as shown in Table 2.

An enzyme is enantioselective if the hydroxylation reaction of the enzyme results in a high amount of one particular enantiomeric product compared to other possible enantiomeric products. An enzyme that has an altered enantioselectivity means that while the original P450 may have created a first amount of enantiomeric product A and a second amount of enantiomeric product B, the enantioselective enzyme could produce a third amount of enantiomeric product A and a fourth amount of enantiomeric product B. Thus, while the initial 139-3 mutant could be considered enantioselective for particular substrates, the enantioselective mutants described herein display different enantioselectivity from the 139-3 mutant. In one embodiment, the enzyme is a mutant form of the wild-type P450 BM-3 enzyme. In another embodiment, the enzyme is a mutant of cytochrome P450 139-3 enzyme. In one embodiment, the positioning of a hydroxy group in the final product is predominantly at the 2 S position. In another embodiment, the positioning of the hydroxy group in the final product is at the 2 R position predominantly. In yet another embodiment, the distribution of positions in the final product is different from the wild type enzyme in a quantity sufficient to demonstrate that the enzyme is differently enantioselective. In another embodiment, an increase of 1, 1-2, 2-5, 5-10, 10-20, 20-30, 30-40, 40-50, 50-60, 60-70, 70-80, 80-90, 90-100, 100-200, 200-500, or more in the concentration of one product over another product is sufficient to demonstrate that the enzyme is enantioselective.

In one embodiment, the regioselective and enantioselective mutations are so characterized because of their activity to particular lengths of alkane substrate. In another embodiment, the regio- and enantioselective mutations display improved specificity compared to the 139-3 mutant, either in general or for a particular substrate. For example, while the 139-3 mutation may be regioselective for octanes (61% produced as a 2-alcohol), it is not as regioselective as the 9-10A-A328V mutant (80%) or 1-12G mutant (82%) as described in more detail below. Thus, the terms can be terms of degree, in some embodiments. In one embodiment, any increase in selectivity, either enantio-, regio-, or both, is sufficient as long as it is a measurable increase. For example, it may increase by 1, 1-5, 5-10, 10-20, 20-25, 25-30, 30-32, 32-40, 40-50, 50-100, 100-500 percent, or more, over the wild-type or over the 139-3 BM-3 mutant. Alternatively, the regio- or enantioselectivity may only apply as an absolute; thus, an enzyme will only be regio- or enantioselective if the resulting mutant has a regio- or enantioselectivity where the 139-3 or wild-type BM-3 had none. This could happen in at least two ways. Either the selectivity of the 139-3 mutant is effectively random, or the mutant BM-3 is active on a new substrate, and thus any selectivity would be more than the initial amount of selectivity of zero. The level of activity is also important. Even though the wild type P450 may display a negligible amount of activity on alkanes, such activity, and any resulting regio- or enantioselectivity from the enzyme would not qualify the wild type P450 BM-3 as a regio- or enantioselective P450. This is because some effective, or substantial level of activity of the P450 on alkanes is still required. Such substantial or effective levels are discussed below; however, the wild type rate of catalysis in light of the total turnover is not substantial.

A "consistent" selective mutant is a selective mutant that displays a consistent bias of selectivity of product produced for more than one starting substrate. Thus, for example, the mutant 9-10A-A328V, discussed below, is a consistent regioselective mutant for hexane, heptane, octane, nonane, and decane, as the products from hexane, heptane, octane, nonane, and decane all result predominantly in the 2-alcohol. In contrast, the 139-3 mutant results in more of the 3-alcohol for heptane substrates, but more of the 2-alcohol for the octane substrate. Thus, in one embodiment, a mutant P450 is a consistent regioselective enzyme if the largest amount of product produced from hexane, heptane and octane is the 2-alcohol. In one embodiment, the majority of each of the products is made at the same position.

An mutant enzyme or protein is "improved" if its activity is altered or enhanced from its parent composition. For example, an improved P450 139-3 protein is one that contains mutations and also exhibits regioselectivity, across substrates, or for an individual substrate, at a level that is above the regio- or enantioselectivity of the P450 139-3 protein. In one embodiment, the improved activity is for a particular substrate, such as ethane, propane, hexane, heptane, octane, nonane, and/or, decane. In one embodiment, the improved regio- or enantioselectivity provides the mutant with the ability to more effectively produce regio-selective products. For example, an increase of 1, 1-5, 5-10, 10-15, 15-100, 100-300, or more percent more effective than the wild-type or 139-3 mutant in converting the substrate to a single product is an improved regio- or enantiospecific enzyme. Definitions and distinctions between the 139-3 mutant and the mutants described herein can be found in Tables 2, 3, and 4.

Another form of an "improved" mutant is one that effectively has a greater ability to efficiently produce a regio- or enantiospecific product. Thus, while the percentage of each product may not be very high, the efficiency of the formation of the products is great enough so that the desired product can be made in substantial amounts. Thus, while a wild type P450 BM-3 may have a product distribution of 17% 2-octanol, 40% 3-octanol, and 43% 4-octanol, it may have a relatively slow catalytic rate of 80 min$^{-1}$ and less than about 100 total turnovers. Improved mutants include those enzymes that have a higher catalytic rate, and/or higher turnover than the unimproved enzyme.

"Predominant" denotes the species of product that is the largest percent of the products made. Thus, given 4 products, three of which are equal, the fourth, if greater than the other three would be the predominant product.

A "hydroxylation profile" of a product is a description of the number and position of hydroxyl groups in the product. Thus, for example, an alkane hydroxylase enzyme typically creates products having a defined hydroxylation profile, such that hydroxyl groups are placed at certain positions on particular percentages of the final reaction products. Altering or modifying the hydroxylation profile of a product means changing the positions, or proportions, of hydroxyl groups in the final reaction products. In another example, all of the products listed in Table 2 are used for the members of hydroxylation profile. For example, 1-alcohol, 2-alcohol, 3-alcohol, 4-alcohol and ketones may make up the hydroxylation profile. Thus, Table 2 denotes the hydroxylation profiles of each of the mutants for substrates hexane through decane, in this embodiment. A "variant" is distinguished from a mutant. A variant P450 has at least one amino acid or nucleic acid difference from the wild-type P450. A "variant" of a P450 mutant typically contains all of the mutant positions, plus additional changes in the amino or nucleic acid sequence. Thus, while the description "variant" will encompass sequences with changes, a variant of a P450 mutant will still maintain the amino acid or nucleotide changes that define the P450 mutant. For examples, a protein that has one or more core mutations along with additional changes in its DNA or protein sequence is a "variant" core mutant. Similarly, a protein that has one or more selectivity mutations along with additional changes in its DNA or protein sequence is a "variant" selectivity mutant. Variant P450s can vary in the number and the types of residue replacements. In one embodiment, a variant is any amino acid sequence that is 100-99, 99-98, 98-95, 95-90, 90-80, 80-70, 70-60, 60-50, or 50-30 percent identical to its original amino acid sequence. In another embodiment, a variant is any amino acid sequence that is 100-99, 99-98, 98-95, 95-90, 90-80, 80-70, 70-60, 60-50, or 50-30 percent similar to the amino acid sequence of BM-3 P450. In another embodiment, a variant is any amino acid sequence that is 100-99, 99-98, 98-95, 95-90, 90-80, 80-70, 70-60, 60-50, or 50-30 percent similar to the amino acid sequence of cytochrome P450 139-3. In another embodiment the sequence of comparison is a consensus sequence of known BM-3 proteins. These can apply, as appropriate, to both the amino acid sequence and nucleic acid sequences. In another embodiment, a variant is a nucleic acid sequence that is capable of hybridizing to the disclosed BM-3 sequence under highly stringent or moderately stringent conditions. Highly stringent conditions are those that are at least as stringent as, for example, 4×SSC at 65° C., or 4×SSC and 50% formamide at 42° C.

Figure 4:
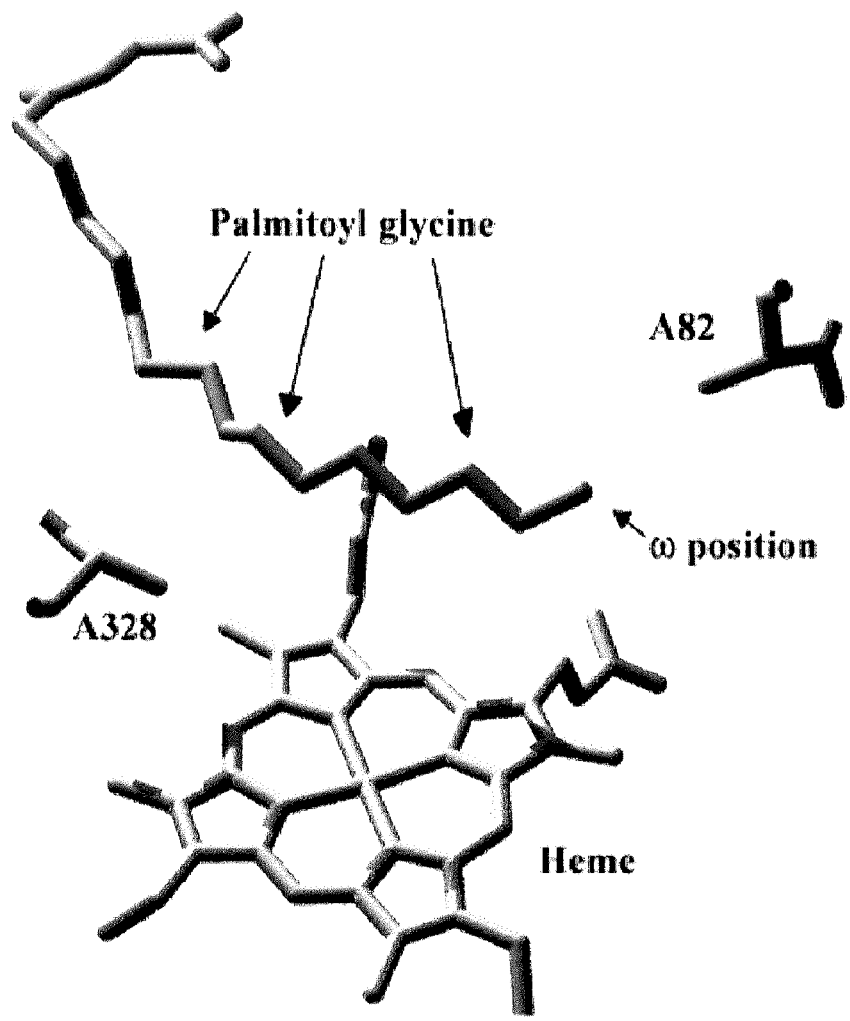
FIG. 4 is an illustration of A328 and A82 in the active site of wild type cytochrome P450 BM-3.

The "active site" of the enzyme includes those residues which interact with the substrate in the binding and catalysis of the substrate. As appreciated by one of skill in the art, the precise residues involved in the active site may vary according to the substrate. The active site may be defined through mutagenesis studies or through protein structures which will reveal which part of the enzyme is most closely interacting with the substrate. In one embodiment, the active site is defined as those residues within a certain distance of the bound substrate or where the bound substrate would be positioned. For example, residues within 0-1, 1-2, 2-4, 4-5, 5-6, 6-7, 7-8, or 8-10 angstroms of the bound substrate, or the points at which the substrate will bind, are part of the active site. In another embodiment, the active site includes those residues within a certain distance of the heme group. For example, residues within 0-1, 1-2, 2-4, 4-5, 5-6, 6-7, 7-8, or 8-10 angstroms of the heme group, in the substrate bound or substrate free conformation, are part of the active site. In one embodiment, the active site is defined by the herein discussed crystal structures. In another embodiment, the active site includes the residues or mutants discussed herein which resulted in changes in activity of the P450 enzyme, consistent with a mutation in an active site. In one embodiment, the amino acids of the active site includes the amino acids at positions 75, 78, 82, 87, 88, 260, 328 of CYP102A1, or equivalent positions in variant proteins. In one embodiment, the area of the active site, but not all of the residues, is shown in FIG. 4. Amino acid A 328 is shown on the left, and A82 is displayed in the upper right. Palmitoyl glycine is displayed above the heme and between the two residues.

An alkane is typically defined as a non-aromatic saturated hydrocarbon with the sequence of CnH(2n+2). For the purposes of this application and determining whether or not an enzyme is active with a particular substrate, an "alkane" does not encompass fatty acids that are the traditional targets for P450s.

The proteins of the present invention further include "conservative amino acid substitution variants" (i.e., conservative) of the proteins herein described. As used herein, a conservative variant refers to at least one alteration in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can often be altered, for example to render the peptide more hydrophobic or hydrophilic, without adversely affecting the biological activities of the protein.

The proteins of the present invention are preferably in isolated form. As used herein, a protein is said to be isolated when physical, mechanical or chemical methods are employed to remove the protein from cellular constituents that are normally associated with the protein. A skilled artisan can readily employ standard purification methods to obtain an isolated protein.

Homology or identity at the amino acid or nucleotide level is determined by BLAST (Basic Local Alignment Search Tool) analysis using the algorithm employed by the programs blastp, blastn, blastx, tblastn and tblastx (Karlin et al., (1990) Proc. Natl. Acad. Sci. USA 87, 2264-2268 and Altschul, (1993) J. Mol. Evol. 36, 290-300, fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases (see Altschul et al., (1994) Nature Genetics 6, 119-129 which is fully incorporated by reference). The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89, 10915-10919, fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively.

"Stringent conditions" are those that (1) employ low ionic strength and high temperature for washing, for example, 0.5 M sodium phosphate buffer at pH 7.2, 1 mM EDTA at pH 8.0 in 7% SDS at either 65° C. or 55° C., or (2) employ during hybridization a denaturing agent such as formamide, for example, 50% formamide with 0.1% bovine serum albumin, 0.1% Ficoll, 0.1% polyvinylpyrrolidone, 0.05 M sodium phosphate buffer at pH 6.5 with 0.75 M NaCl, 0.075 M sodium citrate at 42° C. Another example is use of 50% formamide, 5.times.SSC (0.75 M NaCl, 0.075 M sodium citrate), 50 mM sodium phosphate at pH 6.8, 0.1% sodium pyrophosphate, 5× Denhardt's solution, sonicated salmon sperm DNA (50 μg/ml), 0.1% SDS and 10% dextran sulfate at 55° C., with washes at 55° C. in 0.2×.SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid encoding other polypeptides from the source of nucleic acid.

Embodiments of the present invention further include fragments of any one of the encoding nucleic acids molecules. As used herein, a fragment of an encoding nucleic acid molecule refers to a small portion of the entire protein coding sequence.

The size of the fragment will be determined by the intended use. For example, if the fragment is chosen so as to encode an active portion of the protein, the fragment will need to be large enough to encode the functional region(s) of the protein. For instance, fragments of the invention include fragments of DNA encoding mutant P450 BM-3 proteins that maintain altered or enhanced enantioselectivity and regioselectivity.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, fluorescent-labeled, biotin-labeled, radio-labeled nucleotides and the like. A skilled artisan can employ any of the art known labels to obtain a labeled encoding nucleic acid molecule.

A. Directed Evolution in General

One technique to improve the alkane-oxidation ability of wild-type or parent cytochrome P450 enzymes, including P450 BM-3, is directed evolution. General methods for generating libraries and isolating and identifying improved proteins according to the invention using directed evolution are described briefly below. More extensive descriptions can be found in, for example, Arnold (Accounts of Chemical Research, 31(3): 125-131 (1998)); U.S. Pat. Nos. 5,741,691; 5,811,238; 5,605,793 and 5,830,721; and International Applications WO 98/42832, WO 95/22625, WO 97/20078, WO 95/41653 and WO 98/27230.

The basic steps in directed evolution are (1) the generation of mutant libraries of polynucleotides from a parent or wild-type sequence; (2)(optionally) expression of the mutant polynucleotides to create a mutant polypeptide library; (3) screening/selecting the polynucleotide or polypeptide library for a desired property of a polynucleotide or polypeptide; and (4) selecting mutants which possess a higher level of the desired property; and (5) repeating steps (1) to (5) using the selected mutant(s) as parent(s) until one or more mutants displaying a sufficient level of the desired activity have been obtained. The property can be, but is not limited to, alkane oxidation capability and enantio- and regiospecificity.

The parent protein or enzyme to be evolved can be a wild-type protein or enzyme, or a variant or mutant. The parent polynucleotide can be retrieved from any suitable commercial or non-commercial source. The parent polynucleotide can correspond to a full-length gene or a partial gene, and may be of various lengths. Preferably the parent polynucleotide is from 50 to 50,000 base pairs. It is contemplated that entire vectors containing the nucleic acid encoding the parent protein of interest may be used in the methods of this invention.

Any method can be used for generating mutations in the parent polynucleotide sequence to provide a library of evolved polynucleotides, including error-prone polymerase chain reaction, cassette mutagenesis (in which the specific region optimized is replaced with a synthetically mutagenized oligonucleotide), oligonucleotide-directed mutagenesis, parallel PCR (which uses a large number of different PCR reactions that occur in parallel in the same vessel, such that the product of one reaction primes the product of another reaction), random mutagenesis (e.g., by random fragmentation and reassembly of the fragments by mutual priming); site-specific mutations (introduced into long sequences by random fragmentation of the template followed by reassembly of the fragments in the presence of mutagenic oligonucleotides); parallel PCR (e.g., recombination on a pool of DNA sequences); sexual PCR; and chemical mutagenesis (e.g., by sodium bisulfite, nitrous acid, hydroxylamine, hydrazine, formic acid, or by adding nitrosoguanidine, 5-bromouracil, 2-aminopurine, and acridine to the PCR reaction in place of the nucleotide precursor; or by adding intercalating agents such as proflavine, acriflavine, quinacrine); irradiation (X-rays or ultraviolet light, and/or subjecting the polynucleotide to propagation in a host cell that is deficient in normal DNA damage repair function); or DNA shuffling (e.g., in vitro or in vivo homologous recombination of pools of nucleic acid fragments or polynucleotides). Any one of these techniques can also be employed under low-fidelity polymerization conditions to introduce a low level of point mutations randomly over a long sequence, or to mutagenize a mixture of fragments of unknown sequence.

Once the evolved polynucleotide molecules are generated they can be cloned into a suitable vector selected by the skilled artisan according to methods well known in the art. If a mixed population of the specific nucleic acid sequence is cloned into a vector it can be clonally amplified by inserting each vector into a host cell and allowing the host cell to amplify the vector and/or express the mutant or variant protein or enzyme sequence. Any one of the well-known procedures for inserting expression vectors into a cell for expression of a given peptide or protein may be utilized. Suitable vectors include plasmids and viruses, particularly those known to be compatible with host cells that express oxidation enzymes or oxygenases. E. coli is one exemplary preferred host cell. Other exemplary cells include other bacterial cells such as Bacillus and Pseudomonas, archaebacteria, yeast cells such as Saccharomyces cerevisiae, insect cells and filamentous fungi such as any species of Aspergillus cells. For some applications, plant, human, mammalian or other animal cells may be preferred. Suitable host cells may be transformed, transfected or infected as appropriate by any suitable method including electroporation, CaCl.sub.2 mediated DNA uptake, fungal infection, microinjection, microprojectile transformation, viral infection, or other established methods.

The mixed population of polynucleotides or proteins may then be tested or screened to identify the recombinant polynucleotide or protein having a higher level of the desired activity or property. The mutation/screening steps can then be repeated until the selected mutant(s) display a sufficient level of the desired activity or property. Briefly, after the sufficient level has been achieved, each selected protein or enzyme can be readily isolated and purified from the expression system, or media, if secreted. It can then be subjected to assays designed to further test functional activity of the particular protein or enzyme. Such experiments for various proteins are well known in the art, and are described below and in the Examples below.

The evolved enzymes can be used in biocatalytic processes for, e.g., alkane hydroxylation. The enzyme mutants can be used in biocatalytic processes for production of chemicals from hydrocarbons. Furthermore, the enzyme mutants can be used in live cells or in dead cells, or it can be partially purified from the cells. One preferred process would be to use the enzyme mutants in any of these forms (except live cells) in an organic solvent, in liquid or even gas phase, or for example in a super-critical fluid like $CO_2$. The organic solvent would dissolve high concentrations of the non-polar substrate, so that the enzyme could work efficiently on that substrate.

Recycling the cofactor can present difficulties for such a process. However, cofactor recycling methods well known in the art can be applied. For example, an enzyme capable of regenerating the cofactor, using a second substrate can be used. Alternatively, the enzyme can be used in living cells, and the cofactor recycling can be accomplished by feeding the cells the appropriate substrate(s). The NADPH and oxygen can also be replaced by a peroxide, for example hydrogen peroxide, butyl peroxide or cumene peroxide, or by another oxidant. Mutations that enhance the efficiency of peroxide-based oxidation by BM-3 or other cytochrome P450 enzymes can serve to enhance the peroxide shunt activity of the enzyme mutants described here. The mutations described here can be combined with such mutations, for example, and tested for their contributions to peroxide-driven alkane and alkene oxidation.

Screening Assays

In a broad aspect, a screening method to detect oxidation comprises combining, in any order, substrate, oxygen donor, and test oxidation enzyme. The assay components can be placed in or on any suitable medium, carrier or support, and are combined under predetermined conditions. The conditions are chosen to facilitate, suit, promote, investigate or test the oxidation of the substrate by the oxygen donor in the presence of the test enzyme, and may be modified during the assay. The amount of oxidation product, i.e., oxidized substrate, is thereafter detected using a suitable method. Further, as described in WO 99/60096, a screening method can comprise a coupling enzyme such as horseradish peroxidase to enable or enhance the detection of successful oxidation. In some embodiments, one or more cofactors, coenzymes and additional or ancillary proteins may be used to promote or enhance activity of the test oxidation enzyme, coupling enzyme, or both.

In one embodiment, it is not necessary to recover test enzyme from host cells that express them, because the host cells are used in the screening method, in a so-called "whole cell" assay. In this embodiment, substrate, oxygen donor, and other components of the screening assay, are supplied to the transformed host cells or to the growth media or support for the cells. In one form of this approach, the test enzyme is expressed and retained inside the host cell, and the substrate, oxygen donor, and other components are added to the solution or plate containing the cells and cross the cell membrane and enter the cell. Alternatively, the host cells can be lysed so that all intracellular components, including any recombinantly expressed intracellular enzyme mutant, can be in direct contact with any added substrate, oxygen donor, and other components.

Resulting oxygenated products are detected by suitable means. For example, the oxidation product may be a colored, luminescent, or fluorescent compound, so that transformed host cells that produce more active oxidation enzymes "light up" in the assay and can be readily identified, and can be distinguished or separated from cells which do not "light up" as much and which produce inactive enzymes, less active enzymes, or no enzymes. A fluorescent reaction product can be achieved, for example, by using a coupling enzyme, such as laccase or horseradish peroxidase, which forms fluorescent polymers from the oxidation product. A chemiluminescent agent, such as luminol, can also be used to enhance the detectability of the luminescent reaction product, such as the fluorescent polymers. Detectable reaction products also include color changes, such as colored materials that absorb measurable visible or UV light.

To improve the activity of P450 BM-3 or other cytochrome P450 enzymes towards alkanes by directed evolution, a rapid, reproducible screen that is sensitive to small changes (<2-fold) in activity is desirable (Arnold, Accounts of Chemical Research, 31(3): 125-131 March (1998)). Therefore, an alkane analog such as p-nitrophenoxy octane (8-pnpane), can be prepared that generates yellow color upon hydroxylation.

This "surrogate" substrate with a C8 backbone and a p-nitrophenyl moiety is an analog of octane, and allows use of a colorimetric assay to conveniently screen large numbers of P450 BM-3 or other cytochrome P450 mutants for increased hydroxylation activity in microtiter plates (Schwaneberg et al., 1999; Schwaneberg et al., 2001). Hydroxylation of 8-pnpane generates an unstable hemiacetal which dissociates to form (yellow) p-nitrophenolate and the corresponding aldehyde. The hydroxylation kinetics of hundreds of mutants can then be monitored simultaneously in the wells of a microtiter plate using a plate reader (Schwaneberg et al., 2001). This method is particularly suitable for detecting P450 mutants with improved alkane-oxidation activity.

Enzyme mutants displaying improved levels of the desired activity or property in the screening assay(s) can then be expressed in higher amounts, retrieved, optionally purified, and further tested for the activity or property of interest.

Activity Assays

The cytochrome P450 mutants created by directed evolution and selected for a desired property or activity can be further evaluated by any suitable test or tests known in the art to be useful to assess the property or activity. For example, the enzyme mutants can be evaluated for their alkane-oxidation capability, regio- and enantiomeric specificity.

An assay for alkane-oxidation capability essentially comprises contacting the cytochrome P450 mutant with a specific amount of alkane substrate, or a substrate which is an alkane analog such as 8-pnpane, in the presence of an oxygen donor, and any other components (e.g., NADPH) that are necessary or desirable to include in the reaction mixture, such as NADPH and buffering agents. After a sufficient incubation time, the amount of oxidation product formed, or, alternatively, the amount of intact non-oxidized substrate remaining, is estimated. For example, the amount of oxidation product and/or substrate could be evaluated chromatographically, e.g., by mass spectroscopy (MS) coupled to high-pressure liquid chromatography (HPLC) or gas chromatography (GC) columns, or spectrophotometrically, by measuring the absorbance of either compound at a suitable wavelength. By varying specific parameters in such assays, the Michaelis-Menten constant ($K_m$) and/or maximum catalytic rate ($V_{max}$) can be derived for each substrate as is well known in the art. Preferred substrates include, but are not limited to, methane, ethane, propane, butane, pentane, hexane, heptane, octane, and cyclohexane. In addition, HPLC and GC techniques, particularly when coupled to MS, can be used to determine not only the amount of oxidized product, but also the identity of the product. For example, octane can be oxidized to octanol where the hydroxyl group is positioned on any of the carbon atoms in the octanol molecule. The substrates may also be used to determine regio- and enantiomeric specificity of the P450 enzymes.

Alkene-oxidation can be evaluated by methods similar to those described for alkanes, simply by replacing an alkane with the corresponding alkene, and designing an assay which promotes and detects epoxide formation of the alkene. For example, an assay which detects NADPH consumption may be used. Preferred alkene substrates include ethene, propene, butene, pentene, hexene, heptene, and octene.

B. Directed Evolution for the Creation of BM-3 139-3 and the Analysis of the 139-3 Mutant Five rounds of directed evolution starting with wild type cytochrome P450 BM-3 as the parent yielded the alkane hydroxylase 139-3. (Farinas et al., *Adv. Synth. Catal.*, 343, 601-606 (2001), see also, U.S. Pat. Publication 20030100744, Filed Jul. 22, 2002 to Farinas, et al). In each round, a library of randomly-mutated BM-3 enzymes was screened for octane hydroxylation activity on the "surrogate" substrate p-nitrophenyl octyl ether. Hydroxylation of this substrate at the carbon atom containing the p-nitrophenoxy moiety resulted in the formation of p-nitrophenolate, which was used for colorimetric identification of active mutants. Active mutants were then tested for octane hydroxylation activity, and the most active ones were used as parents for subsequent rounds of evolution. In some cases, several active mutants were isolated from a single round of screening and recombined using DNA shuffling to obtain the parent for the next round. In these and the evolution experiments described in this work, random mutagenesis and recombination was applied only to the heme domain (residues 1-429) of the P450; the reductase domain was left untouched. As discussed above, the alkane hydroxylase mutant, 139-3, contained 11 amino acid substitutions in its heme domain.

The fairly even distribution of 139-3's hydroxylated alkane products, however, suggested that its active site was rather large and that its alkane substrates are "loosely" bound. This is consistent with the fact that the surrogate substrate used to select these mutants is quite large relative to octane, the intended substrate. Additionally, the one active site mutation, V78A, likely results in an increase in the size of the substrate binding site due to the decreased size of the amino acid side chain at that residue.

The 139-3 P450 BM-3 mutant exhibited significant activity on propane, despite the fact that small alkane substrates were not used to screen the mutant libraries in the directed evolution experiments. Because of this, as well as other factors, it was reasoned that decreasing the volume of the active site of the 139-3 mutant, using a combination of directed evolution and site-directed mutagenesis might further enhance this activity. Additionally, engineering the active site in this way might also confer regioselectivity towards longer alkanes—if the substrates are bound more tightly, fewer hydroxylation products may be possible. Of course this involves a delicate balance of decreasing the size of the active site as any alteration could result in making the active site so small as to prevent binding of the substrate. Additionally, the alterations could also prevent any activity by the enzyme as well.

The 11 mutations in the 139-3 P450 BM-3 are core mutations. In one embodiment, all eleven of these mutations are preferably in the final P450 mutant in order for it to catalyze the oxidation of an alkane. In another embodiment, only 10, 9, 8, 7, 6, 5, 4, 3, 2, or 1 of these mutations must be present. In another embodiment, the mutant P450 protein only includes eight core mutations, as follows: V78A, T175I, A184V, H236Q, E252G, R255S, and L353V. In another embodiment, the aforementioned mutations are not included, however similar amino acid or amino acids are preferably included so that alkane activity is conferred upon the enzyme. For example, each core mutation might be replaced with a conservative variant of the core mutant amino acid. Without intending to be limited by theory, it is possible that the change in these amino acids result in the 139-3 P450 BM-3 being able to catalyze the hydroxylation of alkanes. In one embodiment, only V78A is required as a core mutation. Thus, an enzyme with the V78A mutation will effectively hydroxylate alkanes. As discussed further below, additional mutations give the P450 mutant the ability to hydroxylate the alkane enantio- and regioselectively.

C. Mutation of the 139-3 P450 Enzyme for Regio- and Enentioselective Mutants

Initially, two rounds of directed evolution was performed using 139-3 as the parent and propane as the screening substrate. A BM-3-catalyzed hydroxylation reaction results in the oxidation of one equivalent of NADPH for each equivalent of hydroxylated substrate. Using a 96-well plate reader, the rate of NADPH oxidation in the presence of BM-3-containing cell lysate and substrate was monitored spectrophotometrically at 340 nm to quickly identify mutants with high activity towards any given substrate. (Glieder et al., *Nature Biotech.*, 20:1135-1139 (2002)).

1. 1st Round

A library of P450 BM-3 mutants was generated by performing a first round of directed evolution, wherein P450 BM-3 mutant 139-3 was combined with 15 other unsequenced P450 mutants of the same generation that also exhibited increased activity towards p-nitrophenyl octyl ether and octane. The library was transformed into *E. coli* (DH5α) competent cells, over-expressed, and lysed according to standard protocols developed by our laboratory. Aliquots of the cell-free extract of each mutant were transferred to 96-well plates where NADPH consumption was monitored in the presence of propane. Mutants identified from the screening process were then grown up and purified for comparative analysis using gas chromatography.

2. 2nd Round

Mutant J was selected from the first round of directed evolution, based upon its increased rate of propane oxidation. This mutant was then used as the parent for the second round of evolution, the library for which was generated by error-prone PCR under conditions designed to yield 1 to 2 mutations in the heme domain of the P450 on average per gene.

Mutant 9-10A was selected from this library for its increased propane hydroxylation rate. The properties of these mutants are detailed in Tables 1-3 and FIG. 2. Neither mutant J, nor mutant 9-10A acquired active-site mutations and showed no major changes in regioselectivity towards longer alkanes.

TABLE 1

Amino Acid Mutation in P450 BM-3 Mutants Accumulated Each Generation

| Position (WT) | DNA Mutation | 139-3 aa | J aa | 9-10A aa | 9-10A-A82L Aa | 9-10A-A328V aa | 1-12G aa |
|---|---|---|---|---|---|---|---|
| RV47 | C142T | | | C | C | C | C |
| V78 | T236C | A | A | A | A | A | A |
| A82 | 247-249[a] | | | | L | | L |
| K94 | A284T | | | I | I | I | I |
| F107 | C324T | F | F | F | F | F | F |
| H138 | | | Y | | | | |
| P142 | C427T | | | S | S | S | S |
| T175 | C527T | I | I | I | I | I | I |
| V178 | | | I | | | | |
| A184 | C554T | V | V | V | V | V | V |
| F205 | T617G | | C | C | C | C | C |
| S226 | C681G | | R | R | R | R | R |
| H236 | T711G | Q | Q | Q | Q | Q | Q |
| E252 | A758G | G | G | G | G | G | G |
| R255 | C766A | S | S | S | S | S | S |
| A290 | C872T | | V | V | V | V | V |
| A295 | | | T | | | | |
| A328 | C986T | | | | | V | V |
| L353 | C1060G | V | V | V | V | V | V |
| E372 | A1119G | | E | E | E | E | E |

[a] A82L DNA mutation was GCA to CTT.

TABLE 2

Product Distributions (% total Alcohols[a]) and % ee of Selected Products

| Mutant | product | hexane | % ee[c] | heptane | % ee[c] | Octane | % ee[c] | nonane | % ee[c] | decane | % ee[c] |
|---|---|---|---|---|---|---|---|---|---|---|---|
| 139-3 | 1-alcohol | 0 | | 0 | | 1 | | 0 | | 0 | |
| | 2-alcohol | 14 | 14(S) | 30 | 15(S) | 61 | 58(S) | 30 | 83(S) | 15 | |
| | 3-alcohol | 86 | 39(S) | 42 | 15(S) | 20 | | 50 | | 37 | |
| | 4-alcohol | | | 29 | | 17 | | 21 | | 49 | |
| | ketones[b] | <1 | | 3 | | 5 | | 5 | | 7 | |
| J | 1-alcohol | 0 | | 1 | | 1 | | 0 | | 2 | |
| | 2-alcohol | 23 | 20(S) | 29 | 12(S) | 52 | 57(S) | 29 | 65(S) | 16 | |
| | 3-alcohol | 77 | 46(S) | 42 | 11(S) | 25 | | 48 | | 35 | |
| | 4-alcohol | | | 28 | | 22 | | 23 | | 48 | |
| | ketones[b] | <1 | | 2 | | 5 | | 5 | | 5 | |
| 9-10a | 1-alcohol | 0 | | 1 | | 1 | | 0 | | 1 | |
| | 2-alcohol | 6 | 14(S) | 26 | 7(S) | 53 | 50(S) | 39 | 60(S) | 16 | |
| | 3-alcohol | 95 | 41(S) | 41 | 8(S) | 20 | | 59 | | 32 | |
| | 4-alcohol | | | 33 | | 26 | | 3 | | 51 | |
| | ketones[b] | <1 | | 3 | | 5 | | 5 | | 6 | |
| | 1-alcohol | 0 | | 0 | | 0 | | 1 | | 0 | |
| | 2-alcohol | 35 | 39(S) | 27 | 4(S) | 22 | 10(S) | 16 | 7(S) | 21 | |

TABLE 2-continued

Product Distributions (% total Alcohols[a]) and % ee of Selected Products

| Mutant | product | hexane | % ee[c] | heptane | % ee[c] | Octane | % ee[c] | nonane | % ee[c] | decane | % ee[c] |
|---|---|---|---|---|---|---|---|---|---|---|---|
| 9-10A-A82L | 3-alcohol | 65 | 42(S) | 46 | 30(S) | 25 | 17(R) | 16 | | 19 | |
| | 4-alcohol | | | 29 | | 53 | | 67 | | 60 | |
| | ketones[b] | <1 | | 2 | | 5 | | 5 | | 5 | |
| | 1-alcohol | 6 | | 14 | | 10 | | 3 | | 1 | |
| | 2-alcohol | 64 | 21(R) | 62 | 15(R) | 80 | 40(S) | 76 | 0 | 79 | 5(S) |
| 9-10A-A328V | 3-alcohol | 30 | | 17 | | 8 | | 19 | | 17 | |
| | 4-alcohol | | | 6 | | 2 | | 3 | | 2 | |
| | ketones[b] | <1 | | <1 | | <1 | | <1 | | <1 | |
| | 1-alcohol | 9 | | 5 | | 5 | | 3 | | 1 | |
| | 2-alcohol | 77 | 4(R) | 76 | 40(R) | 82 | 39(R) | 86 | 52(R) | 86 | 55(R) |
| 1-12G | 3-alcohol | 14 | | 15 | | 11 | | 7 | | 9 | |
| | 4-alcohol | | | 3 | | 3 | | 5 | | 4 | |
| | ketones[b] | <1 | | <1 | | <1 | | <1 | | <1 | |

[a]Product distribution for each alcohol determined by ratio of a specific alcohol product to the total amount of all alcohol products. Errors are at most ±1%.
[b]Product distribution for ketones was similar to alcohol product distribution. The numbers reported here are the total amount of all ketones to total products (alcohols and ketones).
[c]Favored enantiomer is listed in parentheses. Errors are at most ±5%.

TABLE 3

Catalytic Properties of Mutants of P450 BM-3

| Mutant | Substrate | Max. rate (min$^{-1}$)[a] | Total Turnover |
|---|---|---|---|
| 139-3 | octane | 2000 | 1000 |
| | propane | 100 | 500 |
| J | octane | 3000 | 3000 |
| | propane | 600 | 800 |
| 9-10A | octane | 3000 | 3000 |
| | propane | 500 | 1100 |
| 9-10A-A82L | octane | 1500 | 6000 |
| | propane | 200 | 2360 |
| 9-10A-A328V | octane | 1000 | 2000 |
| | propane | 300 | 100 |
| 1-12G | octane | 400 | 7500 |
| | propane | 20 | 6020 |

Figure 3A:
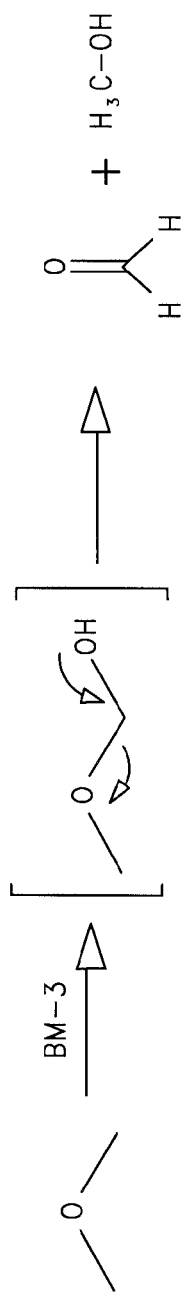
FIG. 3A is a reaction schematic of the hydroxylation of dimethyl ether to produce formaldehyde.
Figure 3B:
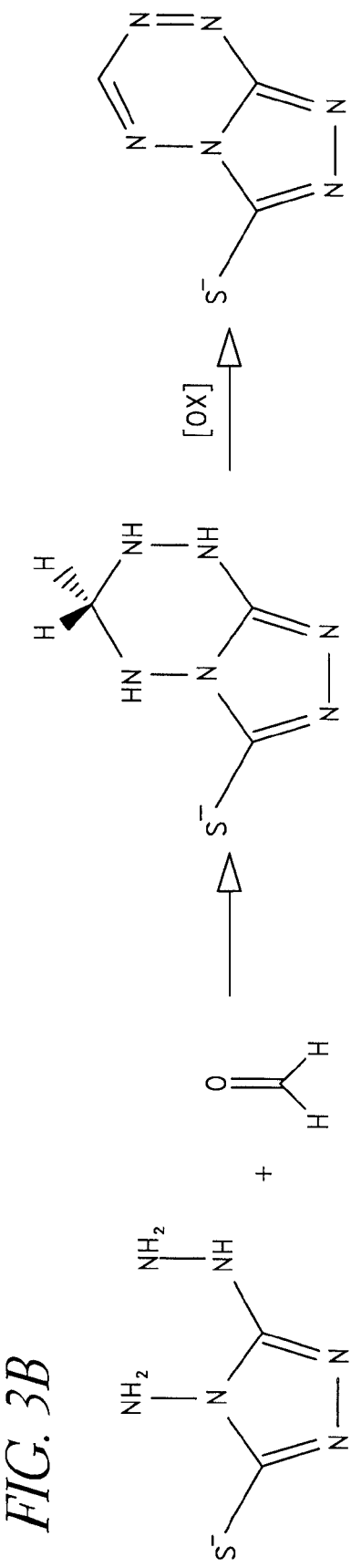
FIG. 3B is a reaction schematic of Purpald with formaldehyde to form a purple colored adduct upon air oxidation (the first two compounds are colorless).

[a]Rate units are measured by NADPH depletion as nmol NADPH oxidized/min/nmol protein 3. 3rd Round Mutant 9-10A was used to parent a third random-mutagenesis library. In addition to screening for increased propane oxidation activity using NADPH consumption rates, a second screen was applied to this library to assess the amount of propane hydroxylation products generated by each mutant. This screen depended upon the surrogate substrate dimethyl ether, which is similar in size and C-H bond strength to propane. Upon hydroxylation, dimethyl ether forms formaldehyde, which can be detected with Purpald dye (Hopps, H. B. *Aldrichim. Acta*, 33, 28-30 (2000))(FIG. 3A, showing the hydroxylation of the surrogate substrate dimethyl ether produces formaldehyde and FIG. 3B, showing that purpald reacts with formaldehyde to form a purple adduct upon air oxidation).

The third round of evolution did not produce a mutant with either increased propane hydroxylation activity or more propane hydroxylation products. A possible explanation for this may be that further increases in activity require two or more simultaneous, or coupled, genetic mutations. Such events occur with very low probability and will not be found in screening a few thousand clones. Therefore, two residues were identified in the active site of mutant 9-10A as targets to modify by site-directed mutagenesis. The effect of these changes on alkane hydroxylation activity and product regioselectivity was then examined.

4. 4th Round

Crystal structures of wildtype P450 BM-3 with and without substrate reveal large conformational changes upon substrate binding at the active site (Haines et al., Biochemistry, 40 (45):13456-13465 (2001); Li and Poulos, 1997; Paulsen and Ornstein, Proteins-Structure Function and Genetics, 21 (3):237-243 (1995); and Chang and Loew, (Biochemistry, 39 (10):2484-2498 (2000)). The substrate free structure displays an open access channel with 17 to 21 ordered water molecules. Substrate recognition serves as a conformational trigger to close the channel, which dehydrates the active site, increases the redox potential, and allows dioxygen to bind to the heme.

A tyrosine (Tyr51) at the entrance to the substrate-binding pocket makes a hydrogen bond to the carboxylate group of the substrate in the crystal structure of the enzyme bound with palmitoleic acid (Li and Poulos, 1997). Arg 47, also at the entrance to the binding pocket, may form an ionic interaction as well. Nonpolar alkane substrates must rely solely on hydrophobic partitioning into the enzyme's extended substrate channel, and poor substrate recognition may contribute to P450 BM-3's sluggish activity on octane and other alkanes or alkenes.

Using the crystal structures of heme domain of wild type BM-3 containing a bound substrate (FIG. 4), two residues were identified that could influence substrate binding. Alanine 328 sits in the substrate binding pocket of BM-3 directly above the heme cofactor and is the closest residue in the protein to the proximal side of the heme iron. This residue and its mutation to valine in the wild type enzyme had been reported to affect substrate binding and turnover rates on fatty acids. (Peterson et al., In *Sixth International Symposium on Cytochrome P450 Biodiversity*: University of California, Los Angeles, 2002). FIG. 4 shows the position of A328 and A82 in the active site of wild type cytochrome P450 BM-3. The illustration was made from the coordinates of the crystal structure 1JPZ. The substrate is palmitoyl glycine and the terminal end (ω) of the substrate is indicated.

Site-directed mutagenesis was used to change alanine 328 in 9-10A into the larger hydrophobic residue valine and determined the activity of this mutant (termed 9-10A-A328V) towards several alkanes. Neither the propane hydroxylation activity nor the total propane turnovers of this mutant improved relative to its parent, but a dramatic shift in its regioselective hydroxylation of longer alkanes was discovered. Wild type and all mutants of BM-3 generated by directed evolution were found to hydroxylate longer alkanes, such as heptane, octane, and nonane and form roughly equivalent distributions of 2- 3-, and 4-alcohols. Mutant 9-10A-A328V, on the other hand, formed primarily (>80%) 2-alcohols with these substrates. With octane, the resulting 2-alcohol was ~70% S-2-octanol (40% ee) (Tables 2, 3, FIG. 2, in FIG. 2, the first bar represents the 1-alcohol formed, the second bar represents the 2-alcohol formed and the third bar represents the 3-alcohol formed). Other alkanes, however, were not hydroxylated enantioselectively.

The second side chain in the BM-3 active site that was selected for alteration is located near the active site of the protein formed after the conformational change associated with substrate binding occurs. In the crystal structure of BM-3 with the bound substrate palmitoyl glycine, the residue alanine 92 is located within 3.5 Å of the terminal end of the substrate. (Haines et al. *Biochemistry*, 40, 13456-13465 (2001)). Given the proximity of this residue to the substrate, it is possible that changing this residue to a larger hydrophobic side chain could result in a decreased active site volume upon substrate binding. Lacking information to choose an appropriate residue, a small library containing the four large hydrophobic amino acids, leucine, isoleucine, valine, and phenylalanine at position 82 was prepared, and the library was screened using dimethyl ether and Purpald. Mutant 9-10A-A82L was identified from this screen, and subsequent gas chromatographic analysis of reaction mixtures using this mutant revealed that it supported more turnovers with propane than the 9-10A parent. Additionally, the hydroxylation of longer alkanes using this mutant revealed a shift in product regioselectivity, but in this case favoring the formation of primarily 3- and 4-alcohols.

5. 5th Round

The heme domain genes of J, 9-10A, 9-10A-A328V, and A82L 9-10A were recombined using DNA shuffling to generate a library and the library was then screened for improved propane activity using the NADPH consumption screen in the presence of propane and the dimethyl ether/Purpald screen. The mutant with the highest activity, 1-12G, was selected from this library and its alkane hydroxylation activity was determined.

Surprisingly, 1-12G contained all of the mutations introduced into the recombination library. 1-12G is the double mutant A328V/A82L of 9-10A. Additionally, all of the background mutants present in the 139-9 original parent were also present in 1-12 G. Like the 9-10A-A328V, 1-12G hydroxylates alkanes at the 2-position (>80%). However, chiral GC analysis of these products revealed that 1-12G is enantioselective for the R-2-alcohols (40-55% ee), of heptane, octane, nonane, and decane (Tables 2, 3, FIG. 2). "ee" represents the difference in the two products created divided by the sum of the two products. The addition the A82L mutation to 9-10A-A328V mutant shifted the substrate octane in the active site such that the opposite enantiomer of its 2-alcohol was apparently favored. The direct regio- and enantioselective hydroxylation activity towards linear alkanes exhibited by this mutant at these high rates and total turnover numbers was surprising. The A82L mutation also increased the stability of the enzyme, bringing the total turnovers for propane and octane to well over 5000.

As the 9-10A-A328V and the 1-12G mutants hydroxylate alkanes at the 2-position, the mutations that these mutants possess compared to the 139-3 mutant represent the regioselective hydroxylation mutations, as shown in Table 1. Additionally, as the 9-10A-A328V mutant is enantioselective over the 139-3 mutant, in creating the S-2 octanol, the mutations that are different between 9-10A-A328V and the 139-3 mutant represent the enantioselective mutants, and in particular the S-enantioselective mutants, as shown in Table 1. Additionally, as the 1-12G mutant is enantioselective over the 139-3 mutant in creating the R-2 octanol, the mutations that are different between 1-12G and the 139-3 mutant represent enantioselective mutants, and in particular the R-enantioselective mutants. These differences, as well as any others that are similarly discovered, represent the regio and enantioselective mutants.

Accordingly, those amino acid positions (or corresponding positions in a different P450) that should be changed are illustrated in Table 1, so that one of ordinary skill in the art can produce a regioselective and/or enantioselective P450 enzyme. In one embodiment, the amino acids are identical to those described in Table 1. In another embodiment, the residues are conservative variants of those described in Table1. In one embodiment, all of the residues that are characterized as regio- or enantioselective are required in order to have a P450 protein that is regio- or enantioselective. In another embodiment, only 1, 2, 3, 4, 5, 6, 7, 8, 9, 10, 11, or 12 of these residues are required. The most important residues and guidance of which combination of residues or which additional residues can be changed for the same selectivity will be guided by the results presented herein, the tables showing the key residues, the crystal structure of P450, and the knowledge of one of ordinary skill in the art.

There are some residues that might be classified as core residues, but are not present in either of the mutants 9-10A-A328V or 1-12. For example, residues H138, V178, and A295 are core residues of P450 BM-3 as mutation of them results in a P450 enzyme with enhanced alkane hydroxylation activity. However, these three residues are not mandatory for the altered or enhanced enantio- and regioselectivity of P450s, as these residues were not present on at least the 9-10A-A328V and 1-12G mutants.

D. Characterization of the Activity of 139-9 BM-3 Mutants

To measure the alkane hydroxylation activity of the BM-3 mutants, ethanol solutions of liquid alkanes (hexane to decane) were added to buffer solutions of the enzyme such that the total amount of ethanol in the reaction mixture was one percent. Several solvents, including ethanol, methanol, acetone, and dimethyl sulfoxide, were tested and ethanol was shown to support the most product turnovers. Reactions with liquid alkanes that contained no co-solvent produced no detectable products. In the absence of substrate, NADPH has been reported to inactivate BM-3 by over-reducing the flavin cofactors in its reductase domain. (Daff et al., *Biochemistry*, 36, 13816-13823 (1997)). To avoid this problem, substrate was added to the enzyme first and incubated for a few seconds before adding NADPH.

Dioxygen was not added to these reactions, limiting the amount of possible product formed to the 225-250 µM of oxygen present in air-saturated buffer. The addition of excess dioxygen to the reactions by direct bubbling or rapid stirring did not increase and often decreased the total product turn over, possibly by denaturing the protein. Reaction mixtures for all of our BM-3 mutants containing 0.5-1.0 µM enzyme produced 225-250 µM products, indicating that NADPH oxidation is tightly coupled to product formation in all of these systems. At very low concentrations of BM-3, the FMN cofactor has been reported to diffuse out of the protein and inactivate it. (Strobel et al., *Cytochrome P450: Structure, Mechanism, and Biochemistry (Second Edition)*). Given this fact and problems with measuring total turnover numbers using less than ~50 nM protein (>5000 turnovers, given the 250 µM limit on product formation in the reactions), in an optimized reaction environment, it is likely that mutant 1-12G is capable greater than the approximately 7000 turnovers reported here.

Reactions using propane did not contain co-solvent because of potential competition between the solvent and the small substrate. These reactions were performed in propane saturated buffer under an atmosphere of propane and dioxygen (provided by a balloon filled with the two gases). The addition of this atmosphere ensured that both gaseous substrates were saturated in the reaction solution, sine a balloon of just propane or oxygen would dilute the concentration of the other gas. Total turnovers determined with this system were not dependent on oxygen concentration in the balloon (data not shown), illustrating that only the original 250 µM of dioxygen in the buffer was available to the reaction. Additionally, we discovered that NADPH could neither be purchased nor easily purified in a form that contains less than 2-3% ethanol, which interferes with our analysis of the reaction products. For this reason, an NADPH-regeneration system based upon isocitrate dehydrogenase was used for propane reactions. (Schwaneberg et al., *Biomol. Screening*, 6, 111-117 (2001)).

The alkane hydroxylation product distributions from mutant 9-10A-A328V clearly show its selectivity towards the 2-position. The fact that only 2-octanol is formed enantioselectively but not 2-heptanol or 2-nonanol suggests that a substrate-protein contact specific to the terminal methyl group of octane induces its enantioselectivity towards this single substrate. Since the other non-regioselective mutants 139-3, J, and 9-10A also exhibit this enantioselectivity towards octane, this contact probably functions independently of the 328th residue. If this contact could be mimicked by changing other residues in the binding pocket, then it might be possible to engineer a mutant enantioselective for the S-2-position of other alkanes.

The addition of the A82L mutation to the 9-10A-A328V mutant overcame the enzyme's preference for octane, but in the process shifted the substrate in the binding pocket such that R-2-alcohols were the favored products (FIG. 5). This residue was selected for its proximity to the terminal end of the substrate in a crystal structure, but it is not clear if the larger leucine side chain "pushes" the substrate further up the active site or blocks the channel such that the substrate is flipped relative to its position in the A328V mutant. In addition to its effect on substrate selectivity, the A82L mutation both with and without the A328V mutation conferred approximately an order of magnitude increase in stability as determined by total turnover number.

E. Whole Cell Biocatalysis

Two of the major obstacles to implementing a biocatalytic process are the need for large amounts of purified protein and expensive cofactors. Lysates of *E. Coli* (DH5α) containing the overexpressed cytochrome P450 BM-3 mutants exhibit the same activity as purified protein, but still require the addition of expensive NADPH.

An isocitrate dehydrogenase-based NADPH regenerating system can be used to perform reactions using both cell lysate and purified protein with results indistinguishable from using NADPH alone. However, it is possible that the current embodiments could be used in an *E. coli* system as a whole cell catalyst since the alkane substrates and alcohol products should be permeable to the cell membrane. To test this hypothesis, whole cell cultures of DH5α overexpressing the 9-10A-A328V and the 1-12G mutants were prepared.

Figure 6A:
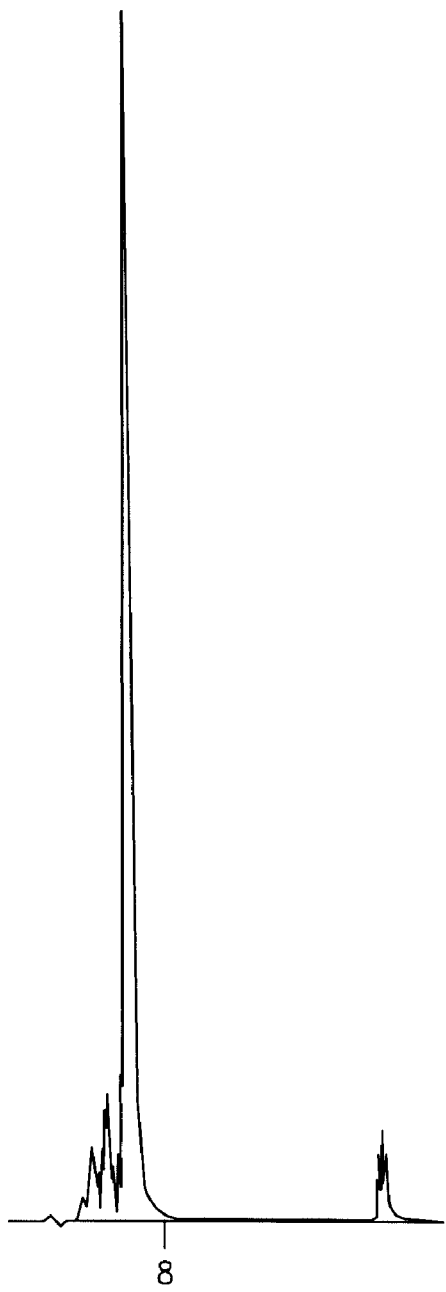
FIG. 6A is a GC/FID analysis of the octane hydroxylation product distributions using 9-10A-A328V as a purified protein.
Figure 6B:
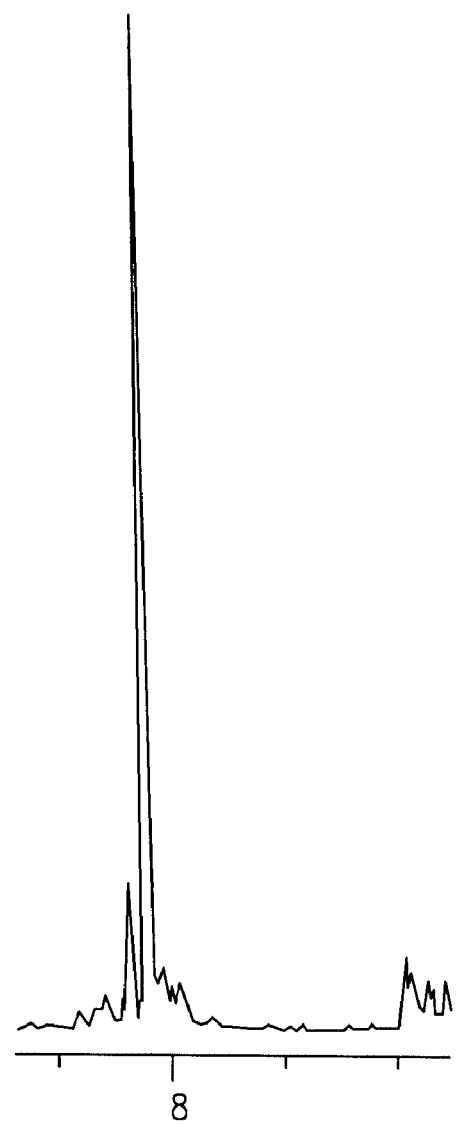
FIG. 6B is a GC/FID analysis of the octane hydroxylation product distributions using 9-10A-A328V from a whole cell.

While the system was not optimized, the cells were prepared and fed octane according to a published procedure wherein *E. coli* K27 cells expressing wild-type BM-3 was used with dmyristic acid as a substrate. (Schneider et al., *Asymmetry.*, 9, 2833-2844 (1998); Schneider et al., *Biotech. Bioeng.*, 64, 333-340 (1999)). Isopropyl-β-D-thiogalactopyranoside (IPTG) was used to induce growth of the proteins (as the genes are tac promoted genes), in place of the fatty acid sensitive promoter used in the published system. Extraction of these whole cell reactions with methylene chloride and analysis of the products revealed that both the regio- and enantioselectivity of the alkane hydroxylation products were preserved using the whole cell system (FIG. 6). These whole cell reaction conditions, similar in principal to the two-phase whole cell systems described by Schneider, et al. for AlkB octane hydroxylation, provide a cost-effective use of these *E. coli* cells for alkane hydroxylation. (Mathys et al., *Biotech. Bioeng.*, 64, 459-477, (1999)).

F. Alternative Substrates

The alkanes shown above were perhaps the most difficult substrates to hydroxylate selectively as they have very little in the way of features which can be used to direct hydroxylation. As such, the active site mutants of 9-10A will be more selective on substrates with rigid shapes and functional groups that can only be bound in our active site in a single conformation.

In some embodiments, the regio- and enantioselective enzymes will also allow the regio and enantioselective hydroxylation of nonfatty acids that are not considered alkanes. For example, the enzymes are able to specifically hydroxylate alkanes with other functional groups, alkenes, cyclic carbon groups of various sizes. In one embodiment, the mutant enzymes can regio- and enantioselectively hydroxylate any carbon which can be hydroxylated, and which is large enough to allow a limited number of binding positions in the binding site. For example, cyclized carbon groups, being more rigid than alkanes, will allow regio- and enantioselective hydroxylation.

G. Ethane Hydroxylation

The ability to modify BM-3 such that it can bind small alkane substrates tightly enough to hydroxylate them selectively also suggests that practical ethane and methane hydroxylation chemistry is possible with this system. Variant 1-12G is active (approximately slightly less than 100 total turnovers) on ethane. This ethane activity appears to be the first reported by a cytochrome P450 enzyme. More broadly, it appears that the 1-12G variant is the first P450 capable of binding ethane. The particulars of how 1-12G interacts with the ethane substrate are discussed in more detail in the examples below.

H. Additional Mutants

In addition to the mutants described above, additional mutations may be added to any of the above mutants in order to obtain enzymes with greater hydroxylation activity or altered or a higher degree of enantio- or regiospecificity. As there is a crystal structure available for P450 BM-3, and as the above mutants may be encompassed into models of the mutant enzyme, additional mutations may be made in a selective manner to particular areas of the protein. In particular, mutations at the active site that appear to further reduce or constrain a substrate should lead to an enzyme with the desired characteristics. Examples of such mutants and the resulting characteristics can be found in Table 4. The background for the mutants on Table 4 was the 9-10A mutant. The total turnover rates for the mutants are comparable to that of 9-10A (or up to 50% better).

TABLE 4

| %1-oct Product | %2-oct Product | %3-oct Product | %4-oct Product | favored | mutation |
|---|---|---|---|---|---|
| 2.7 | 42.2 | 18.4 | 16.8 | 2-octanol | L75I |
| 3.3 | 46.1 | 18.4 | 23.7 | 2-octanol | L75W |
| 3.6 | 22.2 | 27.4 | 44.5 | 4-octanol | A78T |
| 4.0 | 36.8 | 17.1 | 31.2 | mix | A78F |
| 5.4 | 48.1 | 18.2 | 20.1 | 2-octanol | A78S |
| 5.1 | 23.1 | 25.1 | 43.9 | mix | A82T |
| 5.6 | 39.9 | 19.2 | 25.5 | 2-octanol | A82S |
| 4.3 | 25.7 | 19.5 | 47.6 | 4-octanol | A82F |
| 3.7 | 11.2 | 20.6 | 58.8 | 4-octanol | A82I |
| 4.5 | 25.5 | 25.8 | 42.3 | 4-octanol | A82C |
| 6.6 | 52.4 | 16.8 | 22.7 | 2-octanol | A82G |
| 8.3 | 70.0 | 5.9 | 2.7 | 2-octanol | F87I |
| 4.5 | 52.0 | 13.0 | 4.2 | 2-octanol | F87V |
| 6.8 | 55.2 | 21.7 | 11.9 | 2-octanol | F87L |
| 3.6 | 50.8 | 20.7 | 22.2 | 2-octanol | T88C |
| 7.0 | 66.7 | 11.2 | 9.7 | 2-octanol | T260L |
| 5.7 | 38.5 | 25.5 | 29.0 | mix | T260S |
| 5.6 | 28.8 | 22.9 | 41.6 | 4-octanol | T260N |
| 5.6 | 87.7 | 3.5 | 0.0 | 2-octanol | A328F |
| 24.4 | 70.6 | 0.0 | 0.0 | 2-octanol | A328M |
| 13.1 | 86.9 | 0.0 | 0.0 | 2-octanol | A328L |

As can be seen from the results in Table 4, these mutations, selected to minimize the space of the active site, resulted in varied regioselective enzymes, including enzymes that are capable of hydroxylating alkanes at the fourth position. A favored position is defined as one in which at least 40% of the product exists. These same mutations and similar selective processes are useful for the other mutants described herein and for mutants resulting from the processes described herein. The product percentages may not add up to 100% for each mutant because there are some overoxidation products, e.g. the corresponding ketones, for some of the mutants. One especially surprising result was that the mutant proteins exhibited highly diverse and varying regio- and enantioselective properties. Thus, by using directed evolution as described above, and then selectively altering the active site amino acids so as to minimize the manner in which the substrate may bind to the active site, large numbers of very diverse, but desirable proteins can be achieved. Thus, in one embodiment, methods for creating such libraries, and the libraries themselves are contemplated. Examples of such mutants are disclosed in SEQ ID NOS: 3-54.

I. Variants of 139-3 Other Mutants

One embodiment provides for a novel variant P450 BM-3 cytochrome P450 oxygenase in which one or more of the amino acid residues listed in Table 1A, which are not core residues, have been conserved. In one embodiment, the conserved residue is one that is different between either 9-10A-A82L and 139-3, 9-10-A328V and 139-3, and 1-12G and 139-3. Conservation of an amino acid residue can show that the residue has an important function for the oxygenase activity and/or stability of the P450 enzyme. Thus, the P450 BM-3 mutations identified herein to improve alkane-oxidation activity can simply be translated onto such non-P450 BM-3 enzymes to yield improved properties according to the invention.

Any method can be used to "translate" the P450 BM-3 mutation onto another cytochrome P450 enzyme, and such methods are well known in the art. For example, sequence alignment software such as SIM (alignment of two protein sequences), LALIGN (finds multiple matching subsegments in two sequences), Dotlet (a Java applet for sequence comparisons using the dot matrix method); CLUSTALW (available via the World Wide Web as freeware), ALIGN (at Genestream (IGH)), DIALIGN (multiple sequence alignment based on segment-to-segment comparison, at University of Bielefeld, Germany), Match-Box (at University of Namur, Belgium), MSA (at Washington University), Multalin (at INRA or at PBIL), MUSCA (multiple sequence alignment using pattern discovery, at IBM), and AMAS (Analyse Multiply Aligned Sequences).

A person of skill in the art can choose suitable settings, or simply use standard default settings, in these programs to align P450 BM-3 with another cytochrome P450 enzyme. U.S. Pat. Publication No. 20030100744 has a representative sequence alignment (e.g., in FIG. 20 and Table 2.) The sequence alignments of P450 BM-3 with other cytochrome P450 enzymes can be taken from the literature, and amino acid residues corresponding to the mutated amino acid residues of the invention identified. For example, such information can be derived from de Montellano Cytochrome P450: Structure, Mechanism, and Biochemistry (Plenum Press, New York 1995), see, especially, FIG. 1 on page 187).

While some P450 enzymes may not share significant sequence similarities, particular domains such as the heme-containing domains of P450s do display close structural similarity. Therefore, the positions of the various mutations described here can be translated to similar positions in different P450 enzymes having very low sequence similarity to P450 BM-3 using molecular modeling of those P450s based on sequence homology. Examples of using such techniques to model various P450s based on sequence homology with P450 BM-3 are available (Lewis et al., 1999). The same mutations described here, when placed in their corresponding positions in other P450 structures (as determined by modeling) would confer similar improvements in alkane oxidation activity.

Figure 7:
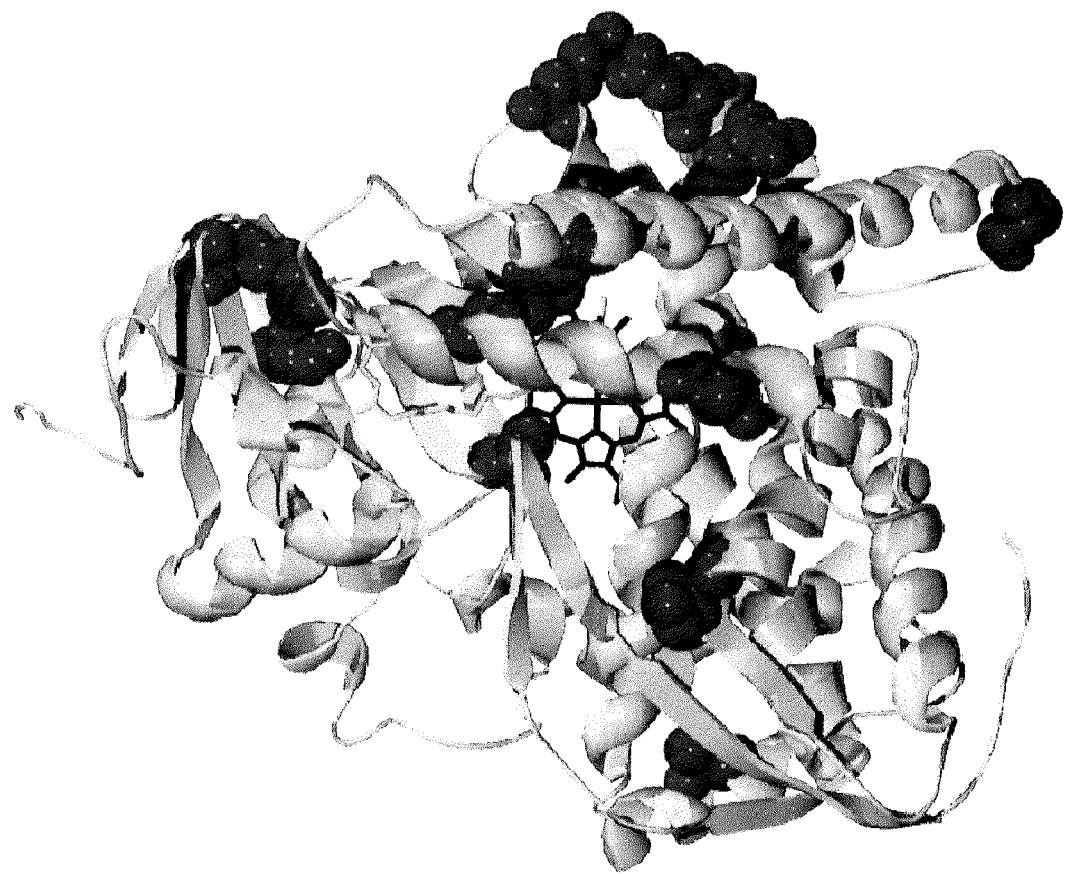
FIG. 7 is a depiction of a P450 molecule with the point mutations for the 1-12G mutant displayed as space filling structures.

An example of such a structure is demonstrated in FIG. 7. The P450 is displayed in a ribbon format, while the locations and shapes of the point mutations are displayed in space filling structures.

In one embodiment, the P450 variants will have at least one of the novel mutations described herein. In one embodiment, the P450 variant will have at least one of the mutations that is different between the 139-3 parent and one of the $3^{rd}$, $4^{th}$, or $5^{th}$ generation enzymes, as shown in Table 1. In one embodiment, the variant will have all 8 of the primary core mutations from the 139-3 parent, as well as at least one mutation from later generations. In one embodiment, the later generation is selected from the following: J, 9-10A, 9-10A-A82L, 9-10A-A328V, 1-12G. In one embodiment, a variant will have one of the "selective hydroxylation mutations." In another embodiment, the variant will have at least one of the mutations described in Table 4. In another embodiment, a variant will have at least one of the core mutations and at lest one selective hydroxylation mutation. A functional variant is a variant that functions as the mutant functions, but has different mutations that allow it to so function. Such variants are described herein, as the process for identifying such variants has been fully described in the making of the mutant itself.

EXAMPLES

All liquid alkane substrates, product standards, and solvents were from Sigma-Aldrich, Inc. (St. Louis, Mo.). The gases propane and dimethyl ether were from Advanced Gas Technologies (Palm, Pa.). Isocitrate dehydrogenase and NADP+ was from Sigma-Aldrich, Inc. (St. Louis, Mo.). NADPH was from Biocatalytics, Inc. (Pasadena, Calif.).

Example 1

This example demonstrates one method by which recombination of the P450 BM-3 mutants may occur, as done in the first 1st library recombination. The first generation of mutants was created by StEP recombination of mutant 139-3 (V78A, H138Y, T175I, V178I, A194V, H236Q, E252G, R255S, A290V, A295T) with 15 other mutants from the same generation. (Glieder et al., Nature Biotech., 20, 1135-1139 (2002)), Zhao et al., Nature Biotechnology, 16, 258-261 (1998)). A mutant, J, (V78A, T175I, A184V, F205C, S226R, H236Q, E252G, R255S, A290V, L353V) was isolated based on its increased NADPH depletion rate using propane as a substrate. Table 2 displays the enantio- and regiospecific qualities of the J mutant. For example, the J mutant produces less of the 2-alcohol than the 139-3 mutant does. However, the J mutant creates more of the 3-alcohol than the 139-3 mutant does. Table 3 displays the rate of NADPH depletion as 3000 $min^{-1}$ for octane and 600 $min^{-1}$ for propane. These values are clearly higher than the 2000 and 100 rates for the 139-3 mutant P450. The distribution of the products can be seen in FIG. 2 and in Table 2. This distribution of products is also known as the hydroxylation profile. Here, the profile for, for example, octane if 1%, 52%, 25%, 22%, and 5%, for the 1-alcohol, 2-alcohol, 3-alcohol, 4-alcohol, and ketone respectively. The hydroxylation profile is also 57% (S) ee. As can be seen comparing these results to the 139-3 results for octane, the J mutant clearly has an altered hydroxylation profile. For example, for hexane, the J mutant produces 23% of the product in the 2-alcohol form, while the 139-3 mutant only produces 14% of hexanes in the 2-alcohol form.

Example 2

This example demonstrates one method by which random mutagenesis of P450 BM-3 may be achieved, as described in the 2nd and 3rd library steps above. The second and the third generation were created by error-prone PCR using the Genemorph kit (Strategene, La Jolla, Calif.) according to the manufacturer's protocol, using approximately 50 ng (xng for third) of plasmid DNA as template and primers BamHI-forw (5'-ggaaacaggatccatcgatgc-3'; SEQ ID NO: 55) and SacI-rev (5'-gtgaaggaataccgccaagc-3'; SEQ ID NO: 56). Mutant 9-10A (R47C, V78A, K94I, P142S, T175I, A184V, F205C, S266R, H236Q, E252G, R255S, AS90V, L353V) was isolated from the 2nd generation based on increased NADPH consumption and NADP+ formation using propane as a substrate. No increase in activity was observed in the products of the third library. Table 3 displays the catalytic properties of the 9-10A mutant produced from this step. While the rate of octane synthesis has not changed, relative to the J mutant, the rate of propane synthesis has actually decreased, although both are still substantially above the rates for the 139-3 mutant. Of course, the total turnover for 9-10A, 1100, is greater than the total turnover for J, 800. The distribution of the products can be seen in FIG. 2 and in Table 2.

Example 3

This example demonstrates one method by which site directed mutagenesis may be performed, as described above in the $3^{rd}$ and $4^{th}$ generations. Base substitution mutations were introduced into mutant 9-10A by PCR overlap extension mutagenesis. (Higuchi et al., Nucleic Acids Res., 16, 7351-7367 (1988)). Position A82 was mutated to L, I, V and F using mutagenic primers A82forw (5'-ggagacgggttatttacaagc-3'; SEQ ID NO: 57) and A82rev (6'-gcttgtaaataacccgtctc-caanaaaatcacg-3'; SEQ ID NO: 58). Position A328 was mutated to V using mutagenic primers A328V forw (5'-gct-tatggccaactgttcctgc-3'; SEQ ID NO: 59) and A328V rev (5'-gcaggaacagttggccataagc-3'; SEQ ID NO: 60). For each mutation, two separate PCRs were performed, each using a perfectly complementary primer (BamHI-forw and SacI-rev) at the end of the sequence and a mutagenic primer. The resulting two overlapping fragments that contain the base substitution were then annealed together in a second PCR to amplify the complete mutated gene. Mutant 9-10A-A82L was isolated based on increased turnover of dimethyl ether. The properties of the resulting mutants, 9-10A-A82L and 9-10A-A328V can be observed in Tables 2 and 3. 9-10A-A82L demonstrated a decrease in catalytic rate for octane and propane, while it displayed a significant increase in the total turnover rate for octane and propane. It also showed a regioselectivity that favors the 4-alcohol product, at least for the octane, nonane, and decane products, in contrast to the 139-3 mutant.

On the other hand, the 9-10A-A328V mutant showed both a decrease in rate and turnover, as compared to the 9-10A mutant. However, this mutant displayed a high degree of regioselectivity, as shown in Table 2 and FIG. 2 (identified as A328V), especially for the 2-alcohol. The distribution of the products for the hydroxylation profiles can be seen in FIG. 2 and in Table 2. For example, as can be observed in Table 2, while the initial 139-3 mutant produced only 30% of its product of nonane in the 2-alcohol form, the 9-10A-A328V mutant produced 76% of its product in that form. Thus, the hydroxylation profile of this mutant is different from the 139-3 mutant.

Example 4

This example demonstrates how recombination of P450 BM-3 mutants can achieve desirable mutants, as shown in the $5^{th}$ step above. The last generation of mutants was created by recombination of mutants 139-1, J, 9-10A, 9-10A-A82L and 9-10A-A328V by DNA shuffling. (Stemmer, W. P. C. Nature 1994, 370, 389-391; Stemmer, W. P. C. Proc. Natl. Acad. Sci. USA 1994, 91, 10747-10751). Mutant 1-12G was isolated based on increased turnover of both dimethyl ether and propane. Mutant 1-12G has all of the mutations from the 9-10A-A328V mutant, with an additional mutation at position A82L. Interestingly, the rate of catalysis of this mutant is only 400 $min^{-1}$ and 20 $min^{-1}$ for octane and propane. However, the total turnover, as shown in Table 3 (7500 for octane and 6020 for propane), is much higher than for any of the other mutants. Additionally, as can be observed in FIG. 2, the bias towards the production of 2-alcohol products is much greater than for any of the other mutants as well, as high as 86% for decane. As discussed below, this mutant is also capable of hydroxylating ethane, something the wild type and 139-3 mutant are effectively unable to do. Again, the data in Table 2 demonstrate the altered hydroxylation profile of the 1-12G mutant. For example, where the hydroxylation profile of the 139-3 mutant for octane was 1, 61, 20, 17, and 5 percent for the 1-, 2-, 3-, 4-alcohols and ketone respectively, the same values for the 1-12G mutant were 5, 82, 11, 3, and 1. Not only has the hydroxylation profile changed, but the enzyme produces a larger percent of the 2-alcohol than it did before. Additionally, the hydroxylation profile of the enantiomeric products for octane has changed significantly between 139-3 and 1-12G, as the 139-3 results in 58(S), while 1-12G results in 39(R).

Example 5

This example demonstrates how one may express and purify the P450 BM-3 protein and relevant mutants. P450 BM-3 was expressed and purified as described previously. (Glieder et al., Nature Biotech., 20, 1135-1139 (2002)). The P450 BM-3 gene or mutants thereof, which include a silent mutation to introduce a SacI site 130 bp upstream of the end of the heme domain, was cloned behind the double tac promoter of the expression vector pCWori (pBM3_WT18-6) (Farinas, et al., Adv. Synth. Catal., 343:601-606 (2001)). *E. coli* DH5α, transformed with these plasmids, was used for expression of P450 BM-3 on a 500 mL scale as well as for expression in 96-well plates.

For protein production, supplemented terrific broth (TB) medium (600 mL, 100 μg/mL ampicillin, 50 μg/mL thymine) was inoculated with an overnight culture (1 mL) and incubated at 40° C. and 350 rpm. After 12 hours of incubation, the rotation speed was lowered to 200 rpm, α-aminolevulonic acid hydrochloride (ALA; 0.5 mM) was added and expression was induced by addition of isopropyl-β-D-thiogalactoside (IPTG; 1 mM). Cells were harvested 20 to 24 hours after induction by centrifugation. The enzymes were purified following published procedures. (See, Farinas et al. Adv. Synth. Catal., 343:601-606 (2001)). Enzyme concentration was measured in triplicated by CO-difference spectra. (Omura et al., *Journal of Biological Chemistry*, 239, 2370-2378 (1964)). The characteristics of the enzymes were then tested, as described in the following examples.

Example 6

This example demonstrates one method by which cell lysates can be prepared for high-throughput screening. Single colonies were picked and inoculated by a Qpix robot (Genetix, Beaverton, Oreg.) into 1-mL deep-well plates containing Luria-Bertani (LB) medium (350 μL, supplemented with 100 mg/mL ampicillin). The plates were incubated at 30° C., 250 rpm, and 80% relative humidity. After 24 hours, clones from this preculture were inoculated using a 96-pin replicator into 2-mL deep-well plates containing TB medium (400 μL, supplemented with 100 mg/mL ampicillin, 10 μM IPTG and 0.5 mM ALA). The cultures were grown at 30° C., 250 rpm, and 80% relative humidity for another 24 hours. Cells were then pelleted and stored frozen at −20° C. until they were resuspended in 500 μL 0.1 M phosphate buffer (0.1 M, pH=8, 500 μL, containing 0.5 mg/mL lysozyme, 2 Units/mL DnaseI, and 10 mM $MgCl_2$). After 60 min at 37° C., the lysates were centrifuged and the supernatant was diluted for activity measurements in 96 well microtiter plates, thus preparing the cell lysates for screening, as described in the next example.

Example 7

This example demonstrates methods for the high-throughput determination of enzymatic activity. The first mutant library was screened for NADPH depletion using propane as substrate. 170 μL of phosphate buffer (0.1 M, pH 8.0), saturated with propane was added to 30 uL of *E. coli* supernatant. The reaction was initiated by addition of 50 uL NADPH (0.8 mM and NAPDH oxidation was monitored at 340 nm for five min using a Spectramax Plus microtiter plate reader (Molecular Devices, Sunnyvale, Calif.).

The second library was additionally screened for NADP+ formation using propane as substrate as described earlier. (Glieder et al., *Nature Biotech.*, 20:1135-1139 (2002); Tsotsou et al. *Biosens. Bioelectron.*, 17, 119-131 (2002)). In brief, residual NADPH was destroyed with acid after an appropriate amount of time followed by conversion of $NADP^+$ to a highly fluorescent alkali product at high pH which was then measured fluorometrically. The results of the screens were used to select the J mutant and 9-10A mutant discussed above.

Example 8

This example demonstrates direct methods for the high-throughput determination of enzymatic activity. For direct measurement of product formation a screen based on the demethylation of dimethyl ether was used in the later generations. To 30 μL of *E. coli* supernatant, 120 μL of phosphate buffer (0.1 M, pH-8) saturated with dimethyl ether was added. After 2 min of incubation at room temperature NADPH (50 μL, 1.0 mM) was added and NADPH depletion was monitored as previously described. Purpald (168 mM in 2 M NaOH) was added 15 min after initiating the reaction to form a purple product with formaldehyde, generated after demethylation of the substrate. The purple color was read approximately 15 min later at 500 nm using a Spectramax Plus microtiter plate reader (Molecular Devices, Sunnyvale, Calif.). The results demonstrated that the third round of mutagenesis did not produce a mutant with improved results.

Example 9

This example demonstrates one method by which one can determine the enzyme kinetics of an enzyme. The enzymes were purified and quantified as described above. Initial rates of NADPH consumption were measured at 25° C. in a BioSpec-1601 UV/VIS spectrophotometer (Shimadzu, Columbia, Md.). For the liquid alkanes, substrate stock solutions in ethanol (10 μL) were added to the protein solution (100 nM, final concentration) and incubated for 2 min before initiating the reaction by addition of 200 μL NADPH (0.8 mM) and the absorption at 340 nm was monitored. Rates for any given substrate concentration were determined in triplicate. Results are shown in Table 3. The 9-10A mutant has the highest rate, while the 1-12G mutant has the lowest rate.

Example 10

This example demonstrates one method by which one can determine if the enzyme is capable of alkane hydroxylation reactions. Reactions with the liquid alkanes hexane, heptane, octane, nonane, and decane were performed in closed 20 mL scintillation vials and stirred at low speed using magnetic stirring bars. In a typical reaction, purified protein (or cell lyse) was added to 4.45 mL of 0.1 M potassium phosphate buffer pH=8.0 such that the total protein concentration equaled 50 nM. The substrates were added to this solution as 50 μL of 400 mM ethanol solutions to vive 4 mM total substrate and 1% ethanol. After a few seconds, 500 μL of 5mM NADPH in 0.1 M potassium phosphate buffer pH=8.0 was added to the reaction and the vial was capped. After 1-2 hours of stirring at room temperature, a 1.5 mL aliquot of the reaction was removed from the vial and quenched with 300 μL of chloroform in a 2 mL microcentrifuge tube. An internal standard containing 15 μL of 100 mM 1-pentanol or 3-octanol was added to the tube. The tube was vortexed and then centrifuged at 14,000 rpm for 2 minutes in a microcentrifuge. The chloroform layer was removed with a pipet and analyzed by gas chromatography for total turnover numbers and product distributions. Control reactions were performed by repeating these steps without the addition of substrate and revealed no background levels of these specific products. The samples were analyzed as described below.

Example 11

Figure 5A:
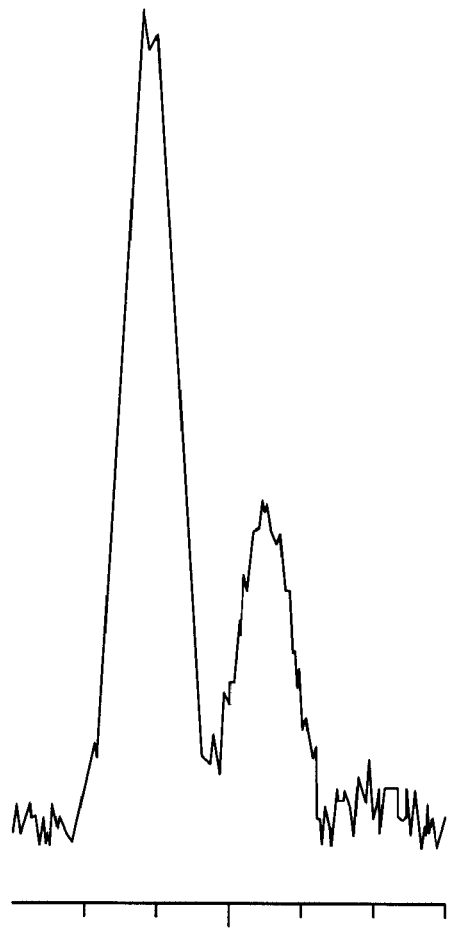
FIG. 5A is a GC/FID analysis of the (−)-menthyl carbonate diastereomers of the 2-octanol produced by 9-10A-A328V BM-3 catalyzed alkane oxidation.
Figure 5B:
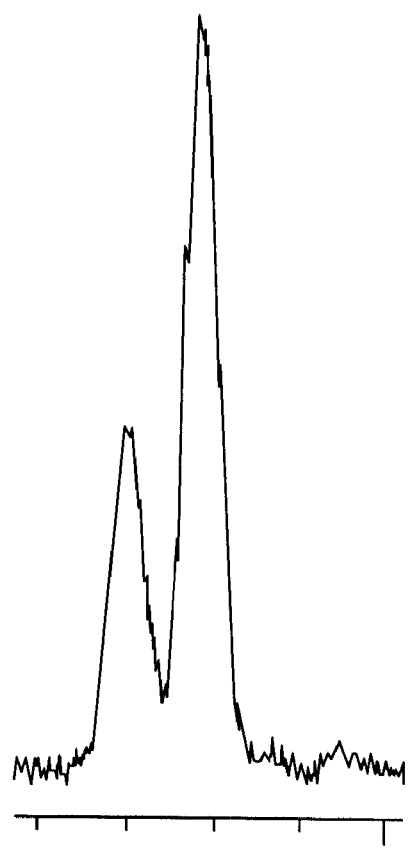
FIG. 5B is a GC/FID analysis of the (−)-menthyl carbonate diastereomers of the 2-octanol produced by 1-12G BM-3 catalyzed alkane oxidation.

This example demonstrates one method by which a chiral analysis of the products produced herein may be performed. Chiral analysis of liquid alkane hydroxylation products was performed with a slight modification of an existing method, starting with extracting 9 mL alkane reactions (using the reaction conditions above) with 2 mL methylene chloride in a 15 mL centrifuge tube (Westley et al., *J. Org. Chem.*, 33, 3978-3980 (1968)). After centrifugation at 4000 rpm for 15 minutes, the organic layer was removed with a pipet and dried over a small amount of anhydrous magnesium sulfate. The magnesium sulfate was removed by filtration, and 1 μL of pyridine and 2.5 μL (−)-menthyl chloroformate was added. After one hour, 1 mL of deionized water was added to the reaction. After vortexing and letting the layers separate, the organic phase was removed with a pipet and dried with anhydrous magnesium sulfate. The drying agent was again removed with a pipet filter and the remaining solution analyzed by gas chromatography. Control reactions were performed by repeating these steps without the addition of substrate and revealed no background levels of these specific products. Results are summarized in Table 2 and in FIGS. 2A-2E. As can be observed in Table2, which demonstrates that while the 9-10A-A328V mutant was biased in its production of S octane and R hexane and R heptane, the 1-12G mutant was biased in its production of the R enantiomer regardless of the initial substrate used. The data comparing the products from 9-10A-A328V and 1-12G can be observed in FIGS. 5A and 5B respectively. FIG. 5 shows a graph from a GC analysis of the (−)-menthyl carbonate diasteroemers of the 2-octanol produced by mutant BM-3 catalyzed alkane oxidation. S-2-octanol elutes at 18.4 (18.393 and 18.410) minutes, R-2-octanol elutes at 18.6 (18.553 and 18.575) minutes.

Example 12

This example demonstrates one method by which propane hydroxylation may be performed and monitored. Propane hydroxylation reactions were performed in 25 mL Schlenk flasks and no co-solvent was used in the reaction. In a typical reaction, enzyme (either purified or in cell lysate) was added to 4.5 mL of propane saturated 0.1M potassium phosphate buffer pH=8.0 to a final concentration of 500-100 mM. To this mixture, 500 μL of NADPH-regeneration system containing 1 mM NADP$^+$, 100 mM sodium isocitrate, and 20 Units/mL isocitrate dehydrogenase was quickly added. The flask was topped with a balloon filled with equal amounts of propane and dioxygen. After stirring for two hours at room temperature, the propane hydroxylation products were derivatized to alkyl nitrites using a published method. (Nguyen et al., *Analytical Sciences*, 17, 639-643 (2001)). To the reaction mixture, 0.3 g of sodium nitrite and 2 mL 10 μM chloroform in hexane was added and the mixture was cooled on ice. While on ice, 0.2 mL concentrated sulfuric acid was added. The flask was stoppered with a rubber stopper and stirred on ice for 15 minutes. The reaction was rinsed into a separatory funnel with 20 mL of deionized water. The organic phase was washed twice with 20 mL of water and analyzed by gas chromatography. Control reactions were performed by repeating these steps without the addition of substrate to correct for background levels of propanol. Results are summarized in Table 3.

Example 13

This example demonstrates how the mutant enzymes described herein can be useful in whole cell reactions. The procedure for whole cell reactions of *E. coli* (DH5α) overexpressing mutants 9-10A-A328V and 1-12G was similar to Withholt's published method. (Schneider et al., *Tetrahedron Asymmetry*, 9, 2833-2844 (1998)). An overnight culture of cells (in 3 mL LB with 100 μg/mL ampicillin) was used to inoculate 75 mL of M9 minimal medium containing 0.5% w/v glucose, 0.2 mM calcium chloride, 5 mM magnesium sulfate, and 100 μg/mL ampicillin. The culture was then shaken for 24 hours at 37° C. and 250 rpm. The cells were collected by centrifugation at 3500 rpm for 10 minutes and resuspended in 20 mL of 0.2M potassium phosphate buffer pH-7.4 containing 0.5% glucose, 100 μg/mL ampicillin, 1 mM IPTG, and 0.5 mM α-aminolevulonic acid, 5 mM alkane (from a 500 mM stock of alkane in dimethyl sulfoxide). This mixture was shaken for 8 hours at 37° C. and 250 rpm. Product distributions were measured by gas chromatography after extracting this culture with 1 mL of chloroform. Chiral analysis of the reaction products was performed by extracting the culture with 2 mL of methylene chloride and derivatizing the organic layer with (−)-menthyl chloroformate. The results are demonstrated in FIG. 6A and FIG. 6B for the resulting products from the purified protein and the whole cell respectively. 3-octanol elutes at about 7.7 minutes, 2-octanol elutes at about 7.8 minutes, and 1 octanol elutes at about 9.0 minutes.

Example 14

This example demonstrates how gas chromatography can be used for identification and quantification of analytes. Identification and quantification of analytes were performed using purchased standards and 5 point calibration curves with internal standards. All analyses were injected at a volume of 1.0 μL and performed at least in triplicate. Analysis of hydroxylation products were performed on a Hewlett Packard 5890 Series II Plus gas chromatograph with both a flame ionization (FID) and electron capture detector (ECD) and fitted with a HP-7673 autosampler system. Direct analysis of hexane, heptane, octane, nonane, and decane hydroxylation products was performed on an HP-5 capillary column (crosslinked 5% phenyl methyl siloxane, 30 m length, 0.32 mm ID, 0.25 μm film thickness) connected to the FID detector. A typical temperature program for separating the alcohol products is 250° C. injector, 300° C. detector, 50° C. oven for 3 minutes, 10° C./minute to 200° C., 25° C./minute to 250° C., 250° C. for 3 minutes. The (−)-menthyl chloroformate derivatized chiral products were separated as diastereomers on a CycloSil-B chiral capillary column (Agilent Technologies, 30 m length, 0.32 mm ID, 0.25 μm film thickness) connected to the FID detector. Each pair of diastereomers required a different temperature program to fully resolve the pair, but a typical program is as follows: chiral heptanol analysis—250° C. injector, 300° C. detector, 10° C. oven for 1 minute, then 10° C./minute gradient to 180° C., hold at 180° C. for 10 minutes, 10° C./minute gradient to 250° C., then 250° C. for 3 minutes. The propyl nitrite products were analyzed with an HP-1 capillary column (crosslinked 1% phenyl methyl siloxane, 30 m length, 0.32 mm ID, 0.25 μm film thickness) connected to an ECD detector. The temperature program for separating 1- and 2-propyl nitrites was 250° C. injector, 300° C. detector, 30° C. oven for 3 minutes, 20° C./minute gradient to 200° C., 200° C. for 5 minutes. Results can be observed in FIG. 2, FIG. 5, FIG. 6, and Tables 2 and 3.

Example 15

This example demonstrates that further rounds of directed evolution of the 9-10A-A328V and 1-12G biocatalysts will allow the enzyme to support alkane hydroxylation that is even more enantioselective. For example, chiral lipases and alcohol dehydrogenases are available that selectively convert one 2-alcohol enantiomer over the other. These enzymes can be coupled to a screening protocol to screen for mutant BM-3 enzymes that form one enantiomeric alcohol product over another. For example, lipases that are capable of enantioselective transesterification reactions in which a single enantiomer of an alcohol, such as S-2-octanol, can be used to replace the alcohol component of an ester substrate. The replaced alcohol component in the ester can be a chromophore, such as p-nitrophenolate, or can be reacted with a dye to form a chromophore, such as vinyl alcohol. This will then allow the presence of the chiral alcohol product to be detected colorimetrically in the presence of the lipase and the ester substrate, as discussed in greater detail in Konarzycka-Bessier et al., Angewandte Chemie International English Edition, 42(12): 1418-1420 (2003). Alternatively, alcohol dehydrogenases that selectively oxidize chiral alcohols can be incorporated into a coupled screening system.

Incorporation by Reference

All references cited herein, including patents, patent applications, papers, text books, and the like, and the references cited therein, to the extent that they are not already, are hereby incorporated herein by reference in their entirety.

Equivalents

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An isolated mutant cytochrome P450 *Bacillus megaterium* 3 (BM-3) enzyme comprising the amino acid sequence of SEQ ID NO:2, except that a leucine is at position 82.

2. The isolated mutant P450 enzyme of claim 1, wherein the mutant further consists of at least one mutation selected from the group consisting of: V78A, T175I, A184V, H236Q, E252G, R255S, and L353V, and combinations thereof.

3. The isolated mutant P450 enzyme of claim 2, wherein the mutation is a V78A mutation.

4. The isolated mutant P450 enzyme of claim 2, wherein the mutant further consists of V78A, T175I, A184V, H236Q, E252G, R255S, and L353V mutations.

5. The isolated mutant P450 enzyme of claim 1, wherein the mutant further consists of a mutation selected from the group consisting of: V78A, T175I, A184V, H236Q, E252G, R255S, L353V, H138Y, V178I, and A295T, and combinations thereof.

6. The isolated mutant P450 enzyme of claim 1, wherein said enzyme further consists of an amino acid mutation selected from the group consisting of: R47C, K94I, P142S, F205C, S226R, and A290V, and combinations thereof.

7. The isolated mutant P450 enzyme of claim 1, further consisting of a mutation selected from the group consisting of: A328V, R47C, K94I, P142S, F205C, F87I, T88C, S226R, and A290V, and combinations thereof.

8. The isolated mutant P450 enzyme of claim 1, further consisting of a mutation selected from the group consisting of: R47C, F87I, and A328V, and combinations thereof.

9. The isolated mutant P450 enzyme of claim 8, wherein the enzyme includes a mutation of A328V.

10. The isolated mutant P450 enzyme of claim 1, further consisting of a mutation selected from the group consisting of: A328V, R47C, K94I, P142S, F205C, S226R, and A290V.

11. The isolated mutant P450 enzyme of claim 1, further consisting of the following mutations: A328V, R47C, K94I, P142S, F205C, S226R, and A290V.

12. The isolated mutant P450 enzyme of claim 11, wherein the enzyme includes a V78A mutation.

13. The isolated mutant P450 enzyme of claim 12, further consisting of T175I, A184V, H236Q, E252G, R255S, and L353V mutations.

14. An isolated mutant P450 enzyme comprising at least 90% identity to SEQ ID NO:2 and having a A82L point mutation and can hydroxylate an alkane.

15. The isolated mutant P450 enzyme of claim 14, wherein the P450 enzyme is at least 95% identical to the sequence in SEQ ID NO:2, and can hydroxylate an alkane.

16. The isolated mutant P450 enzyme of claim 14 that has a higher degree of regioselectivity for the hydroxylation of octane than the wild-type and further consisting of a V78A, H138Y, T175I, V178I, A184V, H236Q, E252G, R255S, A295T and L353V mutation in SEQ ID NO:2, wherein the P450 mutant is at least 70% selective for one regioisomer over the other.

17. The isolated mutant P450 enzyme of claim 16, wherein the regioselectivity of the mutant is at least 80% selective for one regioisomer over the other.

18. The isolated mutant P450 enzyme of claim 16, wherein the mutant P450 is a P450 BM-3.

19. An isolated mutant P450 enzyme having at least 90% sequence identity to the P450 enzyme of SEQ ID NO:2, wherein said enzyme comprises a leucine at position 82 of SEQ ID NO: 2, wherein the mutant enzyme has an enantioselectivity that allows for hydroxylation of a substrate to occur in a R configuration.

20. The isolated mutant P450 of claim 19, wherein the substrate is octane.

21. The isolated mutant P450 of claim 19, wherein the P450 enzyme of SEQ ID NO:2 is obtained from a *Bacillus megaterium* 3 (BM-3).

22. A method of hydroxylating an decane, nonane, octane, heptane, hexane, pentane, propane, or ethane, said method comprising:
    providing an isolated mutant P450 enzyme of claim 1; and
    contacting said isolated mutant P450 with a decane, nonane, octane, heptane, hexane, pentane, propane, or ethane.

23. The method of claim 22, wherein the hydroxylation occurs in a regioselective manner.

24. The method of claim 22, wherein the hydroxylation occurs in an enantioselective manner.

25. The method of claim 22, wherein the isolated mutant P450 hydroxylates said alkane with a turnover number of more than 100.

26. The method of claim 22, wherein the alkane is an octane and wherein the isolated mutant P450 hydroxylates said octane with a turnover number of more than 1000.

* * * * *

SEQUENCE LISTING

<160> NUMBER OF SEQ ID NOS: 60

<210> SEQ ID NO 1
<211> LENGTH: 8101
<212> TYPE: DNA
<213> ORGANISM: Bacillus megaterium

<400> SEQUENCE: 1

```
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aagcgcttaa atttgtacgt     240
gattttgcag gagacgggtt atttacaagc tggacgcatg aaaaaaattg gaaaaaagcg     300
cataatatct tacttccaag cttcagtcag caggcaatga aaggctatca tgcgatgatg     360
gtcgatatcg ccgtgcagct tgttcaaaag tgggagcgtc taaatgcaga tgagcatatt     420
gaagtaccgg aagacatgac acgtttaacg cttgataaa ttggtctttg cggctttaac     480
tatcgcttta acagcttta ccgagatcag cctcatccat ttattacaag tatggtccgt     540
gcactggatg aagcaatgaa caagctgcag cgagcaaatc cagacgaccc agcttatgat     600
gaaaacaagc gccagtttca agaagatatc aaggtgatga acgacctagt agataaaatt     660
attgcagatc gcaaagcaag cggtgaacaa agcgatgatt tattaacgca tatgctaaac     720
ggaaaagatc cagaaacggg tgagccgctt gatgacgaga acattcgcta tcaaattatt     780
acattcttaa ttgcgggaca cgaaacaaca agtggtcttt tatcatttgc gctgtatttc     840
ttagtgaaaa atccacatgt attacaaaaa gcagcagaag aagcagcacg agttctagta     900
```

```
gatcctgttc caagctacaa acaagtcaaa cagcttaaat atgtcggcat ggtcttaaac     960
gaagcgctgc gcttatggcc aactgctcct gcgttttccc tatatgcaaa agaagatacg    1020
gtgcttggag gagaatatcc tttagaaaaa ggcgacgaac taatggttct gattcctcag    1080
cttcaccgtg ataaaacaat ttggggagac gatgtggaag agttccgtcc agagcgtttt    1140
gaaaatccaa gtgcgattcc gcagcatgcg tttaaaccgt ttggaaacgg tcagcgtgcg    1200
tgtatcggtc agcagttcgc tcttcatgaa gcaacgctgg tacttggtat gatgctaaaa    1260
cactttgact ttgaagatca tacaaactac gagctcgata ttaaagaaac tttaacgtta    1320
aaacctgaag gctttgtggt aaaagcaaaa tcgaaaaaaa ttccgcttgg cggtattcct    1380
tcacctagca ctgaacagtc tgctaaaaaa gtacgcaaaa aggcagaaaa cgctcataat    1440
acgccgctgc ttgtgctata cggttcaaat atgggaacag ctgaaggaac ggcgcgtgat    1500
ttagcagata ttgcaatgag caaaggattt gcaccgcagg tcgcaacgct tgattcacac    1560
gccggaaatc ttccgcgcga aggagctgta ttaattgtaa cggcgtctta taacggtcat    1620
ccgcctgata acgcaaagca atttgtcgac tggttagacc aagcgtctgc tgatgaagta    1680
aaaggcgttc gctactccgt atttggatgc ggcgataaaa actgggctac tacgtatcaa    1740
aaagtgcctg cttttatcga tgaaacgctt gccgctaaag gggcagaaaa catcgctgac    1800
cgcggtgaag cagatgcaag cgacgacttt gaaggcacat atgaagaatg gcgtgaacat    1860
atgtggagtg acgtagcagc ctactttaac ctcgacattg aaaacagtga agataataaa    1920
tctactcttt cacttcaatt tgtcgacagc gccgcggata tgccgcttgc gaaaatgcac    1980
ggtgcgtttt caacgaacgt cgtagcaagc aaagaacttc aacagccagg cagtgcacga    2040
agcacgcgac atcttgaaat tgaacttcca aaagaagctt cttatcaaga aggagatcat    2100
ttaggtgtta ttcctcgcaa ctatgaagga atagtaaacc gtgtaacagc aaggttcggc    2160
ctagatgcat cacagcaaat ccgtctggaa gcagaagaag aaaaattagc tcatttgcca    2220
ctcgctaaaa cagtatccgt agaagagctt ctgcaatacg tggagcttca agatcctgtt    2280
acgcgcacgc agcttcgcgc aatggctgct aaaacggtct gcccgccgca taagtagag     2340
cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa gaattcatcg atgataagct gtcaaacatg    3180
agcagatctg agcccgccta atgagcgggc ttttttttca gatctgcttg aagacgaaag    3240
```

```
ggcctcgtga tacgcctatt tttataggtt aatgtcatga taataatggt ttcttagcgt    3300
caaagcaacc atagtacgcg ccctgtagcg gcgcattaag cgcggcgggt gtggtggtta    3360
cgcgcagcgt gaccgctaca cttgccagcg ccctagcgcc cgctcctttc gctttcttcc    3420
cttcctttct cgccacgttc gccggctttc cccgtcaagc tctaaatcgg ggctcccctt    3480
tagggttccg atttagtgct ttacggcacc tcgaccccaa aaacttgat ttgggtgatg     3540
gttcacgtag tgggccatcg ccctgataga cggttttttcg ccctttgacg ttggagtcca   3600
cgttctttaa tagtggactc ttgttccaaa ctggaacaac actcaaccct atctcgggct    3660
attcttttga tttataaggg attttgccga tttcggccta ttggttaaaa aatgagctga    3720
tttaacaaaa atttaacgcg aattttaaca aaatattaac gtttacaatt tcaggtggca    3780
cttttcgggg aaatgtgcgc ggaacccta tttgtttatt tttctaaata cattcaaata    3840
tgtatccgct catgagacaa taaccctgat aaatgcttca ataatattga aaaggaaga    3900
gtatgagtat tcaacatttc cgtgtcgccc ttattccctt ttttgcggca ttttgccttc    3960
ctgttttgc tcacccagaa acgctggtga agtaaaaga tgctgaagat cagttgggtg     4020
cacgagtggg ttacatcgaa ctggatctca acagcggtaa gatccttgag agttttcgcc   4080
ccgaagaacg ttttccaatg atgagcactt ttaaagttct gctatgtggc gcggtattat   4140
cccgtgttga cgccgggcaa gagcaactcg gtcgccgcat acactattct cagaatgact   4200
tggttgagta ctcaccagtc acagaaaagc atcttacgga tggcatgaca gtaagagaat   4260
tatgcagtgc tgccataacc atgagtgata acactgcggc caacttactt ctgacaacga   4320
tcggaggacc gaaggagcta accgcttttt tgcacaacat gggggatcat gtaactcgcc   4380
ttgatcgttg ggaaccggag ctgaatgaag ccataccaaa cgacgagcgt gacaccacga   4440
tgcctgcagc aatggcaaca acgttgcgca aactattaac tggcgaacta cttactctag   4500
cttcccggca acaattaata gactggatgg aggcggataa agttgcagga ccacttctgc   4560
gctcggccct tccggctggc tggtttattg ctgataaatc tggagccggt gagcgtgggt   4620
ctcgcggtat cattgcagca ctggggccag atggtaagcc ctcccgtatc gtagttatct   4680
acacgacggg gagtcaggca actatggatg aacgaaatag acagatcgct gagataggtg   4740
cctcactgat taagcattgg taactgtcag accaagttta ctcatatata ctttagattg   4800
atttaaaact tcatttttaa tttaaaagga tctaggtgaa gatcctttt gataatctca    4860
tgaccaaaat cccttaacgt gagttttcgt tccactgagc gtcagacccc gtagaaaaga   4920
tcaaaggatc ttcttgagat cctttttttc tgcgcgtaat ctgctgcttg caaacaaaaa   4980
aaccaccgct accagcggtg gtttgtttgc cggatcaaga gctaccaact ctttttccga   5040
aggtaactgg cttcagcaga gcgcagatac caaatactgt ccttctagtg tagccgtagt   5100
taggccacca cttcaagaac tctgtagcac cgcctacata cctcgctctg ctaatcctgt   5160
taccagtggc tgctgccagt ggcgataagt cgtgtcttac cgggttggac tcaagacgat   5220
agttaccgga taaggcgcag cggtcgggct gaacgggggg ttcgtgcaca gcccagct    5280
tggagcgaac gacctacacc gaactgagat acctacagcg tgagctatga aaagcgcca    5340
cgcttcccga agggagaaag gcggacaggt atccggtaag cggcagggtc ggaacaggag   5400
agcgcacgag ggagcttcca gggggaaacg cctggtatct ttatagtcct gtcgggtttc   5460
gccacctctg acttgagcgt cgatttttgt gatgctcgtc agggggcgg agcctatgga    5520
aaaacgccag caacgcggcc ttttacggt tcctggcctt ttgctggcct tttgctcaca    5580
tgttctttcc tgcgttatcc cctgattctg tggataaccg tattaccgcc tttgagtgag   5640
```

```
ctgataccgc tcgccgcagc cgaacgaccg agcgcagcga gtcagtgagc gaggaagcgg    5700
aagagcgcct gatgcggtat tttctcctta cgcatctgtg cggtatttca caccgcatat    5760
atggtgcact ctcagtacaa tctgctctga tgccgcatag ttaagccagt atacactccg    5820
ctatcgctac gtgactgggt catggctgcg ccccgacacc cgccaacacc cgctgacgcg    5880
ccctgacggg cttgtctgct cccggcatcc gcttacagac aagctgtgac cgtctccggg    5940
agctgcatgt gtcagaggtt ttcaccgtca tcaccgaaac gcgcgaggca gaacgccatc    6000
aaaaataatt cgcgtctggc cttcctgtag ccagctttca tcaacattaa atgtgagcga    6060
gtaacaaccc gtcggattct ccgtgggaac aaacggcgga ttgaccgtaa tgggataggt    6120
tacgttggtg tagatgggcg catcgtaacc gtgcatctgc cagtttgagg ggacgacgac    6180
agtatcggcc tcaggaagat cgcactccag ccagctttcc ggcaccgctt ctggtgccgg    6240
aaaccaggca agcgccatt cgccattcag gctgcgcaac tgttgggaag ggcgatcggt    6300
gcgggcctct tcgctattac gccagctggc gaaagggggga tgtgctgcaa ggcgattaag    6360
ttgggtaacg ccagggtttt cccagtcacg acgttgtaaa acgacggcca gtgaatccgt    6420
aatcatggtc atagctgttt cctgtgtgaa attgttatcc gctcacaatt ccacacaaca    6480
tacgagccgg aagcataaag tgtaaagcct ggggtgccta atgagtgagc taactcacat    6540
taattgcgtt gcgctcactg cccgctttcc agtcgggaaa cctgtcgtgc cagctgcatt    6600
aatgaatcgg ccaacgcgcg gggagaggcg gtttgcgtat tgggcgccag ggtggttttt    6660
cttttcacca gtgagacggg caacagctga ttgcccttca ccgcctggcc ctgagagagt    6720
tgcagcaagc ggtccacgct ggtttgcccc agcaggcgaa aatcctgttt gatggtggtt    6780
aacggcggga tataacatga gctgtcttcg gtatcgtcgt atcccactac cgagatatcc    6840
gcaccaacgc gcagcccgga ctcggtaatg gcgcgcattg cgcccagcgc catctgatcg    6900
ttggcaacca gcatcgcagt gggaacgatg ccctcattca gcatttgcat ggtttgttga    6960
aaaccggaca tggcactcca gtcgccttcc cgttccgcta tcggctgaat ttgattgcga    7020
gtgagatatt tatgccagcc agccagacgc agacgcgccg agacagaact taatgggccc    7080
gctaacagcg cgatttgctg gtgacccaat gcgaccagat gctccacgcc cagtcgcgta    7140
ccgtcttcat gggagaaaat aatactgttg atgggtgtct ggtcagagac atcaagaaat    7200
aacgccggaa cattagtgca ggcagcttcc acagcaatgg catcctggtc atccagcgga    7260
tagttaatga tcagcccact gacgcgttgc gcgagaagat tgtgcaccgc cgctttacag    7320
gcttcgacgc cgcttcgttc taccatcgac accaccacgc tggcacccag ttgatcggcg    7380
cgagatttaa tcgccgcgac aatttgcgac ggcgcgtgca gggccagact ggaggtggca    7440
acgccaatca gcaacgactg tttgcccgcc agttgttgtg ccacgcggtt gggaatgtaa    7500
ttcagctccg ccatcgccgc ttccactttt tcccgcgttt tcgcagaaac gtggctggcc    7560
tggttcacca cgcgggaaac ggtctgataa gagacaccgg catactctgc gacatcgtat    7620
aacgttactg gtttcacatt caccaccctg aattgactct cttccgggcg ctatcatgcc    7680
ataccgcgaa aggttttgcg ccattcgatg gtgtcctggc acgacaggtt tcccgactgg    7740
aaagcgggca gtgagcgcaa cgcaattaat gtgagttagc tcactcatta ggcaccccag    7800
gctttacact ttatgcttcc ggctcgtata atgtgtggaa ttgtgagcgg ataacaattt    7860
cacacaggaa acaggatcga tccatcgatg agcttactcc ccatcccct gttgacaatt    7920 aatcatcggc tcgtataatg tgtggaattg tgagcggata acaatttcac acaggaaaca    7980
```

```
ggatcagctt actccccatc ccctgttga caattaatca tcggctcgta taatgtgtgg      8040
aattgtgagc ggataacaat ttcacacagg aaacaggatc catcgatgct taggaggtca     8100
t                                                                    8101
```

<210> SEQ ID NO 2
<211> LENGTH: 1048
<212> TYPE: PRT
<213> ORGANISM: Bacillus megaterium

<400> SEQUENCE: 2

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
                 20                  25                  30

Ala Asp Glu Leu Gly Glu Ile Phe Lys Phe Glu Ala Pro Gly Arg Val
             35                  40                  45

Thr Arg Tyr Leu Ser Ser Gln Arg Leu Ile Lys Glu Ala Cys Asp Glu
         50                  55                  60

Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350
```

```
Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
        610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
        690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765
```

```
Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 3
<211> LENGTH: 3144
<212> TYPE: DNA
<213> ORGANISM: Bacillus megaterium

<400> SEQUENCE: 3
acaattaaag aaatgcctca gccaaaaacg tttggagagc ttaaaaattt accgttatta      60
aacacagata aaccggttca agctttgatg aaaattgcgg atgaattagg agaaatcttt    120
aaattcgagg cgcctggttg tgtaacgcgc tacttatcaa gtcagcgtct aattaaagaa    180
gcatgcgatg aatcacgctt tgataaaaac ttaagtcaag cgcttaaatt tgcacgtgat    240
tttcttggag acgggttatt tacaagctgg acgcatgaaa taaattggaa aaaagcgcat    300
aatatcttac ttccaagctt tagtcagcag gcaatgaaag ctatcatgc gatgatggtc    360 gatatcgccg tgcagcttgt tcaaaagtgg gagcgtctaa atgcagatga gcatattgaa    420
gtatcggaag acatgacacg tttaacgctt gatacaattg gtctttgcgg ctttaactat    480
cgctttaaca gcttttaccg agatcagcct catccattta ttataagtat ggtccgtgca    540
```

```
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat aacgcagat  gctaaacgga    720
aaagatccag aaacgggtga gccgcttgat gacgggaaca ttagctatca aattattaca    780
ttcttaattg cggacacga  aacaacaagt ggtcttttat catttgcgct gtatttctta    840
gtgaaaaatc cacatgtatt acaaaaagta gcagaagaag cagcacgagt tctagtagat    900
cctgttccaa gctacaaaca agtcaaacag cttaaatatg tcggcatggt cttaaacgaa    960
gcgctgcgct tatggccaac tgttcctgcg tttttcctat atgcaaaaga agatacggtg   1020
cttggaggag aatatccttt agaaaaaggc gacgaagtaa tggttctgat tcctcagctt   1080
caccgtgata aacaatttgg gggagacgat gtggaggagt tccgtccaga gcgttttgaa   1140
aatccaagtg cgattccgca gcatgcgttt aaaccgtttg gaaacggtca gcgtgcgtgt   1200
atcggtcagc agttcgctct tcatgaagca acgctggtac ttggtatgat gctaaaacac   1260
tttgactttg aagatcatac aaactacgag ctcgatatta agaaactttt aacgttaaaa   1320
cctgaaggct ttgtggtaaa agcaaaatcg aaaaaaattc cgcttggcgg tattccttca   1380
cctagcactg aacagtctgc taaaaaagta cgcaaaaagg cagaaaacgc tcataatacg   1440
ccgctgcttg tgctatacgg ttcaaatatg ggaacagctg aaggaacggc gcgtgattta   1500
gcagatattg caatgagcaa aggatttgca ccgcaggtcg caacgcttga ttcacacgcc   1560
ggaaatcttc cgcgcgaagg agctgtatta attgtaacgg cgtcttataa cggtcatccg   1620
cctgataacg caaagcaatt tgtcgactgg ttagaccaag cgtctgctga tgaagtaaaa   1680
ggcgttcgct actccgtatt tggatgcggc gataaaaact gggctactac gtatcaaaaa   1740
gtgcctgctt ttatcgatga aacgcttgcc gctaaggggg cagaaaacat cgctgaccgc   1800
ggtgaagcag atgcaagcga cgactttgaa ggcacatatg aagaatggcg tgaacatatg   1860
tggagtgacg tagcagccta ctttaacctc gacattgaaa acagtgaaga taataaatct   1920
actctttcac ttcaatttgt cgacagcgcc gcggatatgc cgcttgcgaa aatgcacggt   1980
gcgttttcaa cgaacgtcgt agcaagcaaa gaacttcaac agccaggcag tgcacgaagc   2040
acgcgacatc ttgaaattga acttccaaaa gaagcttctt atcaagaagg agatcattta   2100
ggtgttattc ctcgcaacta tgaaggaata gtaaaccgtg taacagcaag gttcggccta   2160
gatgcatcac agcaaatccg tctggaagca gaagaagaaa aattagctca tttgccactc   2220
gctaaaacag tatccgtaga agagcttctg caatacgtgg agcttcaaga tcctgttacg   2280
cgcacgcagc ttcgcgcaat ggctgctaaa acggtctgcc cgccgcataa agtagagctt   2340
gaagccttgc ttgaaaagca agcctacaaa gaacaagtgc tggcaaaacg tttaacaatg   2400
cttgaactgc ttgaaaaata cccggcgtgt gaaatgaaat tcagcgaatt tatcgccctt   2460
ctgccaagca tacgcccgcg ctattactcg atttcttcat cacctcgtgt cgatgaaaaa   2520
caagcaagca tcacggtcag cgttgtctca ggagaagcgt ggagcggata tggagaatat   2580
aaaggaattg cgtcgaacta tcttgccgag ctgcaagaag gagatacgat tacgtgcttt   2640
atttccacac cgcagtcaga atttacgctg ccaaaagacc ctgaaacgcc gcttatcatg   2700
gtcggaccgg gaacaggcgt cgcgccgttt agaggctttg tgcaggcgcg caaacagcta   2760
aaagaacaag gacagtcact tggagaagca catttatact tcggctgccg ttcacctcat   2820
gaagactatc tgtatcaaga agagcttgaa aacgcccaaa gcgaaggcat cattacgctt   2880
```

```
cataccgctt tttctcgcat gccaaatcag ccgaaaacat acgttcagca cgtaatggaa      2940
caagacggca agaaattgat tgaacttctt gatcaaggag cgcacttcta tatttgcgga      3000
gacggaagcc aaatggcacc tgccgttgaa gcaacgctta tgaaaagcta tgctgacgtt      3060
caccaagtga gtgaagcaga cgctcgctta tggctgcagc agctagaaga aaaaggccga      3120
tacgcaaaag acgtgtgggc tggg                                             3144
```

<210> SEQ ID NO 4
<211> LENGTH: 1048
<212> TYPE: PRT
<213> ORGANISM: Bacillus megaterium

<400> SEQUENCE: 4

```
Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Leu Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
           100                 105                 110

Lys Gly Tyr His Ala Met Met Val Asp Ile Ala Val Gln Leu Val Gln
       115                 120                 125

Lys Trp Glu Arg Leu Asn Ala Asp Glu His Ile Glu Val Ser Glu Asp
   130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Ala Phe Ser Leu Tyr Ala Lys
```

-continued

```
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Ile Trp Gly
            355                 360                 365
Asp Asp Val Glu Glu Phe Arg Pro Glu Arg Phe Glu Asn Pro Ser Ala
            370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
            405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
            435                 440                 445
Lys Ser Lys Lys Ile Pro Leu Gly Gly Ile Pro Ser Pro Ser Thr Glu
            450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
            485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
            515                 520                 525
Val Leu Ile Val Thr Ala Ser Tyr Asn Gly His Pro Pro Asp Asn Ala
            530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
            565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
            595                 600                 605
Phe Glu Gly Thr Tyr Glu Glu Trp Arg Glu His Met Trp Ser Asp Val
            610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
            645                 650                 655
Lys Met His Gly Ala Phe Ser Thr Asn Val Val Ala Ser Lys Glu Leu
            660                 665                 670
Gln Gln Pro Gly Ser Ala Arg Ser Thr Arg His Leu Glu Ile Glu Leu
            675                 680                 685
Pro Lys Glu Ala Ser Tyr Gln Glu Gly Asp His Leu Gly Val Ile Pro
            690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
            725                 730                 735
His Leu Pro Leu Ala Lys Thr Val Ser Val Glu Glu Leu Leu Gln Tyr
            740                 745                 750
```

-continued

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
        930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 5
<211> LENGTH: 3144
<212> TYPE: DNA
<213> ORGANISM: Bacillus megaterium

<400> SEQUENCE: 5
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgcttaaatt tgcacgtgat     240
tttgcaggag acgggttatt tacaagctgg acgcatgaaa taaattggaa aaaagcgcat     300
aatatcttac ttccaagctt tagtcagcag gcaatgaaag ctatcatgc gatgatggtc     360 gatatcgccg tgcagcttgt tcaaaagtgg gagcgtctaa atgcagatga gcatattgaa     420

```
gtatcggaag acatgacacg tttaacgctt gatacaattg gtctttgcgg ctttaactat      480
cgctttaaca gcttttaccg agatcagcct catccattta ttataagtat ggtccgtgca      540
ctggatgaag taatgaacaa gctgcagcga gcaaatccag acgacccagc ttatgatgaa      600
aacaagcgcc agtgtcaaga agatatcaag gtgatgaacg acctagtaga taaaattatt      660
gcagatcgca aagcaagggg tgaacaaagc gatgatttat aacgcagat gctaaacgga       720
aaagatccag aaacgggtga gccgcttgat gacgggaaca ttagctatca aattattaca      780
ttcttaattg cgggacacga aacaacaagt ggtcttttat catttgcgct gtatttctta      840
gtgaaaaatc cacatgtatt acaaaaagta gcagaagaag cagcacgagt tctagtagat      900
cctgttccaa gctacaaaca agtcaaacag cttaaatatg tcggcatggt cttaaacgaa      960
gcgctgcgct tatggccaac tgctcctgcg ttttccctat atgcaaaaga agatacggtg     1020
cttggaggag aatatccttt agaaaaaggc gacgaagtaa tggttctgat tcctcagctt     1080
caccgtgata aacaatttg gggagacgat gtggaggagt tccgtccaga gcgttttgaa      1140
aatccaagtg cgattccgca gcatgcgttt aaaccgtttg aaacggtca gcgtgcgtgt      1200
atcggtcagc agttcgctct tcatgaagca acgctggtac ttggtatgat gctaaaacac     1260
tttgactttg aagatcatac aaactacgag ctcgatatta agaaactttt aacgttaaaa     1320
cctgaaggct ttgtggtaaa agcaaaatcg aaaaaaattc cgcttggcgg tattccttca     1380
cctagcactg aacagtctgc taaaaaagta cgcaaaaagg cagaaaacgc tcataatacg     1440
ccgctgcttg tgctatacgg ttcaaatatg ggaacagctg aaggaacggc gcgtgattta     1500
gcagatattg caatgagcaa aggatttgca ccgcaggtcg caacgcttga ttcacacgcc     1560
ggaaatcttc cgcgcgaagg agctgtatta attgtaacgg cgtcttataa cggtcatccg     1620
cctgataacg caaagcaatt tgtcgactgg ttagaccaag cgtctgctga tgaagtaaaa     1680
ggcgttcgct actccgtatt tggatgcggc gataaaaact gggctactac gtatcaaaaa     1740
gtgcctgctt ttatcgatga aacgcttgcc gctaaggggg cagaaaacat cgctgaccgc     1800
ggtgaagcag atgcaagcga cgactttgaa ggcacatatg aagaatggcg tgaacatatg     1860
tggagtgacg tagcagccta ctttaacctc gacattgaaa acagtgaaga taataaatct     1920
actctttcac ttcaatttgt cgacagcgcc gcggatatgc cgcttgcgaa aatgcacggt     1980
gcgttttcaa cgaacgtcgt agcaagcaaa gaacttcaac agccaggcag tgcacgaagc     2040
acgcgacatc ttgaaattga acttccaaaa gaagcttctt atcaagaagg agatcattta     2100
ggtgttattc ctcgcaacta tgaaggaata gtaaaccgtg taacagcaag gttcggccta     2160
gatgcatcac agcaaatccg tctggaagca gaagaagaaa aattagctca tttgccactc     2220
gctaaaacag tatccgtaga agagcttctg caatacgtgg agcttcaaga tcctgttacg     2280
cgcacgcagc ttcgcgcaat ggctgctaaa acggtctgcc cgccgcataa agtagagctt     2340
gaagccttgc ttgaaaagca agcctacaaa gaacaagtgc tggcaaaacg tttaacaatg     2400
cttgaactgc ttgaaaaata cccggcgtgt gaaatgaaat tcagcgaatt tatcgcccct     2460
ctgccaagca tacgcccgcg ctattactcg atttcttcat cacctcgtgt cgatgaaaaa     2520
caagcaagca tcacggtcag cgttgtctca ggagaagcgt ggagcggata tggagaatat     2580
aaaggaattg cgtcgaacta tcttgccgag ctgcaagaag gagatacgat tacgtgcttt     2640
atttccacac cgcagtcaga atttacgctg ccaaaagacc ctgaaacgcc gcttatcatg     2700
gtcggaccgg gaacaggcgt cgcgccgttt agaggctttg tgcaggcgcg caaacagcta     2760
```

```
aaagaacaag gacagtcact tggagaagca catttatact tcggctgccg ttcacctcat    2820
gaagactatc tgtatcaaga agagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 6
<211> LENGTH: 1048
<212> TYPE: PRT
<213> ORGANISM: Bacillus megaterium

<400> SEQUENCE: 6

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300
```

-continued

```
Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Glu Lys Leu Ala
```

-continued

```
              725                 730                 735
His Leu Pro Leu Ala Lys Thr Val Ser Val Glu Glu Leu Leu Gln Tyr
            740                 745                 750
Val Glu Leu Gln Asp Pro Val Thr Arg Thr Gln Leu Arg Ala Met Ala
            755                 760                 765
Ala Lys Thr Val Cys Pro Pro His Lys Val Glu Leu Glu Ala Leu Leu
            770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
            820                 825                 830
Ser Ser Pro Arg Val Asp Glu Lys Gln Ala Ser Ile Thr Val Ser Val
            835                 840                 845
Val Ser Gly Glu Ala Trp Ser Gly Tyr Gly Glu Tyr Lys Gly Ile Ala
            850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
            900                 905                 910
Phe Val Gln Ala Arg Lys Gln Leu Lys Glu Gln Gly Gln Ser Leu Gly
            915                 920                 925
Glu Ala His Leu Tyr Phe Gly Cys Arg Ser Pro His Glu Asp Tyr Leu
            930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
            995                 1000                1005
Val Glu Ala Thr Leu Met Lys Ser Tyr Ala Asp Val His Gln Val Ser
    1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
                1045
```

<210> SEQ ID NO 7
<211> LENGTH: 3144
<212> TYPE: DNA
<213> ORGANISM: Bacillus megaterium

<400> SEQUENCE: 7

```
acaattaaag aaatgcctca gccaaaaacg tttggagagc ttaaaaattt accgttatta    60
aacacagata aaccggttca agctttgatg aaaattgcgg atgaattagg agaaatcttt   120
aaattcgagg cgcctggttg tgtaacgcgc tacttatcaa gtcagcgtct aattaaagaa   180
gcatgcgatg aatcacgctt tgataaaaac ttaagtcaag cgcttaaatt tgcacgtgat   240
tttgcaggag acgggttatt tacaagctgg acgcatgaaa taaattggaa aaaagcgcat   300
```

```
aatatcttac ttccaagctt tagtcagcag gcaatgaaag gctatcatgc gatgatggtc     360
gatatcgccg tgcagcttgt tcaaaagtgg gagcgtctaa atgcagatga gcatattgaa     420
gtatcggaag acatgacacg tttaacgctt gatacaattg gtctttgcgg ctttaactat     480
cgctttaaca gcttttaccg agatcagcct catccattta ttataagtat ggtccgtgca     540
ctggatgaag taatgaacaa gctgcagcga gcaaatccag acgacccagc ttatgatgaa     600
aacaagcgcc agtgtcaaga agatatcaag gtgatgaacg acctagtaga taaaattatt     660
gcagatcgca aagcaagggg tgaacaaagc gatgatttat taacgcagat gctaaacgga     720
aaagatccag aaacgggtga gccgcttgat gacgggaaca ttagctatca aattattaca     780
ttcttaattg cggacacga aacaacaagt ggtcttttat catttgcgct gtatttctta     840
gtgaaaaatc cacatgtatt acaaaaagta gcagaagaag cagcacgagt tctagtagat     900
cctgttccaa gctacaaaca agtcaaacag cttaaatatg tcggcatggt cttaaacgaa     960
gcgctgcgct tatggccaac ttttcctgcg ttttccctat atgcaaaaga agatacggtg    1020
cttggaggag aatatccttt agaaaaaggc gacgaagtaa tggttctgat tcctcagctt    1080
caccgtgata aaacaatttg gggagacgat gtggaggagt tccgtccaga gcgttttgaa    1140
aatccaagtg cgattccgca gcatgcgttt aaaccgtttg gaaacggtca gcgtgcgtgt    1200
atcggtcagc agttcgctct tcatgaagca acgctggtac ttggtatgat gctaaaacac    1260
tttgactttg aagatcatac aaactacgag ctcgatatta agaaactttt aacgttaaaa    1320
cctgaaggct ttgtggtaaa agcaaaatcg aaaaaaattc cgcttggcgg tattccttca    1380
cctagcactg aacagtctgc taaaaaagta cgcaaaaagg cagaaaacgc tcataatacg    1440
ccgctgcttg tgctatacgg ttcaaatatg ggaacagctg aaggaacggc gcgtgattta    1500
gcagatattg caatgagcaa aggatttgca ccgcaggtcg caacgcttga ttcacacgcc    1560
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
ggcgttcgct actccgtatt tggatgcggc gataaaaact gggctactac gtatcaaaaa    1740
gtgcctgctt ttatcgatga aacgcttgcc gctaaagggg cagaaaacat cgctgaccgc    1800
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920 actcttttcac ttcaatttgt cgacagcgcc gcggatatgc cgcttgcgaa aatgcacggt    1980
gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgcccct    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
```

```
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa acgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 8
<211> LENGTH: 1048
<212> TYPE: PRT
<213> ORGANISM: Bacillus megaterium

<400> SEQUENCE: 8

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285
```

```
Lys Val Ala Glu Glu Ala Ala Arg Val Leu Val Asp Pro Val Pro Ser
    290                 295                 300
Tyr Lys Gln Val Lys Gln Leu Lys Tyr Val Gly Met Val Leu Asn Glu
305                 310                 315                 320
Ala Leu Arg Leu Trp Pro Thr Phe Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
        435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
        515                 520                 525
Val Leu Ile Val Thr Ala Ser Tyr Asn Gly His Pro Pro Asp Asn Ala
530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
        595                 600                 605
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
            660                 665                 670
Gln Gln Pro Gly Ser Ala Arg Ser Thr Arg His Leu Glu Ile Glu Leu
        675                 680                 685
Pro Lys Glu Ala Ser Tyr Gln Glu Gly Asp His Leu Gly Val Ile Pro
690                 695                 700
```

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Leu Leu Gln Tyr
        740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 9
<211> LENGTH: 3144
<212> TYPE: DNA
<213> ORGANISM: Bacillus megaterium

<400> SEQUENCE: 9
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180

```
gcatgcgatg aatcacgctt tgataaaaac ttaagtcaag cgcttaaatt tgcacgtgat    240
tttgcaggag acgggttatt tacaagctgg acgcatgaaa taaattggaa aaaagcgcat    300
aatatcttac ttccaagctt tagtcagcag gcaatgaaag gctatcatgc gatgatggtc    360
gatatcgccg tgcagcttgt tcaaaagtgg gagcgtctaa atgcagatga gcatattgaa    420
gtatcggaag acatgacacg tttaacgctt gatacaattg gtctttgcgg ctttaactat    480
cgctttaaca gcttttaccg agatcagcct catccattta ttataagtat ggtccgtgca    540
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattaca    780
ttcttaattg cggacacga aacaacaagt ggtctttat catttgcgct gtatttctta    840
gtgaaaaatc cacatgtatt acaaaaagta gcagaagaag cagcacgagt tctagtagat    900
cctgttccaa gctacaaaca agtcaaacag cttaaatatg tcggcatggt cttaaacgaa    960
gcgctgcgct tatggccaac tctccctgcg ttttccctat atgcaaaaga agatacggtg    1020
cttggaggag aatatccttt agaaaaaggc gacgaagtaa tggttctgat tcctcagctt    1080
caccgtgata aaacaatttg gggagacgat gtggaggagt tccgtccaga gcgttttgaa    1140
aatccaagtg cgattccgca gcatgcgttt aaaccgtttg gaaacggtca gcgtgcgtgt    1200
atcggtcagc agttcgctct tcatgaagca acgctggtac ttggtatgat gctaaaacac    1260
tttgactttg aagatcatac aaactacgag ctcgatatta agaaacttt aacgttaaaa    1320 cctgaaggct ttgtggtaaa agcaaaatcg aaaaaaattc cgcttggcgg tattccttca    1380
cctagcactg aacagtctgc taaaaaagta cgcaaaaagg cagaaaacgc tcataatacg    1440
ccgctgcttg tgctatacgg ttcaaatatg gaacagctg aaggaacggc gcgtgattta    1500
gcagatattg caatgagcaa aggatttgca ccgcaggtcg caacgcttga ttcacacgcc    1560
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
ggcgttcgct actccgtatt tggatgcggc gataaaaact gggctactac gtatcaaaaa    1740
gtgcctgctt ttatcgatga aacgcttgcc gctaaagggg cagaaaacat cgctgaccgc    1800
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920
actctttcac ttcaatttgt cgacagcgcc gcggatatgc cgcttgcgaa aatgcacggt    1980
gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtgagagctt    2340 gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgcccctt    2460 ctgccaagca tacgcccgcg ctattactcg atttcttcat cacctcgtgt cgatgaaaaa    2520
```

-continued

```
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa acgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                           3144
```

<210> SEQ ID NO 10
<211> LENGTH: 1048
<212> TYPE: PRT
<213> ORGANISM: Bacillus megaterium

<400> SEQUENCE: 10

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
```

-continued

```
                260                 265                 270
Leu Ser Phe Ala Leu Tyr Phe Leu Val Lys Asn Pro His Val Leu Gln
            275                 280                 285
Lys Val Ala Glu Glu Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Thr Leu Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Ile Trp Gly
            355                 360                 365
Asp Asp Val Glu Glu Phe Arg Pro Glu Arg Phe Glu Asn Pro Ser Ala
            370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
            435                 440                 445
Lys Ser Lys Lys Ile Pro Leu Gly Gly Ile Pro Ser Pro Ser Thr Glu
            450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
            515                 520                 525
Val Leu Ile Val Thr Ala Ser Tyr Asn Gly His Pro Pro Asp Asn Ala
            530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
            595                 600                 605
Phe Glu Gly Thr Tyr Glu Glu Trp Arg Glu His Met Trp Ser Asp Val
            610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
            660                 665                 670
Gln Gln Pro Gly Ser Ala Arg Ser Thr Arg His Leu Glu Ile Glu Leu
            675                 680                 685
```

Pro Lys Glu Ala Ser Tyr Gln Glu Gly Asp His Leu Gly Val Ile Pro
    690             695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
    755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
    995                 1000                1005

Val Glu Ala Thr Leu Met Lys Ser Tyr Ala Asp Val His Gln Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 11
<211> LENGTH: 3144
<212> TYPE: DNA
<213> ORGANISM: Bacillus megaterium

<400> SEQUENCE: 11
acaattaaag aaatgcctca gccaaaaacg tttggagagc ttaaaaattt accgttatta      60

-continued

```
aacacagata aaccggttca agctttgatg aaaattgcgg atgaattagg agaaatcttt    120
aaattcgagg cgcctggttg tgtaacgcgc tacttatcaa gtcagcgtct aattaaagaa    180
gcatgcgatg aatcacgctt tgataaaaac ttaagtcaag cgcttaaatt tgcacgtgat    240
tttgcaggag acgggttatt tacaagctgg acgcatgaaa taaattggaa aaaagcgcat    300
aatatcttac ttccaagctt tagtcagcag gcaatgaaag gctatcatgc gatgatggtc    360
gatatcgccg tgcagcttgt tcaaaagtgg gagcgtctaa atgcagatga gcatattgaa    420
gtatcggaag acatgacacg tttaacgctt gatacaattg gtctttgcgg ctttaactat    480
cgctttaaca gcttttaccg agatcagcct catccattta ttataagtat ggtccgtgca    540
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattaca    780
ttcttaattg cggacacga aacaacaagt ggtcttttat catttgcgct gtatttctta    840
gtgaaaaatc cacatgtatt acaaaaagta gcagaagaag cagcacgagt tctagtagat    900
cctgttccaa gctacaaaca agtcaaacag cttaaatatg tcggcatggt cttaaacgaa    960
gcgctgcgct tatggccaac tatgcctgcg ttttccctat atgcaaaaga agatacggtg   1020
cttggaggag aatatccttt agaaaaaggc gacgaagtaa tggttctgat tcctcagctt   1080
caccgtgata aaacaatttg gggagacgat gtggaggagt tccgtccaga gcgttttgaa   1140
aatccaagtg cgattccgca gcatgcgttt aaaccgtttg gaaacggtca gcgtgcgtgt   1200
atcggtcagc agttcgctct tcatgaagca acgctggtac ttggtatgat gctaaaacac   1260
tttgactttg aagatcatac aaaactacgag ctcgatatta agaaactttt aacgttaaaa   1320
cctgaaggct ttgtggtaaa agcaaaatcg aaaaaaattc cgcttggcgg tattccttca   1380
cctagcactg aacagtctgc taaaaagta cgcaaaaagg cagaaaacgc tcataatacg   1440
ccgctgcttg tgctatacgg ttcaaatatg gaacagctg aaggaacggc gcgtgattta   1500
gcagatattg caatgagcaa aggatttgca ccgcaggtcg caacgcttga ttcacacgcc   1560
ggaaatcttc cgcgcgaagg agctgtatta attgtaacgg cgtcttataa cggtcatccg   1620
cctgataacg caaagcaatt tgtcgactgg ttagaccaag cgtctgctga tgaagtaaaa   1680
ggcgttcgct actccgtatt tggatgcggc gataaaaact gggctactac gtatcaaaaa   1740
gtgcctgctt ttatcgatga aacgcttgcc gctaaagggg cagaaaacat cgctgaccgc   1800
ggtgaagcag atgcaagcga cgactttgaa ggcacatatg aagaatggcg tgaacatatg   1860
tggagtgacg tagcagccta ctttaacctc gacattgaaa acagtgaaga taataaatct   1920
actctttcac ttcaatttgt cgacagcgcc gcggatatgc cgcttgcgaa aatgcacggt   1980
gcgttttcaa cgaacgtcgt agcaagcaaa gaacttcaac agccaggcag tgcacgaagc   2040
acgcgacatc ttgaaattga acttccaaaa gaagcttctt atcaagaagg agatcattta   2100
ggtgttattc ctcgcaacta tgaaggaata gtaaaccgtg taacagcaag gttcggccta   2160
gatgcatcac agcaaatccg tctggaagca gaagaagaaa aattagctca tttgccactc   2220
gctaaaacag tatccgtaga agagcttctg caatacgtgg agcttcaaga tcctgttacg   2280
cgcacgcagc ttcgcgcaat ggctgctaaa acggtctgcc cgccgcataa agtgagagctt   2340 gaagccttgc ttgaaaagca agcctacaaa gaacaagtgc tggcaaaacg tttaacaatg   2400
```

-continued

```
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa acgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 12
<211> LENGTH: 1048
<212> TYPE: PRT
<213> ORGANISM: Bacillus megaterium

<400> SEQUENCE: 12

```
Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240
```

-continued

```
Lys Asp Pro Glu Thr Gly Glu Pro Leu Asp Asp Gly Asn Ile Ser Tyr
            245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Val Ala Glu Glu Ala Ala Arg Val Leu Val Asp Pro Val Pro Ser
            290                 295                 300

Tyr Lys Gln Val Lys Gln Leu Lys Tyr Val Gly Met Val Leu Asn Glu
305                 310                 315                 320

Ala Leu Arg Leu Trp Pro Thr Met Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
            370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
            450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr Asn Val Val Ala Ser Lys Glu Leu
```

-continued

```
           660                 665                 670
Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                1000                1005

Val Glu Ala Thr Leu Met Lys Ser Tyr Ala Asp Val His Gln Val Ser
            1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 13
<211> LENGTH: 3144
<212> TYPE: DNA
<213> ORGANISM: Bacillus megaterium
```

<400> SEQUENCE: 13

```
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgcttaaatt tgcacgtgat     240
tttgcaggag acgggttatt tacaagctgg acgcatgaaa taaattggaa aaaagcgcat     300
aatatcttac ttccaagctt tagtcagcag gcaatgaaag ctatcatgc gatgatggtc      360
gatatcgccg tgcagcttgt tcaaaagtgg gagcgtctaa atgcagatga gcatattgaa     420
gtatcggaag acatgacacg tttaacgctt gatacaattg gtctttgcgg ctttaactat     480
cgctttaaca gcttttaccg agatcagcct catccattta ttataagtat ggtccgtgca     540
ctggatgaag taatgaacaa gctgcagcga gcaaatccag acgacccagc ttatgatgaa     600
aacaagcgcc agtgtcaaga agatatcaag gtgatgaacg acctagtaga taaaattatt     660
gcagatcgca aagcaagggg tgaacaaagc gatgatttat taacgcagat gctaaacgga     720
aaagatccag aaacgggtga gccgcttgat gacgggaaca ttagctatca aattattaca     780
ttcttaattg cgggacacga aacaacaagt ggtcttttat catttgcgct gtatttctta     840
gtgaaaaatc cacatgtatt acaaaaagta gcagaagaag cagcacgagt tctagtagat     900
cctgttccaa gctacaaaca agtcaaacag cttaaatatg tcggcatggt cttaaacgaa     960
gcgctgcgct tatggccaac tgttcctgcg ttttccctat atgcaaaaga agatacggtg    1020
cttggaggag aatatccttt agaaaaaggc gacgaagtaa tggttctgat tcctcagctt    1080
caccgtgata aaacaatttg gggagacgat gtggaggagt tccgtccaga gcgttttgaa    1140
aatccaagtg cgattccgca gcatgcgttt aaaccgtttg gaaacggtca gcgtgcgtgt    1200
atcggtcagc agttcgctct tcatgaagca acgctggtac ttggtatgat gctaaaacac    1260
tttgactttg aagatcatac aaactacgag ctcgatatta agaaactttt aacgttaaaa    1320
cctgaaggct ttgtggtaaa agcaaaatcg aaaaaaattc cgcttggcgg tattccttca    1380
cctagcactg aacagtctgc taaaaaagta cgcaaaaagg cagaaaacgc tcataatacg    1440
ccgctgcttg tgctatacgg ttcaaatatg ggaacagctg aaggaacggc gcgtgattta    1500
gcagatattg caatgagcaa aggatttgca ccgcaggtcg caacgcttga ttcacacgcc    1560
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
ggcgttcgct actccgtatt tggatgcggc gataaaaact gggctactac gtatcaaaaa    1740
gtgcctgctt ttatcgatga aacgcttgcc gctaaagggg cagaaaacat cgctgaccgc    1800
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920
actctttcac ttcaatttgt cgacagcgcc gcggatatgc cgcttgcgaa aatgcacggt    1980
gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
```

-continued

```
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg aacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa acgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                           3144
```

<210> SEQ ID NO 14
<211> LENGTH: 1048
<212> TYPE: PRT
<213> ORGANISM: Bacillus megaterium

<400> SEQUENCE: 14

```
Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220
```

-continued

```
Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
            245                 250                 255

Gln Ile Ile Thr Phe Leu Ile Ala Gly His Glu Thr Thr Ser Gly Leu
        260                 265                 270

Leu Ser Phe Ala Leu Tyr Phe Leu Val Lys Asn Pro His Val Leu Gln
    275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Val Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640
```

```
Thr Leu Ser Leu Gln Phe Val Asp Ser Ala Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val Ser
            1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
            1045
```

<210> SEQ ID NO 15
<211> LENGTH: 3144
<212> TYPE: DNA
<213> ORGANISM: Bacillus megaterium

<400> SEQUENCE: 15

| | | | | | | |
|---|---|---|---|---|---|---|
| acaattaaag | aaatgcctca | gccaaaaacg | tttggagagc | ttaaaaattt | accgttatta | 60 |
| aacacagata | aaccggttca | agctttgatg | aaaattgcgg | atgaattagg | agaaatcttt | 120 |
| aaattcgagg | cgcctggttg | tgtaacgcgc | tacttatcaa | gtcagcgtct | aattaaagaa | 180 |
| gcatgcgatg | aatcacgctt | tgataaaaac | ttaagtcaag | cgcttaaatt | tttccgtgat | 240 |
| tttgcaggag | acgggttatt | tacaagctgg | acgcatgaaa | taaattggaa | aaaagcgcat | 300 |
| aatatcttac | ttccaagctt | tagtcagcag | gcaatgaaag | ctatcatgc | gatgatggtc | 360 |
| gatatcgccg | tgcagcttgt | tcaaaagtgg | gagcgtctaa | atgcagatga | gcatattgaa | 420 |
| gtatcggaag | acatgacacg | tttaacgctt | gatacaattg | gtctttgcgg | ctttaactat | 480 |
| cgctttaaca | gcttttaccg | agatcagcct | catccattta | ttataagtat | ggtccgtgca | 540 |
| ctggatgaag | taatgaacaa | gctgcagcga | gcaaatccag | acgacccagc | ttatgatgaa | 600 |
| aacaagcgcc | agtgtcaaga | agatatcaag | gtgatgaacg | acctagtaga | taaaattatt | 660 |
| gcagatcgca | aagcaagggg | tgaacaaagc | gatgattat | taacgcagat | gctaaacgga | 720 |
| aaagatccag | aaacgggtga | gccgcttgat | gacgggaaca | ttagctatca | aattattaca | 780 |
| ttcttaattg | cgggacacga | aacaacaagt | ggtctttat | catttgcgct | gtatttctta | 840 |
| gtgaaaaatc | cacatgtatt | acaaaaagta | gcagaagaag | cagcacgagt | tctagtagat | 900 |
| cctgttccaa | gctacaaaca | agtcaaacag | cttaaatatg | tcggcatggt | cttaaacgaa | 960 |
| gcgctgcgct | tatggccaac | tgctcctgcg | ttttccctat | atgcaaaaga | agatacggtg | 1020 |
| cttggaggag | aatatccttt | agaaaaaggc | gacgaagtaa | tggttctgat | tcctcagctt | 1080 |
| caccgtgata | aaacaatttg | gggagacgat | gtggaggagt | tccgtccaga | gcgttttgaa | 1140 |
| aatccaagtg | cgattccgca | gcatgcgttt | aaaccgtttg | gaaacggtca | gcgtgcgtgt | 1200 |
| atcggtcagc | agttcgctct | tcatgaagca | acgctggtac | ttggtatgat | gctaaaacac | 1260 |
| tttgactttg | aagatcatac | aaactacgag | ctcgatatta | agaaactttt | aacgttaaaa | 1320 |
| cctgaaggct | ttgtggtaaa | agcaaaatcg | aaaaaaattc | cgcttggcgg | tattccttca | 1380 |
| cctagcactg | aacagtctgc | taaaaaagta | cgcaaaaagg | cagaaaacgc | tcataatacg | 1440 |
| ccgctgcttg | tgctatacgg | ttcaaatatg | gaacagctg | aaggaacggc | gcgtgattta | 1500 |
| gcagatattg | caatgagcaa | aggatttgca | ccgcaggtcg | caacgcttga | ttcacacgcc | 1560 |
| ggaaatcttc | cgcgcgaagg | agctgtatta | attgtaacgg | cgtcttataa | cggtcatccg | 1620 |
| cctgataacg | caaagcaatt | tgtcgactgg | ttagaccaag | cgtctgctga | tgaagtaaaa | 1680 |
| ggcgttcgct | actccgtatt | tggatgcggc | gataaaaact | gggctactac | gtatcaaaaa | 1740 |
| gtgcctgctt | ttatcgatga | aacgcttgcc | gctaaagggg | cagaaaacat | cgctgaccgc | 1800 |
| ggtgaagcag | atgcaagcga | cgactttgaa | ggcacatatg | aagaatggcg | tgaacatatg | 1860 |
| tggagtgacg | tagcagccta | ctttaacctc | gacattgaaa | acagtgaaga | taataaatct | 1920 |
| actctttcac | ttcaatttgt | cgacagcgcc | gcggatatgc | cgcttgcgaa | aatgcacggt | 1980 |
| gcgttttcaa | cgaacgtcgt | agcaagcaaa | gaacttcaac | agccaggcag | tgcacgaagc | 2040 |
| acgcgacatc | ttgaaattga | acttccaaaa | gaagcttctt | atcaagaagg | agatcattta | 2100 |
| ggtgttattc | ctcgcaacta | tgaaggaata | gtaaaccgtg | taacagcaag | gttcggccta | 2160 |

```
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg aacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                           3144
```

<210> SEQ ID NO 16
<211> LENGTH: 1048
<212> TYPE: PRT
<213> ORGANISM: Bacillus megaterium

<400> SEQUENCE: 16

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Phe Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
```

```
                195                 200                 205
Ile Lys Val Met Asn Asp Leu Val Asp Lys Ile Ile Ala Asp Arg Lys
    210                 215                 220
Ala Arg Gly Glu Gln Ser Asp Asp Leu Leu Thr Gln Met Leu Asn Gly
225                 230                 235                 240
Lys Asp Pro Glu Thr Gly Glu Pro Leu Asp Asp Gly Asn Ile Ser Tyr
                245                 250                 255
Gln Ile Ile Thr Phe Leu Ile Ala Gly His Glu Thr Thr Ser Gly Leu
                260                 265                 270
Leu Ser Phe Ala Leu Tyr Phe Leu Val Lys Asn Pro His Val Leu Gln
    275                 280                 285
Lys Val Ala Glu Glu Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Ile Trp Gly
            355                 360                 365
Asp Asp Val Glu Glu Phe Arg Pro Glu Arg Phe Glu Asn Pro Ser Ala
    370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
                420                 425                 430
Ile Lys Glu Thr Leu Thr Leu Lys Pro Glu Gly Phe Val Val Lys Ala
            435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
            515                 520                 525
Val Leu Ile Val Thr Ala Ser Tyr Asn Gly His Pro Pro Asp Asn Ala
    530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
            595                 600                 605
Phe Glu Gly Thr Tyr Glu Glu Trp Arg Glu His Met Trp Ser Asp Val
    610                 615                 620
```

-continued

```
Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Asp Met Pro Leu Ala
            645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val Ser
            1010                1015                1020

Glu Ala Asp Ala Arg Leu Trp Leu Gln Gln Leu Glu Glu Lys Gly Arg
1025                1030                1035                1040
```

Tyr Ala Lys Asp Val Trp Ala Gly
    1045

<210> SEQ ID NO 17
<211> LENGTH: 3144
<212> TYPE: DNA
<213> ORGANISM: Bacillus megaterium

<400> SEQUENCE: 17

| | | | | | |
|---|---|---|---|---|---|
| acaattaaag | aaatgcctca | gccaaaaacg | tttggagagc | ttaaaaattt | accgttatta | 60 |
| aacacagata | aaccggttca | agctttgatg | aaaattgcgg | atgaattagg | agaaatcttt | 120 |
| aaattcgagg | cgcctggttg | tgtaacgcgc | tacttatcaa | gtcagcgtct | aattaaagaa | 180 |
| gcatgcgatg | aatcacgctt | tgataaaaac | ttaagtcaag | cgcttaaatt | ttcccgtgat | 240 |
| tttgcaggag | acgggttatt | tacaagctgg | acgcatgaaa | taaattggaa | aaaagcgcat | 300 |
| aatatcttac | ttccaagctt | tagtcagcag | gcaatgaaag | ctatcatgc | gatgatggtc | 360 |
| gatatcgccg | tgcagcttgt | tcaaaagtgg | gagcgtctaa | atgcagatga | gcatattgaa | 420 |
| gtatcggaag | acatgacacg | tttaacgctt | gatacaattg | gtctttgcgg | ctttaactat | 480 |
| cgctttaaca | gcttttaccg | agatcagcct | catccattta | ttataagtat | ggtccgtgca | 540 |
| ctggatgaag | taatgaacaa | gctgcagcga | gcaaatccag | acgacccagc | ttatgatgaa | 600 |
| aacaagcgcc | agtgtcaaga | agatatcaag | gtgatgaacg | acctagtaga | taaaattatt | 660 |
| gcagatcgca | aagcaagggg | tgaacaaagc | gatgatttat | taacgcagat | gctaaacgga | 720 |
| aaagatccag | aaacgggtga | gccgcttgat | gacgggaaca | ttagctatca | aattattaca | 780 |
| ttcttaattg | cgggacacga | aacaacaagt | ggtctttat | catttgcgct | gtatttctta | 840 |
| gtgaaaaatc | cacatgtatt | acaaaaagta | gcagaagaag | cagcacgagt | tctagtagat | 900 |
| cctgttccaa | gctacaaaca | agtcaaacag | cttaaatatg | tcggcatggt | cttaaacgaa | 960 |
| gcgctgcgct | tatggccaac | tgctcctgcg | ttttccctat | atgcaaaaga | agatacggtg | 1020 |
| cttggaggag | aatatccttt | agaaaaaggc | gacgaagtaa | tggttctgat | tcctcagctt | 1080 |
| caccgtgata | aaacaatttg | gggagacgat | gtggaggagt | tccgtccaga | gcgttttgaa | 1140 |
| aatccaagtg | cgattccgca | gcatgcgttt | aaaccgtttg | gaaacggtca | gcgtgcgtgt | 1200 |
| atcggtcagc | agttcgctct | tcatgaagca | acgctggtac | ttggtatgat | gctaaaacac | 1260 |
| tttgactttg | aagatcatac | aaaactacgag | ctcgatatta | agaaactttt | aacgttaaaa | 1320 |
| cctgaaggct | ttgtggtaaa | agcaaaatcg | aaaaaaattc | cgcttggcgg | tattccttca | 1380 |
| cctagcactg | aacagtctgc | taaaaaagta | cgcaaaaagg | cagaaaacgc | tcataatacg | 1440 |
| ccgctgcttg | tgctatacgg | ttcaaatatg | ggaacagctg | aaggaacggc | gcgtgattta | 1500 |
| gcagatattg | caatgagcaa | aggatttgca | ccgcaggtcg | caacgcttga | ttcacacgcc | 1560 |
| ggaaatcttc | cgcgcgaagg | agctgtatta | attgtaacgg | cgtcttataa | cggtcatccg | 1620 |
| cctgataacg | caaagcaatt | tgtcgactgg | ttagaccaag | cgtctgctga | tgaagtaaaa | 1680 |
| ggcgttcgct | actccgtatt | tggatgcggc | gataaaaact | gggctactac | gtatcaaaaa | 1740 |
| gtgcctgctt | ttatcgatga | aacgcttgcc | gctaaagggg | cagaaaacat | cgctgaccgc | 1800 |
| ggtgaagcag | atgcaagcga | cgactttgaa | ggcacatatg | aagaatggcg | tgaacatatg | 1860 |
| tggagtgacg | tagcagccta | ctttaaccctc | gacattgaaa | acagtgaaga | taataaatct | 1920 |
| actcttttcac | ttcaatttgt | cgacagcgcc | gcggatatgc | cgcttgcgaa | aatgcacggt | 1980 |
| gcgttttcaa | cgaacgtcgt | agcaagcaaa | gaacttcaac | agccaggcag | tgcacgaagc | 2040 |

-continued

```
acgcgacatc ttgaaattga acttccaaaa gaagcttctt atcaagaagg agatcattta      2100
ggtgttattc ctcgcaacta tgaaggaata gtaaaccgtg taacagcaag gttcggccta      2160
gatgcatcac agcaaatccg tctggaagca gaagaagaaa aattagctca tttgccactc      2220
gctaaaacag tatccgtaga agagcttctg caatacgtgg agcttcaaga tcctgttacg      2280
cgcacgcagc ttcgcgcaat ggctgctaaa acggtctgcc cgccgcataa agtagagctt      2340
gaagccttgc ttgaaaagca agcctacaaa gaacaagtgc tggcaaaacg tttaacaatg      2400
cttgaactgc ttgaaaaata cccggcgtgt gaaatgaaat tcagcgaatt tatcgccctt      2460
ctgccaagca tacgcccgcg ctattactcg atttcttcat cacctcgtgt cgatgaaaaa      2520
caagcaagca tcacggtcag cgttgtctca ggagaagcgt ggagcggata tggagaatat      2580
aaaggaattg cgtcgaacta tcttgccgag ctgcaagaag gagatacgat tacgtgcttt      2640
atttccacac cgcagtcaga atttacgctg ccaaaagacc ctgaaacgcc gcttatcatg      2700 gtcgaccgg gaacaggcgt cgcgccgttt agaggctttg tgcaggcgcg caaacagcta      2760
aaagaacaag gacagtcact tggagaagca catttatact tcggctgccg ttcacctcat      2820
gaagactatc tgtatcaaga agagcttgaa acgcccaaa gcgaaggcat cattacgctt      2880
cataccgctt tttctcgcat gccaaatcag ccgaaaacat acgttcagca cgtaatggaa      2940
caagacggca agaaattgat tgaacttctt gatcaaggag cgcacttcta tatttgcgga      3000
gacggaagcc aaatggcacc tgccgttgaa gcaacgctta tgaaaagcta tgctgacgtt      3060
caccaagtga gtgaagcaga cgctcgctta tggctgcagc agctagaaga aaaaggccga      3120
tacgcaaaag acgtgtgggc tggg                                             3144
```

<210> SEQ ID NO 18
<211> LENGTH: 1048
<212> TYPE: PRT
<213> ORGANISM: Bacillus megaterium

<400> SEQUENCE: 18

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
                 20                  25                  30

Ala Asp Glu Leu Gly Glu Ile Phe Lys Phe Glu Ala Pro Gly Cys Val
             35                  40                  45

Thr Arg Tyr Leu Ser Ser Gln Arg Leu Ile Lys Glu Ala Cys Asp Glu
         50                  55                  60

Ser Arg Phe Asp Lys Asn Leu Ser Gln Ala Leu Lys Phe Ser Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175
```

-continued

```
Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
            195                 200             205

Ile Lys Val Met Asn Asp Leu Val Asp Lys Ile Ala Asp Arg Lys
    210                 215                 220

Ala Arg Gly Glu Gln Ser Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
```

-continued

```
                595                 600                 605
Phe Glu Gly Thr Tyr Glu Trp Arg Glu His Met Trp Ser Asp Val
    610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
                675                 680                 685
Pro Lys Glu Ala Ser Tyr Gln Glu Gly Asp His Leu Gly Val Ile Pro
    690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Glu Leu Leu Gln Tyr
                740                 745                 750
Val Glu Leu Gln Asp Pro Val Thr Arg Thr Gln Leu Arg Ala Met Ala
                755                 760                 765
Ala Lys Thr Val Cys Pro Pro His Lys Val Glu Leu Glu Ala Leu Leu
    770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
                820                 825                 830
Ser Ser Pro Arg Val Asp Glu Lys Gln Ala Ser Ile Thr Val Ser Val
    835                 840                 845
Val Ser Gly Glu Ala Trp Ser Gly Tyr Gly Glu Tyr Lys Gly Ile Ala
    850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
                900                 905                 910
Phe Val Gln Ala Arg Lys Gln Leu Lys Glu Gln Gly Gln Ser Leu Gly
                915                 920                 925
Glu Ala His Leu Tyr Phe Gly Cys Arg Ser Pro His Glu Asp Tyr Leu
    930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
                980                 985                 990
Gly Ala His Phe Tyr Ile Cys Gly Asp Gly Ser Gln Met Ala Pro Ala
                995                 1000                1005
Val Glu Ala Thr Leu Met Lys Ser Tyr Ala Asp Val His Gln Val Ser
    1010                1015                1020
```

Glu Ala Asp Ala Arg Leu Trp Leu Gln Gln Leu Glu Glu Lys Gly Arg
1025                1030                1035                1040

Tyr Ala Lys Asp Val Trp Ala Gly
            1045

<210> SEQ ID NO 19
<211> LENGTH: 3144
<212> TYPE: DNA
<213> ORGANISM: Bacillus megaterium

<400> SEQUENCE: 19

| | | | | | |
|---|---|---|---|---|---|
| acaattaaag | aaatgcctca | gccaaaaacg | tttggagagc | ttaaaaattt | accgttatta | 60 |
| aacacagata | aaccggttca | agctttgatg | aaaattgcgg | atgaattagg | agaaatcttt | 120 |
| aaattcgagg | cgcctggttg | tgtaacgcgc | tacttatcaa | gtcagcgtct | aattaaagaa | 180 |
| gcatgcgatg | aatcacgctt | tgataaaaac | ttaagtcaag | cgcttaaatt | tacacgtgat | 240 |
| tttgcaggag | acgggttatt | tacaagctgg | acgcatgaaa | taaattggaa | aaaagcgcat | 300 |
| aatatcttac | ttccaagctt | tagtcagcag | gcaatgaaag | ctatcatgc | gatgatggtc | 360 |
| gatatcgccg | tgcagcttgt | tcaaaagtgg | gagcgtctaa | atgcagatga | gcatattgaa | 420 |
| gtatcggaag | acatgacacg | tttaacgctt | gatacaattg | gtctttgcgg | ctttaactat | 480 |
| cgctttaaca | gcttttaccg | agatcagcct | catccattta | ttataagtat | ggtccgtgca | 540 |
| ctggatgaag | taatgaacaa | gctgcagcga | gcaaatccag | acgacccagc | ttatgatgaa | 600 |
| aacaagcgcc | agtgtcaaga | agatatcaag | gtgatgaacg | acctagtaga | taaaattatt | 660 |
| gcagatcgca | aagcaagggg | tgaacaaagc | gatgatttat | taacgcagat | gctaaacgga | 720 |
| aaagatccag | aaacgggtga | gccgcttgat | gacgggaaca | ttagctatca | aattattaca | 780 |
| ttcttaattg | cgggacacga | aacaacaagt | ggtctttat | catttgcgct | gtatttctta | 840 |
| gtgaaaaatc | cacatgtatt | acaaaaagta | gcagaagaag | cagcacgagt | tctagtagat | 900 |
| cctgttccaa | gctacaaaca | agtcaaacag | cttaaatatg | tcggcatggt | cttaaacgaa | 960 |
| gcgctgcgct | tatggccaac | tgctcctgcg | ttttccctat | atgcaaaaga | agatacggtg | 1020 |
| cttggaggag | aatatccttt | agaaaaaggc | gacgaagtaa | tggttctgat | tcctcagctt | 1080 |
| caccgtgata | aacaatttg | gggagacgat | gtggaggagt | tccgtccaga | gcgttttgaa | 1140 |
| aatccaagtg | cgattccgca | gcatgcgttt | aaaccgtttg | gaacggtca | gcgtgcgtgt | 1200 |
| atcggtcagc | agttcgctct | tcatgaagca | acgctggtac | ttggtatgat | gctaaaacac | 1260 |
| tttgactttg | aagatcatac | aaactacgag | ctcgatatta | agaaactttt | aacgttaaaa | 1320 |
| cctgaaggct | tgtgtggtaaa | agcaaaatcg | aaaaaaattc | cgcttggcgg | tattccttca | 1380 |
| cctagcactg | aacagtctgc | taaaaaagta | cgcaaaaagg | cagaaaacgc | tcataatacg | 1440 |
| ccgctgcttg | tgctatacgg | ttcaaatatg | ggaacagctg | aaggaacggc | gcgtgattta | 1500 |
| gcagatattg | caatgagcaa | aggatttgca | ccgcaggtcg | caacgcttga | ttcacacgcc | 1560 |
| ggaaatcttc | cgcgcgaagg | agctgtatta | attgtaacgg | cgtctttataa | cggtcatccg | 1620 |
| cctgataacg | caaagcaatt | tgtcgactgg | ttagaccaag | cgtctgctga | tgaagtaaaa | 1680 |
| ggcgttcgct | actccgtatt | tggatgcggc | gataaaaact | gggctactac | gtatcaaaaa | 1740 |
| gtgcctgctt | ttatcgatga | aacgcttgcc | gctaaggggg | cagaaaacat | cgctgaccgc | 1800 |
| ggtgaagcag | atgcaagcga | cgactttgaa | ggcacatatg | aagaatggcg | tgaacatatg | 1860 |
| tggagtgacg | tagcagccta | ctttaacctc | gacattgaaa | acagtgaaga | taataaatct | 1920 |

```
actctttcac ttcaatttgt cgacagcgcc gcggatatgc cgcttgcgaa aatgcacggt    1980
gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa acgcccaaa gcgaaggcat cattacgctt    2880
cataccgctt tttctcgcat gccaaatcag ccgaaaacat acgttcagca cgtaatggaa    2940
caagacggca gaaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 20
<211> LENGTH: 1048
<212> TYPE: PRT
<213> ORGANISM: Bacillus megaterium

<400> SEQUENCE: 20

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
                 20                  25                  30

Ala Asp Glu Leu Gly Glu Ile Phe Lys Phe Glu Ala Pro Gly Cys Val
             35                  40                  45

Thr Arg Tyr Leu Ser Ser Gln Arg Leu Ile Lys Glu Ala Cys Asp Glu
         50                  55                  60

Ser Arg Phe Asp Lys Asn Leu Ser Gln Ala Leu Lys Phe Thr Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160
```

```
Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Pro Ala Tyr Asp Glu Asn Lys Arg Gln Cys Gln Glu Asp
        195                 200                 205

Ile Lys Val Met Asn Asp Leu Val Asp Lys Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575
```

-continued

```
Thr Tyr Gln Lys Val Pro Ala Phe Ile Asp Glu Thr Leu Ala Ala Lys
        580                 585                 590
Gly Ala Glu Asn Ile Ala Asp Arg Gly Glu Ala Asp Ala Ser Asp Asp
        595                 600                 605
Phe Glu Gly Thr Tyr Glu Glu Trp Arg Glu His Met Trp Ser Asp Val
610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
                675                 680                 685
Pro Lys Glu Ala Ser Tyr Gln Glu Gly Asp His Leu Gly Val Ile Pro
        690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Glu Leu Leu Gln Tyr
                740                 745                 750
Val Glu Leu Gln Asp Pro Val Thr Arg Thr Gln Leu Arg Ala Met Ala
                755                 760                 765
Ala Lys Thr Val Cys Pro Pro His Lys Val Glu Leu Glu Ala Leu Leu
                770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
                820                 825                 830
Ser Ser Pro Arg Val Asp Glu Lys Gln Ala Ser Ile Thr Val Ser Val
                835                 840                 845
Val Ser Gly Glu Ala Trp Ser Gly Tyr Gly Glu Tyr Lys Gly Ile Ala
        850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
                900                 905                 910
Phe Val Gln Ala Arg Lys Gln Leu Lys Glu Gln Gly Gln Ser Leu Gly
                915                 920                 925
Glu Ala His Leu Tyr Phe Gly Cys Arg Ser Pro His Glu Asp Tyr Leu
        930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
                980                 985                 990
Gly Ala His Phe Tyr Ile Cys Gly Asp Gly Ser Gln Met Ala Pro Ala
```

```
                995            1000           1005
          Val Glu Ala Thr Leu Met Lys Ser Tyr Ala Asp Val His Gln Val Ser
             1010           1015           1020
          Glu Ala Asp Ala Arg Leu Trp Leu Gln Gln Leu Glu Glu Lys Gly Arg
          1025           1030           1035           1040
          Tyr Ala Lys Asp Val Trp Ala Gly
                     1045

<210> SEQ ID NO 21
<211> LENGTH: 3144
<212> TYPE: DNA
<213> ORGANISM: Bacillus megaterium

<400> SEQUENCE: 21
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgcttaaatt tgcacgtgat     240
ttttgcggag acgggttatt tacaagctgg acgcatgaaa taaattggaa aaaagcgcat     300
aatatcttac ttccaagctt tagtcagcag gcaatgaaag ctatcatgc gatgatggtc      360 gatatcgccg tgcagcttgt tcaaaagtgg gagcgtctaa atgcagatga gcatattgaa     420
gtatcggaag acatgacacg tttaacgctt gatacaattg gtctttgcgg ctttaactat     480
cgctttaaca gcttttaccg agatcagcct catccattta ttataagtat ggtccgtgca     540
ctggatgaag taatgaacaa gctgcagcga gcaaatccag acgacccagc ttatgatgaa     600
aacaagcgcc agtgtcaaga agatatcaag gtgatgaacg acctagtaga taaaattatt     660
gcagatcgca agcaagggg tgaacaaagc gatgatttat taacgcagat gctaaacgga     720
aaagatccag aaacgggtga ccgcttgat gacgggaaca ttagctatca aattattaca     780
ttcttaattg cgggacacga aacaacaagt ggtctttat catttgcgct gtatttctta     840
gtgaaaaatc cacatgtatt acaaaaagta gcagaagaag cagcacgagt tctagtagat     900
cctgttccaa gctacaaaca agtcaaacag cttaaatatg tcggcatggt cttaaacgaa     960
gcgctgcgct tatggccaac tgctcctgcg tttcctat atgcaaaaga agatacggtg    1020
cttggaggag aatatccttt agaaaaaggc gacgaagtaa tggttctgat tcctcagctt    1080
caccgtgata aaacaatttg gggagacgat gtggaggagt tccgtccaga gcgttttgaa    1140
aatccaagtg cgattccgca gcatgcgttt aaaccgtttg gaacggtca gcgtgcgtgt    1200 atcggtcagc agttcgctct tcatgaagca acgctggtac ttggtatgat gctaaaacac    1260
tttgactttg aagatcatac aaactacgag ctcgatatta agaaactttt aacgttaaaa    1320
cctgaaggct ttgtggtaaa agcaaaatcg aaaaaaattc cgcttggcgg tattccttca    1380
cctagcactg aacagtctgc taaaaaagta cgcaaaaagg cagaaaacgc tcataatacg    1440
ccgctgcttg tgctatacgg ttcaaatatg gaacagctg aaggaacggc gcgtgattta    1500
gcagatattg caatgagcaa aggatttgca ccgcaggtcg caacgcttga ttcacacgcc    1560
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
ggcgttcgct actccgtatt tggatgcggc gataaaaact gggctactac gtatcaaaaa    1740
gtgcctgctt ttatcgatga aacgcttgcc gctaaggggg cagaaaacat cgctgaccgc    1800
```

```
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920
actctttcac ttcaatttgt cgacagcgcc gcggatatgc cgcttgcgaa aatgcacggt    1980
gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                            3144
```

<210> SEQ ID NO 22
<211> LENGTH: 1048
<212> TYPE: PRT
<213> ORGANISM: Bacillus megaterium

<400> SEQUENCE: 22

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
              20                  25                  30

Ala Asp Glu Leu Gly Glu Ile Phe Lys Phe Glu Ala Pro Gly Cys Val
          35                  40                  45

Thr Arg Tyr Leu Ser Ser Gln Arg Leu Ile Lys Glu Ala Cys Asp Glu
      50                  55                  60

Ser Arg Phe Asp Lys Asn Leu Ser Gln Ala Leu Lys Phe Ala Arg Asp
 65                  70                  75                  80

Phe Cys Gly Asp Gly Leu Phe Thr Ser Trp Thr His Glu Ile Asn Trp
                  85                  90                  95

Lys Lys Ala His Asn Ile Leu Leu Pro Ser Phe Ser Gln Gln Ala Met
             100                 105                 110

Lys Gly Tyr His Ala Met Met Val Asp Ile Ala Val Gln Leu Val Gln
         115                 120                 125

Lys Trp Glu Arg Leu Asn Ala Asp Glu His Ile Glu Val Ser Glu Asp
```

-continued

```
                130                 135                 140
Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
                530                 535                 540

Lys Gln Phe Val Asp Trp Leu Asp Gln Ala Ser Ala Asp Glu Val Lys
545                 550                 555                 560
```

-continued

```
Gly Val Arg Tyr Ser Val Phe Gly Cys Gly Asp Lys Asn Trp Ala Thr
            565                 570                 575
Thr Tyr Gln Lys Val Pro Ala Phe Ile Asp Glu Thr Leu Ala Ala Lys
        580                 585                 590
Gly Ala Glu Asn Ile Ala Asp Arg Gly Glu Ala Asp Ala Ser Asp Asp
        595                 600                 605
Phe Glu Gly Thr Tyr Glu Glu Trp Arg Glu His Met Trp Ser Asp Val
    610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
            645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
            675                 680                 685
Pro Lys Glu Ala Ser Tyr Gln Glu Gly Asp His Leu Gly Val Ile Pro
        690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
            725                 730                 735
His Leu Pro Leu Ala Lys Thr Val Ser Val Glu Glu Leu Leu Gln Tyr
            740                 745                 750
Val Glu Leu Gln Asp Pro Val Thr Arg Thr Gln Leu Arg Ala Met Ala
        755                 760                 765
Ala Lys Thr Val Cys Pro Pro His Lys Val Glu Leu Glu Ala Leu Leu
        770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
            805                 810                 815
Phe Ile Ala Leu Leu Pro Ser Ile Arg Pro Arg Tyr Tyr Ser Ile Ser
            820                 825                 830
Ser Ser Pro Arg Val Asp Glu Lys Gln Ala Ser Ile Thr Val Ser Val
        835                 840                 845
Val Ser Gly Glu Ala Trp Ser Gly Tyr Gly Glu Tyr Lys Gly Ile Ala
        850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
                900                 905                 910
Phe Val Gln Ala Arg Lys Gln Leu Lys Glu Gln Gly Gln Ser Leu Gly
            915                 920                 925
Glu Ala His Leu Tyr Phe Gly Cys Arg Ser Pro His Glu Asp Tyr Leu
        930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
```

```
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
            995                 1000                1005
Val Glu Ala Thr Leu Met Lys Ser Tyr Ala Asp Val His Gln Val Ser
        1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
            1045

<210> SEQ ID NO 23
<211> LENGTH: 3144
<212> TYPE: DNA
<213> ORGANISM: Bacillus megaterium

<400> SEQUENCE: 23
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgcttaaatt tgcacgtgat     240
tttttcggag acgggttatt tacaagctgg acgcatgaaa taaattggaa aaaagcgcat     300
aatatcttac ttccaagctt tagtcagcag gcaatgaaag ctatcatgc gatgatggtc     360 gatatcgccg tgcagcttgt tcaaaagtgg agcgtctaa atgcagatga gcatattgaa     420
gtatcggaag acatgacacg tttaacgctt gatacaattg gtctttgcgg ctttaactat     480
cgctttaaca gcttttaccg agatcagcct catccattta ttataagtat ggtccgtgca     540
ctggatgaag taatgaacaa gctgcagcga gcaaatccag acgacccagc ttatgatgaa     600
aacaagcgcc agtgtcaaga agatatcaag gtgatgaacg acctagtaga taaaattatt     660
gcagatcgca agcaagggg tgaacaaagc gatgattat taacgcagat gctaaacgga     720
aaagatccag aaacgggtga gccgcttgat gacgggaaca ttagctatca aattattaca     780
ttcttaattg cgggacacga aacaacaagt ggtctttat catttgcgct gtatttctta     840
gtgaaaaatc cacatgtatt acaaaaagta gcagaagaag cagcacgagt tctagtagat     900
cctgttccaa gctacaaaca agtcaaacag cttaaatatg tcggcatggt cttaaacgaa     960
gcgctgcgct tatggccaac tgctcctgcg ttttccctat atgcaaaaga agatacggtg    1020
cttggaggag aatatccttt agaaaaaggc gacgaagtaa tggttctgat tcctcagctt    1080
caccgtgata aaacaatttg gggagacgat gtggaggagt tccgtccaga gcgttttgaa    1140
aatccaagtg cgattccgca gcatgcgttt aaaccgtttg gaacggtca gcgtgcgtgt    1200 atcggtcagc agttcgctct tcatgaagca acgctggtac ttggtatgat gctaaaacac    1260
tttgactttg aagatcatac aaactacgag ctcgatatta agaaacttt aacgttaaaa    1320 cctgaaggct ttgtggtaaa agcaaaatcg aaaaaaattc cgcttggcgg tattccttca    1380
cctagcactg aacagtctgc taaaaagta cgcaaaaagg cagaaaacgc tcataatacg    1440
ccgctgcttg tgctatacgg ttcaaatatg ggaacagctg aaggaacggc gcgtgattta    1500
gcagatattg caatgagcaa aggatttgca ccgcaggtcg caacgcttga ttcacacgcc    1560
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
```

```
ggcgttcgct actccgtatt tggatgcggc gataaaaact gggctactac gtatcaaaaa    1740
gtgcctgctt ttatcgatga aacgcttgcc gctaaagggg cagaaaacat cgctgaccgc    1800
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920
actctttcac ttcaatttgt cgacagcgcc gcggatatgc cgcttgcgaa aatgcacggt    1980
gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 24
<211> LENGTH: 1048
<212> TYPE: PRT
<213> ORGANISM: Bacillus megaterium

<400> SEQUENCE: 24

Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Phe Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

-continued

```
Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
                180                 185                 190

Pro Asp Asp Pro Ala Tyr Asp Glu Asn Lys Arg Gln Cys Gln Glu Asp
                195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
                290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
```

-continued

```
            530                 535                 540
Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
                755                 760                 765

Ala Lys Thr Val Cys Pro Pro His Lys Val Glu Leu Glu Ala Leu Leu
                770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
                835                 840                 845

Val Ser Gly Glu Ala Trp Ser Gly Tyr Gly Glu Tyr Lys Gly Ile Ala
                850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
                930                 935                 940

Tyr Gln Glu Glu Leu Glu Asn Ala Gln Ser Glu Gly Ile Ile Thr Leu
945                 950                 955                 960
```

```
        His Thr Ala Phe Ser Arg Met Pro Asn Gln Pro Lys Thr Tyr Val Gln
                    965                 970                 975

His Val Met Glu Gln Asp Gly Lys Lys Leu Ile Glu Leu Leu Asp Gln
                    980                 985                 990

Gly Ala His Phe Tyr Ile Cys Gly Asp Gly Ser Gln Met Ala Pro Ala
                    995                1000                1005

Val Glu Ala Thr Leu Met Lys Ser Tyr Ala Asp Val His Gln Val Ser
                1010                1015                1020

Glu Ala Asp Ala Arg Leu Trp Leu Gln Gln Leu Glu Glu Lys Gly Arg
        1025                1030                1035                1040

Tyr Ala Lys Asp Val Trp Ala Gly
                    1045

<210> SEQ ID NO 25
<211> LENGTH: 3144
<212> TYPE: DNA
<213> ORGANISM: Bacillus megaterium

<400> SEQUENCE: 25
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgcttaaatt tgcacgtgat     240
tttgggggag acgggttatt tacaagctgg acgcatgaaa taaattggaa aaaagcgcat     300
aatatcttac ttccaagctt tagtcagcag gcaatgaaag ctatcatgc gatgatggtc     360 gatatcgccg tgcagcttgt tcaaaagtgg gagcgtctaa atgcagatga gcatattgaa     420
gtatcggaag acatgacacg tttaacgctt gatacaattg gtctttgcgg ctttaactat     480
cgctttaaca gcttttaccg agatcagcct catccattta ttataagtat ggtccgtgca     540
ctggatgaag taatgaacaa gctgcagcga gcaaatccag acgacccagc ttatgatgaa     600
aacaagcgcc agtgtcaaga agatatcaag gtgatgaacg acctagtaga taaaattatt     660
gcagatcgca aagcaagggg tgaacaaagc gatgatttat taacgcagat gctaaacgga     720
aaagatccag aaacgggtga gccgcttgat gacgggaaca ttagctatca aattattaca     780
ttcttaattg cgggacacga aacaacaagt ggtctttat catttgcgct gtatttctta     840
gtgaaaaatc cacatgtatt acaaaaagta gcagaagaag cagcacgagt tctagtagat     900
cctgttccaa gctacaaaca agtcaaacag cttaaatatg tcggcatggt cttaaacgaa     960
gcgctgcgct tatggccaac tgctcctgcg ttttccctat atgcaaaaga agatacggtg    1020
cttggaggag aatatccttt agaaaaaggc gacgaagtaa tggttctgat tcctcagctt    1080
caccgtgata aaacaatttg gggagacgat gtggaggagt ccgtccaga gcgttttgaa    1140 aatccaagtg cgattccgca gcatgcgttt aaaccgtttg gaaacggtca gcgtgcgtgt    1200
atcggtcagc agttcgctct tcatgaagca acgctggtac ttggtatgat gctaaaacac    1260
tttgactttg aagatcatac aaactacgag ctcgatatta agaaacttt aacgttaaaa    1320 cctgaaggct ttgtggtaaa agcaaaatcg aaaaaaattc cgcttggcgg tattccttca    1380
cctagcactg aacagtctgc taaaaaagta cgcaaaaagg cagaaaacgc tcataatacg    1440
ccgctgcttg tgctatacgg ttcaaatatg ggaacagctg aaggaacggc gcgtgattta    1500
gcagatattg caatgagcaa aggatttgca ccgcaggtcg caacgcttga ttcacacgcc    1560
```

```
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
ggcgttcgct actccgtatt tggatgcggc gataaaaact gggctactac gtatcaaaaa    1740
gtgcctgctt ttatcgatga aacgcttgcc gctaaggggg cagaaaacat cgctgaccgc    1800
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920
actctttcac ttcaatttgt cgacagcgcc gcggatatgc cgcttgcgaa atgcacggt    1980 gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgcccct    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg aacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 26
<211> LENGTH: 1048
<212> TYPE: PRT
<213> ORGANISM: Bacillus megaterium

<400> SEQUENCE: 26

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
                 20                  25                  30

Ala Asp Glu Leu Gly Glu Ile Phe Lys Phe Glu Ala Pro Gly Cys Val
             35                  40                  45

Thr Arg Tyr Leu Ser Ser Gln Arg Leu Ile Lys Glu Ala Cys Asp Glu
         50                  55                  60

Ser Arg Phe Asp Lys Asn Leu Ser Gln Ala Leu Lys Phe Ala Arg Asp
 65                  70                  75                  80

Phe Gly Gly Asp Gly Leu Phe Thr Ser Trp Thr His Glu Ile Asn Trp
                 85                  90                  95
```

```
Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
            130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
            195                 200                 205

Ile Lys Val Met Asn Asp Leu Val Asp Lys Ile Ile Ala Asp Arg Lys
            210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
                275                 280                 285

Lys Val Ala Glu Glu Ala Ala Arg Val Leu Val Asp Pro Val Pro Ser
            290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
            370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510
```

-continued

```
Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
        610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
        690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
```

```
                930             935             940
Tyr Gln Glu Glu Leu Glu Asn Ala Gln Ser Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                 1000                1005

Val Glu Ala Thr Leu Met Lys Ser Tyr Ala Asp Val His Gln Val Ser
        1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 27
<211> LENGTH: 3144
<212> TYPE: DNA
<213> ORGANISM: Bacillus megaterium

<400> SEQUENCE: 27
acaattaaag aaatgcctca gccaaaaacg tttggagagc ttaaaaattt accgttatta      60
aacacagata aaccggttca agctttgatg aaaattgcgg atgaattagg agaaatcttt    120
aaattcgagg cgcctggttg tgtaacgcgc tacttatcaa gtcagcgtct aattaaagaa    180
gcatgcgatg aatcacgctt tgataaaaac ttaagtcaag cgcttaaatt tgcacgtgat    240
tttatcggag acgggttatt tacaagctgg acgcatgaaa taaattggaa aaaagcgcat    300
aatatcttac ttccaagctt tagtcagcag gcaatgaaag ctatcatgc gatgatggtc     360 gatatcgccg tgcagcttgt tcaaaagtgg gagcgtctaa atgcagatga gcatattgaa    420
gtatcggaag acatgacacg tttaacgctt gatacaattg gtctttgcgg ctttaactat    480
cgctttaaca gcttttaccg agatcagcct catccattta ttataagtat ggtccgtgca    540
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattaca    780
ttcttaattg cgggacacga aacaacaagt ggtcttttat catttgcgct gtatttctta    840
gtgaaaaatc cacatgtatt acaaaaagta gcagaagaag cagcacgagt tctagtagat    900
cctgttccaa gctacaaaca agtcaaacag cttaaatatg tcggcatggt cttaaacgaa    960
gcgctgcgct tatggccaac tgctcctgcg ttttccctat atgcaaaaga agatacggtg   1020
cttggaggag aatatccttt agaaaaaggc gacgaagtaa tggttctgat tcctcagctt   1080
caccgtgata aaacaattg gggagacgat gtggaggagt ccgtccaga gcgttttgaa    1140 aatccaagtg cgattccgca gcatgcgttt aaaccgtttg gaacggtca gcgtgcgtgt   1200 atcggtcagc agttcgctct tcatgaagca acgctggtac ttggtatgat gctaaaacac   1260
tttgactttg aagatcatac aaaactacgag ctcgatatta agaaacttt aacgttaaaa   1320 cctgaaggct tgtggtaaa agcaaaatcg aaaaaaattc cgcttggcgg tattccttca   1380
cctagcactg aacagtctgc taaaaaagta cgcaaaaagg cagaaaacgc tcataatacg   1440
```

-continued

```
ccgctgcttg tgctatacgg ttcaaatatg ggaacagctg aaggaacggc gcgtgattta    1500
gcagatattg caatgagcaa aggatttgca ccgcaggtcg caacgcttga ttcacacgcc    1560
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
ggcgttcgct actccgtatt tggatgcggc gataaaaact gggctactac gtatcaaaaa    1740
gtgcctgctt ttatcgatga aacgcttgcc gctaaggggg cagaaaacat cgctgaccgc    1800
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920
actctttcac ttcaatttgt cgacagcgcc gcggatatgc cgcttgcgaa aatgcacggt    1980
gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat cagcgaatt tatcgccctt    2460 ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa acgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 28
<211> LENGTH: 1048
<212> TYPE: PRT
<213> ORGANISM: Bacillus megaterium

<400> SEQUENCE: 28

```
Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
```

-continued

```
                65                  70                  75                  80
            Phe Ile Gly Asp Gly Leu Phe Thr Ser Trp Thr His Glu Ile Asn Trp
                            85                  90                  95
            Lys Lys Ala His Asn Ile Leu Leu Pro Ser Phe Ser Gln Gln Ala Met
                           100                 105                 110
            Lys Gly Tyr His Ala Met Met Val Asp Ile Ala Val Gln Leu Val Gln
                           115                 120                 125
            Lys Trp Glu Arg Leu Asn Ala Asp Glu His Ile Glu Val Ser Glu Asp
                           130                 135                 140
            Met Thr Arg Leu Thr Leu Asp Thr Ile Gly Leu Cys Gly Phe Asn Tyr
            145                 150                 155                 160
            Arg Phe Asn Ser Phe Tyr Arg Asp Gln Pro His Pro Phe Ile Ile Ser
                           165                 170                 175
            Met Val Arg Ala Leu Asp Glu Val Met Asn Lys Leu Gln Arg Ala Asn
                           180                 185                 190
            Pro Asp Asp Pro Ala Tyr Asp Glu Asn Lys Arg Gln Cys Gln Glu Asp
                           195                 200                 205
            Ile Lys Val Met Asn Asp Leu Val Asp Lys Ile Ile Ala Asp Arg Lys
                           210                 215                 220
            Ala Arg Gly Glu Gln Ser Asp Asp Leu Leu Thr Gln Met Leu Asn Gly
            225                 230                 235                 240
            Lys Asp Pro Glu Thr Gly Glu Pro Leu Asp Asp Gly Asn Ile Ser Tyr
                           245                 250                 255
            Gln Ile Ile Thr Phe Leu Ile Ala Gly His Glu Thr Thr Ser Gly Leu
                           260                 265                 270
            Leu Ser Phe Ala Leu Tyr Phe Leu Val Lys Asn Pro His Val Leu Gln
                           275                 280                 285
            Lys Val Ala Glu Glu Ala Ala Arg Val Leu Val Asp Pro Val Pro Ser
                           290                 295                 300
            Tyr Lys Gln Val Lys Gln Leu Lys Tyr Val Gly Met Val Leu Asn Glu
            305                 310                 315                 320
            Ala Leu Arg Leu Trp Pro Thr Ala Pro Ala Phe Ser Leu Tyr Ala Lys
                           325                 330                 335
            Glu Asp Thr Val Leu Gly Gly Glu Tyr Pro Leu Glu Lys Gly Asp Glu
                           340                 345                 350
            Val Met Val Leu Ile Pro Gln Leu His Arg Asp Lys Thr Ile Trp Gly
                           355                 360                 365
            Asp Asp Val Glu Glu Phe Arg Pro Glu Arg Phe Glu Asn Pro Ser Ala
                           370                 375                 380
            Ile Pro Gln His Ala Phe Lys Pro Phe Gly Asn Gly Gln Arg Ala Cys
            385                 390                 395                 400
            Ile Gly Gln Gln Phe Ala Leu His Glu Ala Thr Leu Val Leu Gly Met
                           405                 410                 415
            Met Leu Lys His Phe Asp Phe Glu Asp His Thr Asn Tyr Glu Leu Asp
                           420                 425                 430
            Ile Lys Glu Thr Leu Thr Leu Lys Pro Glu Gly Phe Val Val Lys Ala
                           435                 440                 445
            Lys Ser Lys Lys Ile Pro Leu Gly Gly Ile Pro Ser Pro Ser Thr Glu
                           450                 455                 460
            Gln Ser Ala Lys Lys Val Arg Lys Lys Ala Glu Asn Ala His Asn Thr
            465                 470                 475                 480
            Pro Leu Leu Val Leu Tyr Gly Ser Asn Met Gly Thr Ala Glu Gly Thr
                           485                 490                 495
```

```
Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910
```

-continued

```
Phe Val Gln Ala Arg Lys Gln Leu Lys Glu Gln Gly Gln Ser Leu Gly
        915                 920                 925
Glu Ala His Leu Tyr Phe Gly Cys Arg Ser Pro His Glu Asp Tyr Leu
    930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
        995                 1000                1005
Val Glu Ala Thr Leu Met Lys Ser Tyr Ala Asp Val His Gln Val Ser
    1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
                1045
```

<210> SEQ ID NO 29
<211> LENGTH: 3144
<212> TYPE: DNA
<213> ORGANISM: Bacillus megaterium

<400> SEQUENCE: 29

```
acaattaaag aaatgcctca gccaaaaacg tttggagagc ttaaaaattt accgttatta     60
aacacagata aaccggttca agctttgatg aaaattgcgg atgaattagg agaaatctttt    120
aaattcgagg cgcctggttg tgtaacgcgc tacttatcaa gtcagcgtct aattaaagaa    180
gcatgcgatg aatcacgctt tgataaaaac ttaagtcaag cgcttaaatt tgcacgtgat    240
tttcttggag acgggttatt tacaagctgg acgcatgaaa taaattggaa aaaagcgcat    300
aatatcttac ttccaagctt tagtcagcag gcaatgaaag ctatcatgc gatgatggtc    360
gatatcgccg tgcagcttgt tcaaaagtgg gagcgtctaa atgcagatga gcatattgaa    420
gtatcggaag acatgacacg tttaacgctt gatacaattg gtctttgcgg ctttaactat    480
cgcttttaaca gcttttaccg agatcagcct catccattta ttataagtat ggtccgtgca    540
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattaca    780
ttcttaattg cgggacacga aacaacaagt ggtcttttat catttgcgct gtattcctta    840
gtgaaaaatc cacatgtatt acaaaaagta gcagaagaag cagcacgagt tctagtagat    900
cctgttccaa gctacaaaca agtcaaacag cttaaatatg tcggcatggt cttaaacgaa    960
gcgctgcgct tatggccaac tgctcctgcg tttttccctat atgcaaaaga agatacggtg    1020
cttggaggag aatatccttt agaaaaggc gacgaagtaa tggttctgat tcctcagctt    1080
caccgtgata aaacaatttg gggagacgat gtggaggagt tccgtccaga gcgttttgaa    1140
aatccaagtg cgattccgca gcatgcgttt aaaccgtttg gaaacggtca gcgtgcgtgt    1200
atcggtcagc agttcgctct tcatgaagca acgctggtac ttggtatgat gctaaaacac    1260
tttgactttg aagatcatac aaactacgag ctcgatatta agaaactttt aacgttaaaa    1320
```

```
cctgaaggct tgtgggtaaa agcaaaatcg aaaaaaattc cgcttggcgg tattccttca    1380
cctagcactg aacagtctgc taaaaaagta cgcaaaaagg cagaaaacgc tcataatacg    1440
ccgctgcttg tgctatacgg ttcaaatatg gaacagctg  aaggaacggc gcgtgattta    1500
gcagatattg caatgagcaa aggatttgca ccgcaggtcg caacgcttga ttcacacgcc    1560
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
ggcgttcgct actccgtatt tggatgcggc gataaaaact gggctactac gtatcaaaaa    1740
gtgcctgctt ttatcgatga aacgcttgcc gctaaagggg cagaaaacat cgctgaccgc    1800
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920
actctttcac ttcaatttgt cgacagcgcc gcggatatgc cgcttgcgaa aatgcacggt    1980
gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacga tatccgtaga agagcttctg caatacgtgg agcttcaaga tcctgttacg    2280
cgcacgcagc ttcgcgcaat ggctgctaaa acggtctgcc cgccgcataa agtagagctt    2340 gaagcccttgc ttgaaaagca agcctacaaa gaacaagtgc tggcaaaacg tttaacaatg    2400
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 30
<211> LENGTH: 1048
<212> TYPE: PRT
<213> ORGANISM: Bacillus megaterium

<400> SEQUENCE: 30

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

```
Thr Arg Tyr Leu Ser Ser Gln Arg Leu Ile Lys Glu Ala Cys Asp Glu
 50                  55                  60

Ser Arg Phe Asp Lys Asn Leu Ser Gln Ala Leu Lys Phe Ala Arg Asp
 65                  70                  75                  80

Phe Leu Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Ser Glu Asp
130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
            195                 200                 205

Ile Lys Val Met Asn Asp Leu Val Asp Lys Ile Ile Ala Asp Arg Lys
210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Val Ala Glu Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
```

```
                465                 470                 475                 480
Pro Leu Leu Val Leu Tyr Gly Ser Asn Met Gly Thr Ala Glu Gly Thr
                    485                 490                 495
Ala Arg Asp Leu Ala Asp Ile Ala Met Ser Lys Gly Phe Ala Pro Gln
                500                 505                 510
Val Ala Thr Leu Asp Ser His Ala Gly Asn Leu Pro Arg Glu Gly Ala
                515                 520                 525
Val Leu Ile Val Thr Ala Ser Tyr Asn Gly His Pro Pro Asp Asn Ala
            530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
                580                 585                 590
Gly Ala Glu Asn Ile Ala Asp Arg Gly Glu Ala Asp Ala Ser Asp Asp
                595                 600                 605
Phe Glu Gly Thr Tyr Glu Glu Trp Arg Glu His Met Trp Ser Asp Val
            610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
                675                 680                 685
Pro Lys Glu Ala Ser Tyr Gln Glu Gly Asp His Leu Gly Val Ile Pro
            690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Glu Leu Leu Gln Tyr
                740                 745                 750
Val Glu Leu Gln Asp Pro Val Thr Arg Thr Gln Leu Arg Ala Met Ala
            755                 760                 765
Ala Lys Thr Val Cys Pro Pro His Lys Val Glu Leu Glu Ala Leu Leu
            770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
                820                 825                 830
Ser Ser Pro Arg Val Asp Glu Lys Gln Ala Ser Ile Thr Val Ser Val
            835                 840                 845
Val Ser Gly Glu Ala Trp Ser Gly Tyr Gly Glu Tyr Lys Gly Ile Ala
            850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
```

-continued

```
Pro Leu Ile Met Val Gly Pro Gly Thr Gly Val Ala Pro Phe Arg Gly
            900                 905                 910
Phe Val Gln Ala Arg Lys Gln Leu Lys Glu Gln Gly Gln Ser Leu Gly
            915                 920                 925
Glu Ala His Leu Tyr Phe Gly Cys Arg Ser Pro His Glu Asp Tyr Leu
            930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
            995                 1000                1005
Val Glu Ala Thr Leu Met Lys Ser Tyr Ala Asp Val His Gln Val Ser
    1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
            1045
```

<210> SEQ ID NO 31
<211> LENGTH: 3144
<212> TYPE: DNA
<213> ORGANISM: Bacillus megaterium

<400> SEQUENCE: 31

```
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgcttaaatt tgcacgtgat     240
ttttcaggag acgggttatt tacaagctgg acgcatgaaa taaattggaa aaaagcgcat     300
aatatcttac ttccaagctt tagtcagcag gcaatgaaag gctatcatgc gatgatggtc     360
gatatcgccg tgcagcttgt tcaaaagtgg gagcgtctaa atgcagatga gcatattgaa     420
gtatcggaag acatgacacg tttaacgctt gatacaattg gtctttgcgg ctttaactat     480
cgctttaaca gcttttaccg agatcagcct catccatttt tataagtat ggtccgtgca     540
ctggatgaag taatgaacaa gctgcagcga gcaaatccag acgacccagc ttatgatgaa     600
aacaagcgcc agtgtcaaga agatatcaag gtgatgaacg acctagtaga taaaattatt     660
gcagatcgca aagcaagggg tgaacaaagc gatgatttat taacgcagat gctaaacgga     720
aaagatccag aaacgggtga gccgcttgat gacgggaaca ttagctatca aattattaca     780
ttcttaattg cgggacacga aacaacaagt ggtctttat catttgcgct gtatttctta     840
gtgaaaaatc cacatgtatt acaaaaaagta gcagaagaag cagcacgagt tctagtagat     900
cctgttccaa gctacaaaca agtcaaacag cttaaatatg tcggcatggt cttaaacgaa     960
gcgctgcgct atggccaac tgctcctgcg ttttccctat atgcaaaaga agatacggtg    1020
cttggaggag aatatccttt agaaaaaggc gacgaagtaa tggttctgat tcctcagctt    1080
caccgtgata aacaatttg gggagacgat gtggaggagt tccgtccaga gcgttttgaa    1140
aatccaagtg cgattccgca gcatgcgttt aaaccgtttg gaacggtca gcgtgcgtgt    1200
```

-continued

```
atcggtcagc agttcgctct tcatgaagca acgctggtac ttggtatgat gctaaaacac    1260
tttgactttg aagatcatac aaactacgag ctcgatatta agaaactttt aacgttaaaa    1320
cctgaaggct ttgtggtaaa agcaaaatcg aaaaaaattc cgcttggcgg tattccttca    1380
cctagcactg aacagtctgc taaaaaagta cgcaaaaagg cagaaaacgc tcataatacg    1440
ccgctgcttg tgctatacgg ttcaaatatg gaacagctg aaggaacggc gcgtgattta     1500
gcagatattg caatgagcaa aggatttgca ccgcaggtcg caacgcttga ttcacacgcc    1560
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
ggcgttcgct actccgtatt tggatgcggc gataaaaact gggctactac gtatcaaaaa    1740
gtgcctgctt ttatcgatga aacgcttgcc gctaaagggg cagaaaacat cgctgaccgc    1800
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920
actctttcac ttcaatttgt cgacagcgcc gcggatatgc cgcttgcgaa atgcacggt     1980 gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgcccct    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 32
<211> LENGTH: 1048
<212> TYPE: PRT
<213> ORGANISM: Bacillus megaterium

<400> SEQUENCE: 32

```
Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
             20                  25                  30
```

-continued

```
Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
 65                  70                  75                  80

Phe Ser Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
                100                 105                 110

Lys Gly Tyr His Ala Met Met Val Asp Ile Ala Val Gln Leu Val Gln
             115                 120                 125

Lys Trp Glu Arg Leu Asn Ala Asp Glu His Ile Glu Val Ser Glu Asp
 130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                 165                 170                 175

Met Val Arg Ala Leu Asp Glu Val Met Asn Lys Leu Gln Arg Ala Asn
                 180                 185                 190

Pro Asp Asp Pro Ala Tyr Asp Glu Asn Lys Arg Gln Cys Gln Glu Asp
             195                 200                 205

Ile Lys Val Met Asn Asp Leu Val Asp Lys Ile Ala Asp Arg Lys
 210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                 245                 250                 255

Gln Ile Ile Thr Phe Leu Ile Ala Gly His Glu Thr Thr Ser Gly Leu
             260                 265                 270

Leu Ser Phe Ala Leu Tyr Phe Leu Val Lys Asn Pro His Val Leu Gln
         275                 280                 285

Lys Val Ala Glu Glu Ala Ala Arg Val Leu Val Asp Pro Val Pro Ser
 290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                 325                 330                 335

Glu Asp Thr Val Leu Gly Gly Glu Tyr Pro Leu Glu Lys Gly Asp Glu
             340                 345                 350

Val Met Val Leu Ile Pro Gln Leu His Arg Asp Lys Thr Ile Trp Gly
         355                 360                 365

Asp Asp Val Glu Glu Phe Arg Pro Glu Arg Phe Glu Asn Pro Ser Ala
 370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                 405                 410                 415

Met Leu Lys His Phe Asp Phe Glu Asp His Thr Asn Tyr Glu Leu Asp
             420                 425                 430

Ile Lys Glu Thr Leu Thr Leu Lys Pro Glu Gly Phe Val Val Lys Ala
         435                 440                 445
```

-continued

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe

```
                865                 870                 875                 880
        Ile Ser Thr Pro Gln Ser Glu Phe Thr Leu Pro Lys Asp Pro Glu Thr
                        885                 890                 895

Pro Leu Ile Met Val Gly Pro Gly Thr Gly Val Ala Pro Phe Arg Gly
                    900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
                930                 935                 940

Tyr Gln Glu Glu Leu Glu Asn Ala Gln Ser Glu Gly Ile Ile Thr Leu
        945                 950                 955                 960

His Thr Ala Phe Ser Arg Met Pro Asn Gln Pro Lys Thr Tyr Val Gln
                        965                 970                 975

His Val Met Glu Gln Asp Gly Lys Lys Leu Ile Glu Leu Leu Asp Gln
                    980                 985                 990

Gly Ala His Phe Tyr Ile Cys Gly Asp Gly Ser Gln Met Ala Pro Ala
                995                 1000                1005

Val Glu Ala Thr Leu Met Lys Ser Tyr Ala Asp Val His Gln Val Ser
            1010                1015                1020

Glu Ala Asp Ala Arg Leu Trp Leu Gln Gln Leu Glu Glu Lys Gly Arg
        1025                1030                1035                1040

Tyr Ala Lys Asp Val Trp Ala Gly
                    1045

<210> SEQ ID NO 33
<211> LENGTH: 3144
<212> TYPE: DNA
<213> ORGANISM: Bacillus megaterium

<400> SEQUENCE: 33
acaattaaag aaatgcctca gccaaaaacg tttggagagc ttaaaaattt accgttatta      60
aacacagata aaccggttca agctttgatg aaaattgcgg atgaattagg agaaatctt     120 aaattcgagc gcctggttg tgtaacgcgc tacttatcaa gtcagcgtct aattaaagaa     180
gcatgcgatg aatcacgctt tgataaaaac ttaagtcaag cgcttaaatt tgcacgtgat     240
tttacaggag acgggttatt tacaagctgg acgcatgaaa taaattggaa aaaagcgcat     300
aatatcttac ttccaagctt tagtcagcag gcaatgaaag ctatcatgc gatgatggtc     360 gatatcgccg tgcagcttgt tcaaaagtgg gagcgtctaa atgcagatga gcatattgaa     420
gtatcggaag acatgacacg tttaacgctt gatacaattg gtctttgcgg ctttaactat     480
cgctttaaca gcttttaccg agatcagcct catccattta ttataagtat ggtccgtgca     540
ctggatgaag taatgaacaa gctgcagcga gcaaatccag acgacccagc ttatgatgaa     600
aacaagcgcc agtgtcaaga agatatcaag gtgatgaacg acctagtaga taaaattatt     660
gcagatcgca aagcaagggg tgaacaaagc gatgatttat aacgcagat gctaaacgga     720 aaagatccag aaacgggtga gccgcttgat gacgggaaca ttagctatca aattattaca     780
ttcttaattg cgggacacga acaacaagt ggtctttat catttgcgct gtatttctta     840
gtgaaaaatc cacatgtatt acaaaaagta gcagaagaag cagcacgagt tctagtagat     900
cctgttccaa gctacaaaca agtcaaacag cttaaatatg tcggcatggt cttaaacgaa     960
gcgctgcgct atggccaac tgctcctgcg ttttccctat atgcaaaaga agatacggtg    1020
cttggaggag aaatatcctt tagaaaaggc gacgaagtaa tggttctgat tcctcagctt    1080
```

-continued

```
caccgtgata aaacaatttg gggagacgat gtggaggagt tccgtccaga gcgttttgaa      1140
aatccaagtg cgattccgca gcatgcgttt aaaccgtttg aaacggtca gcgtgcgtgt       1200 atcggtcagc agttcgctct tcatgaagca acgctggtac ttggtatgat gctaaaacac     1260
tttgactttg aagatcatac aaactacgag ctcgatatta agaaacttt aacgttaaaa     1320 cctgaaggct ttgtggtaaa agcaaaatcg aaaaaattc cgcttggcgg tattccttca      1380
cctagcactg aacagtctgc taaaaagta cgcaaaagg cagaaaacgc tcataatacg       1440
ccgctgcttg tgctatacgg ttcaaatatg gaacagctg aaggaacggc gcgtgattta      1500
gcagatattg caatgagcaa aggatttgca ccgcaggtcg caacgcttga ttcacacgcc     1560
ggaaatcttc cgcgcgaagg agctgtatta attgtaacgg cgtcttataa cggtcatccg     1620
cctgataacg caaagcaatt tgtcgactgg ttagaccaag cgtctgctga tgaagtaaaa     1680
ggcgttcgct actccgtatt tggatgcggc gataaaaact gggctactac gtatcaaaaa   1740
gtgcctgctt ttatcgatga aacgcttgcc gctaaagggg cagaaaacat cgctgaccgc     1800
ggtgaagcag atgcaagcga cgactttgaa ggcacatatg aagaatggcg tgaacatatg     1860
tggagtgacg tagcagccta ctttaacctc gacattgaaa acagtgaaga taataaatct    1920
actctttcac ttcaatttgt cgacagcgcc gcggatatgc cgcttgcgaa atgcacggt      1980 gcgttttcaa cgaacgtcgt agcaagcaaa gaacttcaac agccaggcag tgcacgaagc     2040
acgcgacatc ttgaaattga acttccaaaa gaagcttctt atcaagaagg agatcattta     2100
ggtgttattc ctcgcaacta tgaaggaata gtaaaccgtg taacagcaag gttcggccta     2160
gatgcatcac agcaaatccg tctggaagca gaagaagaaa aattagctca tttgccactc     2220
gctaaaacag tatccgtaga agagcttctg caatacgtgg agcttcaaga tcctgttacg     2280
cgcacgcagc ttcgcgcaat ggctgctaaa acggtctgcc cgccgcataa agtagagctt     2340
gaagccttgc ttgaaaagca agcctacaaa gaacaagtgc tggcaaaacg tttaacaatg     2400
cttgaactgc ttgaaaaata cccggcgtgt gaaatgaaat tcagcgaatt tatcgcccttt   2460 ctgccaagca tacgcccgcg ctattactcg atttcttcat cacctcgtgt cgatgaaaaa    2520
caagcaagca tcacggtcag cgttgtctca ggagaagcgt ggagcggata tggagaatat     2580
aaaggaattg cgtcgaacta tcttgccgag ctgcaagaag gagatacgat tacgtgcttt     2640
atttccacac cgcagtcaga atttacgctg ccaaaagacc ctgaaacgcc gcttatcatg      2700
gtcggaccgg gaacaggcgt cgcgccgttt agaggctttg tgcaggcgcg caaacagcta     2760
aaagaacaag gacagtcact tggagaagca catttatact tcggctgccg ttcacctcat     2820
gaagactatc tgtatcaaga agagcttgaa aacgcccaaa gcgaaggcat cattacgctt     2880
cataccgctt tttctcgcat gccaaatcag ccgaaaacat acgttcagca cgtaatggaa     2940
caagacggca agaaattgat tgaacttctt gatcaaggag cgcacttcta tatttgcgga     3000
gacggaagcc aaatggcacc tgccgttgaa gcaacgctta tgaaaagcta tgctgacgtt     3060
caccaagtga gtgaagcaga cgctcgctta tggctgcagc agctagaaga aaaaggccga     3120
tacgcaaaag acgtgtgggc tggg                                              3144
```

<210> SEQ ID NO 34
<211> LENGTH: 1048
<212> TYPE: PRT
<213> ORGANISM: Bacillus megaterium

<400> SEQUENCE: 34

Thr Ile Lys Glu Met Pro Gln Pro Lys Thr Phe Gly Glu Leu Lys Asn

-continued

```
  1               5                  10                 15
Leu Pro Leu Leu Asn Thr Asp Lys Pro Val Gln Ala Leu Met Lys Ile
                20                 25                 30

Ala Asp Glu Leu Gly Glu Ile Phe Lys Phe Glu Ala Pro Gly Cys Val
                35                 40                 45

Thr Arg Tyr Leu Ser Ser Gln Arg Leu Ile Lys Glu Ala Cys Asp Glu
                50                 55                 60

Ser Arg Phe Asp Lys Asn Leu Ser Gln Ala Leu Lys Phe Ala Arg Asp
 65                 70                 75                 80

Phe Thr Gly Asp Gly Leu Phe Thr Ser Trp Thr His Glu Ile Asn Trp
                85                 90                 95

Lys Lys Ala His Asn Ile Leu Leu Pro Ser Phe Ser Gln Gln Ala Met
               100                105                110

Lys Gly Tyr His Ala Met Met Val Asp Ile Ala Val Gln Leu Val Gln
               115                120                125

Lys Trp Glu Arg Leu Asn Ala Asp Glu His Ile Glu Val Ser Glu Asp
               130                135                140

Met Thr Arg Leu Thr Leu Asp Thr Ile Gly Leu Cys Gly Phe Asn Tyr
145                150                155                160

Arg Phe Asn Ser Phe Tyr Arg Asp Gln Pro His Pro Phe Ile Ile Ser
               165                170                175

Met Val Arg Ala Leu Asp Glu Val Met Asn Lys Leu Gln Arg Ala Asn
               180                185                190

Pro Asp Asp Pro Ala Tyr Asp Glu Asn Lys Arg Gln Cys Gln Glu Asp
               195                200                205

Ile Lys Val Met Asn Asp Leu Val Asp Lys Ile Ala Asp Arg Lys
               210                215                220

Ala Arg Gly Glu Gln Ser Asp Asp Leu Leu Thr Gln Met Leu Asn Gly
225                230                235                240

Lys Asp Pro Glu Thr Gly Glu Pro Leu Asp Asp Gly Asn Ile Ser Tyr
               245                250                255

Gln Ile Ile Thr Phe Leu Ile Ala Gly His Glu Thr Thr Ser Gly Leu
               260                265                270

Leu Ser Phe Ala Leu Tyr Phe Leu Val Lys Asn Pro His Val Leu Gln
               275                280                285

Lys Val Ala Glu Glu Ala Ala Arg Val Leu Val Asp Pro Val Pro Ser
               290                295                300

Tyr Lys Gln Val Lys Gln Leu Lys Tyr Val Gly Met Val Leu Asn Glu
305                310                315                320

Ala Leu Arg Leu Trp Pro Thr Ala Pro Ala Phe Ser Leu Tyr Ala Lys
               325                330                335

Glu Asp Thr Val Leu Gly Gly Glu Tyr Pro Leu Glu Lys Gly Asp Glu
               340                345                350

Val Met Val Leu Ile Pro Gln Leu His Arg Asp Lys Thr Ile Trp Gly
               355                360                365

Asp Asp Val Glu Glu Phe Arg Pro Glu Arg Phe Glu Asn Pro Ser Ala
               370                375                380

Ile Pro Gln His Ala Phe Lys Pro Phe Gly Asn Gly Gln Arg Ala Cys
385                390                395                400

Ile Gly Gln Gln Phe Ala Leu His Glu Ala Thr Leu Val Leu Gly Met
               405                410                415

Met Leu Lys His Phe Asp Phe Glu Asp His Thr Asn Tyr Glu Leu Asp
               420                425                430
```

```
Ile Lys Glu Thr Leu Thr Leu Lys Pro Glu Gly Phe Val Lys Ala
            435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
                500                 505                 510
Val Ala Thr Leu Asp Ser His Ala Gly Asn Leu Pro Arg Glu Gly Ala
                515                 520                 525
Val Leu Ile Val Thr Ala Ser Tyr Asn Gly His Pro Pro Asp Asn Ala
                530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
                580                 585                 590
Gly Ala Glu Asn Ile Ala Asp Arg Gly Glu Ala Asp Ala Ser Asp Asp
                595                 600                 605
Phe Glu Gly Thr Tyr Glu Glu Trp Arg Glu His Met Trp Ser Asp Val
                610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
                660                 665                 670
Gln Gln Pro Gly Ser Ala Arg Ser Thr Arg His Leu Glu Ile Glu Leu
                675                 680                 685
Pro Lys Glu Ala Ser Tyr Gln Glu Gly Asp His Leu Gly Val Ile Pro
                690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Glu Leu Leu Gln Tyr
                740                 745                 750
Val Glu Leu Gln Asp Pro Val Thr Arg Thr Gln Leu Arg Ala Met Ala
                755                 760                 765
Ala Lys Thr Val Cys Pro Pro His Lys Val Glu Leu Glu Ala Leu Leu
                770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
                820                 825                 830
Ser Ser Pro Arg Val Asp Glu Lys Gln Ala Ser Ile Thr Val Ser Val
                835                 840                 845
```

```
Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                    885                 890                 895

Pro Leu Ile Met Val Gly Pro Thr Gly Val Ala Pro Phe Arg Gly
                900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 35
<211> LENGTH: 3144

<212> TYPE: DNA
<213> ORGANISM: Bacillus megaterium

<400> SEQUENCE: 35
acaattaaag aaatgcctca gccaaaaacg tttggagagc ttaaaaattt accgttatta      60
aacacagata aaccggttca agctttgatg aaaattgcgg atgaattagg agaaatctttt   120 aaattcgagg cgcctggttg tgtaacgcgc tacttatcaa gtcagcgtct aattaaagaa    180
gcatgcgatg aatcacgctt tgataaaaac ttaagtcaag cgcttaaatt tgcacgtgat    240
tttgcaggag acgggttaat aacaagctgg acgcatgaaa taaattggaa aaaagcgcat    300
aatatcttac ttccaagctt tagtcagcag gcaatgaaag ctatcatgc gatgatggtc      360 gatatcgccg tgcagcttgt tcaaaagtgg gagcgtctaa atgcagatga gcatattgaa    420
gtatcggaag acatgacacg tttaacgctt gatacaattg gtctttgcgg ctttaactat    480
cgctttaaca gcttttaccg agatcagcct catccattta ttataagtat ggtccgtgca    540
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattaca    780
ttcttaattg cgggacacga aacaacaagt ggtctttat catttgcgct gtatttctta    840
```

-continued

```
gtgaaaaatc cacatgtatt acaaaaagta gcagaagaag cagcacgagt tctagtagat      900
cctgttccaa gctacaaaca agtcaaacag cttaaatatg tcggcatggt cttaaacgaa      960
gcgctgcgct tatggccaac tgctcctgcg ttttccctat atgcaaaaga agatacggtg     1020
cttggaggag aatatccttt agaaaaaggc gacgaagtaa tggttctgat tcctcagctt     1080
caccgtgata aaacaatttg gggagacgat gtggaggagt tccgtccaga gcgttttgaa     1140
aatccaagtg cgattccgca gcatgcgttt aaaccgtttg gaaacggtca gcgtgcgtgt     1200
atcggtcagc agttcgctct tcatgaagca acgctggtac ttggtatgat gctaaaacac     1260
tttgactttg aagatcatac aaactacgag ctcgatatta agaaactttt aacgttaaaa     1320
cctgaaggct tgtggtaaa agcaaaatcg aaaaaaattc cgcttggcgg tattccttca     1380
cctagcactg aacagtctgc taaaaaagta cgcaaaaagg cagaaaacgc tcataatacg     1440
ccgctgcttg tgctatacgg ttcaaatatg ggaacagctg aaggaacggc gcgtgattta     1500
gcagatattg caatgagcaa aggatttgca ccgcaggtcg caacgcttga ttcacacgcc     1560
ggaaatcttc cgcgcgaagg agctgtatta attgtaacgg cgtcttataa cggtcatccg     1620
cctgataacg caaagcaatt tgtcgactgg ttagaccaag cgtctgctga tgaagtaaaa     1680
ggcgttcgct actccgtatt tggatgcggc gataaaaact gggctactac gtatcaaaaa     1740
gtgcctgctt ttatcgatga aacgcttgcc gctaaagggg cagaaaacat cgctgaccgc     1800
ggtgaagcag atgcaagcga cgactttgaa ggcacatatg aagaatggcg tgaacatatg     1860
tggagtgacg tagcagccta ctttaacctc gacattgaaa acagtgaaga taataaatct     1920
actctttcac ttcaatttgt cgacagcgcc gcggatatgc cgcttgcgaa aatgcacggt     1980
gcgttttcaa cgaacgtcgt agcaagcaaa gaacttcaac agccaggcag tgcacgaagc     2040
acgcgacatc ttgaaattga acttccaaaa gaagcttctt atcaagaagg agatcattta     2100
ggtgttattc ctcgcaacta tgaaggaata gtaaaccgtg taacagcaag gttcggccta     2160
gatgcatcac agcaaatccg tctggaagca gaagaagaaa aattagctca tttgccactc     2220
gctaaaacag tatccgtaga agagcttctg caatacgtgg agcttcaaga tcctgttacg     2280
cgcacgcagc ttcgcgcaat ggctgctaaa acggtctgcc cgccgcataa agtagagctt     2340
gaagccttgc ttgaaaagca agcctacaaa gaacaagtgc tggcaaaacg tttaacaatg     2400
cttgaactgc ttgaaaaata cccggcgtgt gaaatgaaat tcagcgaatt tatcgcccct     2460
ctgccaagca tacgcccgcg ctattactcg atttcttcat cacctcgtgt cgatgaaaaa     2520
caagcaagca tcacggtcag cgttgtctca ggagaagcgt ggagcggata tggagaatat     2580
aaaggaattg cgtcgaacta tcttgccgag ctgcaagaag gagatacgat tacgtgcttt     2640
atttccacac cgcagtcaga atttacgctg ccaaaagacc ctgaaacgcc gcttatcatg     2700
gtcggaccgg gaacaggcgt cgcgccgttt agaggctttg tgcaggcgcg caaacagcta     2760
aaagaacaag gacagtcact tggagaagca catttatact tcggctgccg ttcacctcat     2820
gaagactatc tgtatcaaga agagcttgaa aacgcccaaa gcgaaggcat cattacgctt     2880
cataccgctt tttctcgcat gccaaatcag ccgaaaacat acgttcagca cgtaatggaa     2940
caagacggca agaaattgat tgaacttctt gatcaaggag cgcacttcta tatttgcgga     3000
gacggaagcc aaatggcacc tgccgttgaa gcaacgctta tgaaaagcta tgctgacgtt     3060
caccaagtga gtgaagcaga cgctcgctta tggctgcagc agctagaaga aaaaggccga     3120
tacgcaaaag acgtgtgggc tggg                                           3144
```

<210> SEQ ID NO 36
<211> LENGTH: 1048
<212> TYPE: PRT
<213> ORGANISM: Bacillus megaterium

<400> SEQUENCE: 36

```
Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Ile Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380
```

-continued

```
Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
        420                 425                 430

Ile Lys Glu Thr Leu Thr Leu Lys Pro Glu Gly Phe Val Val Lys Ala
    435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
```

```
                    805                 810                 815
Phe Ile Ala Leu Leu Pro Ser Ile Arg Pro Arg Tyr Tyr Ser Ile Ser
                820                 825                 830
Ser Ser Pro Arg Val Asp Glu Lys Gln Ala Ser Ile Thr Val Ser Val
            835                 840                 845
Val Ser Gly Glu Ala Trp Ser Gly Tyr Gly Glu Tyr Lys Gly Ile Ala
        850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
                900                 905                 910
Phe Val Gln Ala Arg Lys Gln Leu Lys Glu Gln Gly Gln Ser Leu Gly
            915                 920                 925
Glu Ala His Leu Tyr Phe Gly Cys Arg Ser Pro His Glu Asp Tyr Leu
        930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
                980                 985                 990
Gly Ala His Phe Tyr Ile Cys Gly Asp Gly Ser Gln Met Ala Pro Ala
            995                 1000                1005
Val Glu Ala Thr Leu Met Lys Ser Tyr Ala Asp Val His Gln Val Ser
    1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
            1045

<210> SEQ ID NO 37
<211> LENGTH: 3144
<212> TYPE: DNA
<213> ORGANISM: Bacillus megaterium

<400> SEQUENCE: 37
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgcttaaatt tgcacgtgat     240
tttgcaggag acgggttatt gacaagctgg acgcatgaaa taaattggaa aaaagcgcat     300
aatatcttac ttccaagctt tagtcagcag gcaatgaaag gctatcatgc gatgatggtc     360
gatatcgccg tgcagcttgt tcaaaagtgg gagcgtctaa atgcagatga gcatattgaa     420
gtatcggaag acatgacacg tttaacgctt gatacaattg gtctttgcgg cttttaactat     480 cgctttaaca gcttttaccg agatcagcct catccattta ttataagtat ggtccgtgca     540
ctggatgaag taatgaacaa gctgcagcga gcaaatccag acgacccagc ttatgatgaa     600
aacaagcgcc agtgtcaaga agatatcaag gtgatgaacg acctagtaga taaaattatt     660
gcagatcgca aagcaagggg tgaacaaagc gatgatttat taacgcagat gctaaacgga     720
```

-continued

| | | | | |
|---|---|---|---|---|
| aaagatccag | aaacgggtga | gccgcttgat | gacgggaaca | ttagctatca aattattaca | 780 |
| ttcttaattg | cgggacacga | aacaacaagt | ggtcttttat | catttgcgct gtatttctta | 840 |
| gtgaaaaatc | cacatgtatt | acaaaaagta | gcagaagaag | cagcacgagt tctagtagat | 900 |
| cctgttccaa | gctacaaaca | agtcaaacag | cttaaatatg | tcggcatggt cttaaacgaa | 960 |
| gcgctgcgct | tatggccaac | tgctcctgcg | ttttccctat | atgcaaaaga agatacggtg | 1020 |
| cttggaggag | aatatccttt | agaaaaaggc | gacgaagtaa | tggttctgat tcctcagctt | 1080 |
| caccgtgata | aaacaatttg | gggagacgat | gtggaggagt | tccgtccaga gcgttttgaa | 1140 |
| aatccaagtg | cgattccgca | gcatgcgttt | aaaccgtttg | gaaacggtca gcgtgcgtgt | 1200 |
| atcggtcagc | agttcgctct | tcatgaagca | acgctggtac | ttggtatgat gctaaaacac | 1260 |
| tttgactttg | aagatcatac | aaactacgag | ctcgatatta | agaaactttt aacgttaaaa | 1320 |
| cctgaaggct | tgtggtaaa | agcaaaatcg | aaaaaaattc | cgcttggcgg tattccttca | 1380 |
| cctagcactg | aacagtctgc | taaaaaagta | cgcaaaaagg | cagaaaacgc tcataatacg | 1440 |
| ccgctgcttg | tgctatacgg | ttcaaatatg | ggaacagctg | aaggaacggc gcgtgattta | 1500 |
| gcagatattg | caatgagcaa | aggatttgca | ccgcaggtcg | caacgcttga ttcacacgcc | 1560 |
| ggaaatcttc | cgcgcgaagg | agctgtatta | attgtaacgg | cgtcttataa cggtcatccg | 1620 |
| cctgataacg | caaagcaatt | tgtcgactgg | ttagaccaag | cgtctgctga tgaagtaaaa | 1680 |
| ggcgttcgct | actccgtatt | tggatgcggc | gataaaaact | gggctactac gtatcaaaaa | 1740 |
| gtgcctgctt | ttatcgatga | aacgcttgcc | gctaaagggg | cagaaaacat cgctgaccgc | 1800 |
| ggtgaagcag | atgcaagcga | cgactttgaa | ggcacatatg | aagaatggcg tgaacatatg | 1860 |
| tggagtgacg | tagcagccta | ctttaacctc | gacattgaaa | acagtgaaga taataaatct | 1920 |
| actcttttcac | ttcaatttgt | cgacagcgcc | gcggatatgc | cgcttgcgaa aatgcacggt | 1980 |
| gcgttttcaa | cgaacgtcgt | agcaagcaaa | gaacttcaac | agccaggcag tgcacgaagc | 2040 |
| acgcgacatc | ttgaaattga | acttccaaaa | gaagcttctt | atcaagaagg agatcattta | 2100 |
| ggtgttattc | ctcgcaacta | tgaaggaata | gtaaaccgtg | taacagcaag gttcggccta | 2160 |
| gatgcatcac | agcaaatccg | tctggaagca | gaagaagaaa | aattagctca tttgccactc | 2220 |
| gctaaaacag | tatccgtaga | agagcttctg | caatacgtgg | agcttcaaga tcctgttacg | 2280 |
| cgcacgcagc | ttcgcgcaat | ggctgctaaa | acggtctgcc | cgccgcataa agtagagctt | 2340 |
| gaagccttgc | ttgaaaagca | agcctacaaa | gaacaagtgc | tggcaaaacg tttaacaatg | 2400 |
| cttgaactgc | ttgaaaaata | cccggcgtgt | gaaatgaaat | tcagcgaatt tatcgcccctt | 2460 |
| ctgccaagca | tacgcccgcg | ctattactcg | atttcttcat | cacctcgtgt cgatgaaaaa | 2520 |
| caagcaagca | tcacggtcag | cgttgtctca | ggagaagcgt | ggagcggata tggagaatat | 2580 |
| aaaggaattg | cgtcgaacta | tcttgccgag | ctgcaagaag | gagatacgat tacgtgcttt | 2640 |
| atttccacac | cgcagtcaga | atttacgctg | ccaaaagacc | ctgaaacgcc gcttatcatg | 2700 |
| gtcggaccgg | gaacaggcgt | cgcgccgttt | agaggctttg | tgcaggcgcg caaacagcta | 2760 |
| aaagaacaag | gacagtcact | tggagaagca | catttatact | tcggctgccg ttcacctcat | 2820 |
| gaagactatc | tgtatcaaga | agagcttgaa | aacgcccaaa | gcgaaggcat cattacgctt | 2880 |
| cataccgctt | tttctcgcat | gccaaatcag | ccgaaaacat | acgttcagca cgtaatggaa | 2940 |
| caagacggca | agaaattgat | tgaacttctt | gatcaaggag | cgcacttcta tatttgcgga | 3000 |
| gacgaagcc | aaatgcacc | tgccgttgaa | gcaacgctta | tgaaaagcta tgctgacgtt | 3060 |
| caccaagtga | gtgaagcaga | cgctcgctta | tggctgcagc | agctagaaga aaaaggccga | 3120 |

-continued tacgcaaaag acgtgtgggc tggg                                         3144

<210> SEQ ID NO 38
<211> LENGTH: 1048
<212> TYPE: PRT
<213> ORGANISM: Bacillus megaterium

<400> SEQUENCE: 38

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Leu Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

```
Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
                530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
                740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
770                 775                 780
```

-continued

| | | | | | | | | | | | | | | |
|---|---|---|---|---|---|---|---|---|---|---|---|---|---|---|
|Glu|Lys|Gln|Ala|Tyr|Lys|Glu|Gln|Val|Leu|Ala|Lys|Arg|Leu|Thr|Met|
|785| | | | |790| | | | |795| | | | |800|

Leu Glu Leu Leu Glu Lys Tyr Pro Ala Cys Glu Met Lys Phe Ser Glu
805 810 815

Phe Ile Ala Leu Leu Pro Ser Ile Arg Pro Arg Tyr Tyr Ser Ile Ser
820 825 830

Ser Ser Pro Arg Val Asp Glu Lys Gln Ala Ser Ile Thr Val Ser Val
835 840 845

Val Ser Gly Glu Ala Trp Ser Gly Tyr Gly Tyr Lys Gly Ile Ala
850 855 860

Ser Asn Tyr Leu Ala Glu Leu Gln Gly Asp Thr Ile Thr Cys Phe
865 870 875 880

Ile Ser Thr Pro Gln Ser Glu Phe Thr Leu Pro Lys Asp Pro Glu Thr
885 890 895

Pro Leu Ile Met Val Gly Pro Gly Thr Gly Val Ala Pro Phe Arg Gly
900 905 910

Phe Val Gln Ala Arg Lys Gln Leu Lys Glu Gln Gly Gln Ser Leu Gly
915 920 925

Glu Ala His Leu Tyr Phe Gly Cys Arg Ser Pro His Glu Asp Tyr Leu
930 935 940

Tyr Gln Glu Glu Leu Glu Asn Ala Gln Ser Glu Gly Ile Ile Thr Leu
945 950 955 960

His Thr Ala Phe Ser Arg Met Pro Asn Gln Pro Lys Thr Tyr Val Gln
965 970 975

His Val Met Glu Gln Asp Gly Lys Lys Leu Ile Glu Leu Leu Asp Gln
980 985 990

Gly Ala His Phe Tyr Ile Cys Gly Asp Gly Ser Gln Met Ala Pro Ala
995 1000 1005

Val Glu Ala Thr Leu Met Lys Ser Tyr Ala Asp Val His Gln Val Ser
1010 1015 1020

Glu Ala Asp Ala Arg Leu Trp Leu Gln Gln Leu Glu Glu Lys Gly Arg
1025 1030 1035 1040

Tyr Ala Lys Asp Val Trp Ala Gly
1045

<210> SEQ ID NO 39
<211> LENGTH: 3144
<212> TYPE: DNA
<213> ORGANISM: Bacillus megaterium

<400> SEQUENCE: 39

```
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgcttaaatt tgcacgtgat     240
tttgcaggag acgggttagt gacaagctgg acgcatgaaa taaattggaa aaaagcgcat     300
aatatcttac ttccaagctt tagtcagcag gcaatgaaag gctatcatgc gatgatggtc     360
gatatcgccg tgcagcttgt tcaaaagtgg gagcgtctaa atgcagatga gcatattgaa     420
gtatcggaag acatgacacg tttaacgctt gataacaattg gtctttgcgg ctttaactat     480
cgctttaaca gcttttaccg agatcagcct catccattta ttataagtat ggtccgtgca     540
ctggatgaag taatgaacaa gctgcagcga gcaaatccag acgacccagc ttatgatgaa     600
```

```
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattaca    780
ttcttaattg cgggacacga aacaacaagt ggtcttttat catttgcgct gtatttctta    840
gtgaaaaatc cacatgtatt acaaaaagta gcagaagaag cagcacgagt tctagtagat    900
cctgttccaa gctacaaaca agtcaaacag cttaaatatg tcggcatggt cttaaacgaa    960
gcgctgcgct tatggccaac tgctcctgcg ttttccctat atgcaaaaga agatacggtg   1020
cttggaggag aatatccttt agaaaaaggc gacgaagtaa tggttctgat tcctcagctt   1080
caccgtgata aaacaatttg gggagacgat gtggaggagt tccgtccaga gcgttttgaa   1140
aatccaagtg cgattccgca gcatgcgttt aaaccgtttg gaaacggtca gcgtgcgtgt   1200
atcggtcagc agttcgctct tcatgaagca acgctggtac ttggtatgat gctaaaacac   1260
tttgactttg aagatcatac aaactacgag ctcgatatta agaaactttt aacgttaaaa   1320
cctgaaggct ttgtggtaaa agcaaaatcg aaaaaaattc cgcttggcgg tattccttca   1380
cctagcactg aacagtctgc taaaaaagta cgcaaaaagg cagaaaacgc tcataatacg   1440
ccgctgcttg tgctatacgg ttcaaatatg gaacagctg aaggaacggc gcgtgattta    1500
gcagatattg caatgagcaa aggatttgca ccgcaggtcg caacgcttga ttcacacgcc   1560
ggaaatcttc cgcgcgaagg agctgtatta attgtaacgg cgtcttataa cggtcatccg   1620
cctgataacg caaagcaatt tgtcgactgg ttagaccaag cgtctgctga tgaagtaaaa   1680
ggcgttcgct actccgtatt tggatgcggc gataaaaact gggctactac gtatcaaaaa   1740
gtgcctgctt ttatcgatga aacgcttgcc gctaaagggg cagaaaacat cgctgaccgc   1800
ggtgaagcag atgcaagcga cgactttgaa ggcacatatg aagaatggcg tgaacatatg   1860
tggagtgacg tagcagccta ctttaacctc gacattgaaa acagtgaaga taataaatct   1920
actctttcac ttcaatttgt cgacagcgcc gcggatatgc cgcttgcgaa aatgcacggt   1980
gcgttttcaa cgaacgtcgt agcaagcaaa gaacttcaac agccaggcag tgcacgaagc   2040
acgcgacatc ttgaaattga acttccaaaa gaagcttctt atcaagaagg agatcattta   2100
ggtgttattc ctcgcaacta tgaaggaata gtaaaccgtg taacagcaag gttcggccta   2160
gatgcatcac agcaaatccg tctggaagca gaagaagaaa aattagctca tttgccactc   2220
gctaaaacag tatccgtaga agagcttctg caatacgtgg agcttcaaga tcctgttacg   2280
cgcacgcagc ttcgcgcaat ggctgctaaa acggtctgcc cgccgcataa agtagagctt   2340
gaagccttgc ttgaaaagca agcctacaaa gaacaagtgc tggcaaaacg tttaacaatg   2400
cttgaactgc ttgaaaaata cccggcgtgt gaaatgaaat tcagcgaatt tatcgcccct   2460
ctgccaagca tacgcccgcg ctattactcg atttcttcat cacctcgtgt cgatgaaaaa   2520
caagcaagca tcacggtcag cgttgtctca ggagaagcgt ggagcggata tggagaatat   2580
aaaggaattg cgtcgaacta tcttgccgag ctgcaagaag gagatacgat tacgtgcttt   2640
atttccacac cgcagtcaga atttacgctg ccaaaagacc ctgaaacgcc gcttatcatg   2700
gtcggaccgg gaacaggcgt cgcgccgttt agaggctttg tgcaggcgcg caaacagcta   2760
aaagaacaag gacagtcact tggagaagca catttatact tcggctgccg ttcacctcat   2820
gaagactatc tgtatcaaga agagcttgaa aacgcccaaa gcgaaggcat cattacgctt   2880
cataccgctt tttctcgcat gccaaatcag ccgaaaacat acgttcagca cgtaatggaa   2940
caagacggca agaaattgat tgaacttctt gatcaaggag cgcacttcta tatttgcgga   3000
```

-continued

```
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 40
<211> LENGTH: 1048
<212> TYPE: PRT
<213> ORGANISM: Bacillus megaterium

<400> SEQUENCE: 40

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
 65                  70                  75                  80

Phe Ala Gly Asp Gly Leu Val Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
```

-continued

```
                340                 345                 350
Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
        450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765
```

Ala Lys Thr Val Cys Pro Pro His Lys Val Glu Leu Glu Ala Leu Leu
        770             775                 780
Glu Lys Gln Ala Tyr Lys Glu Gln Val Leu Ala Lys Arg Leu Thr Met
785             790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
            820                 825                 830
Ser Ser Pro Arg Val Asp Glu Lys Gln Ala Ser Ile Thr Val Ser Val
        835                 840                 845
Val Ser Gly Glu Ala Trp Ser Gly Tyr Gly Glu Tyr Lys Gly Ile Ala
850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
            900                 905                 910
Phe Val Gln Ala Arg Lys Gln Leu Lys Glu Gln Gly Gln Ser Leu Gly
        915                 920                 925
Glu Ala His Leu Tyr Phe Gly Cys Arg Ser Pro His Glu Asp Tyr Leu
    930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
        995                 1000                1005
Val Glu Ala Thr Leu Met Lys Ser Tyr Ala Asp Val His Gln Val Ser
    1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
                1045

<210> SEQ ID NO 41
<211> LENGTH: 3144
<212> TYPE: DNA
<213> ORGANISM: Bacillus megaterium

<400> SEQUENCE: 41
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgattaaatt tgcacgtgat     240
tttgcaggag acgggttatt tacaagctgg acgcatgaaa taaattggaa aaaagcgcat     300
aatatcttac ttccaagctt tagtcagcag gcaatgaaag ctatcatgc gatgatggtc     360 gatatcgccg tgcagcttgt tcaaaagtgg gagcgtctaa atgcagatga gcatattgaa     420
gtatcggaag acatgacacg tttaacgctt gatacaattg gtctttgcgg ctttaactat     480

```
cgctttaaca gcttttaccg agatcagcct catccattta ttataagtat ggtccgtgca      540
ctggatgaag taatgaacaa gctgcagcga gcaaatccag acgacccagc ttatgatgaa      600
aacaagcgcc agtgtcaaga agatatcaag gtgatgaacg acctagtaga taaaattatt      660
gcagatcgca aagcaagggg tgaacaaagc gatgatttat taacgcagat gctaaacgga      720
aaagatccag aaacgggtga gccgcttgat gacgggaaca ttagctatca aattattaca      780
ttcttaattg cgggacacga aacaacaagt ggtctttat catttgcgct gtatttctta      840
gtgaaaaatc cacatgtatt acaaaaagta gcagaagaag cagcacgagt tctagtagat      900
cctgttccaa gctacaaaca agtcaaacag cttaaatatg tcggcatggt cttaaacgaa      960
gcgctgcgct tatggccaac tgctcctgcg ttttccctat atgcaaaaga agatacggtg     1020
cttggaggag aatatccttt agaaaaaggc gacgaagtaa tggttctgat tcctcagctt     1080
caccgtgata aaacaatttg gggagacgat gtggaggagt tccgtccaga gcgttttgaa     1140
aatccaagtg cgattccgca gcatgcgttt aaaccgtttg gaaacggtca gcgtgcgtgt     1200
atcggtcagc agttcgctct tcatgaagca acgctggtac ttggtatgat gctaaaacac     1260
tttgactttg aagatcatac aaactacgag ctcgatatta agaaacttt aacgttaaaa     1320 cctgaaggct ttgtggtaaa agcaaaatcg aaaaaaattc cgcttggcgg tattccttca     1380
cctagcactg aacagtctgc taaaaaagta cgcaaaaagg cagaaaacgc tcataatacg     1440
ccgctgcttg tgctatacgg ttcaaatatg ggaacagctg aaggaacggc gcgtgattta     1500
gcagatattg caatgagcaa aggatttgca ccgcaggtcg caacgcttga ttcacacgcc     1560
ggaaatcttc cgcgcgaagg agctgtatta attgtaacgg cgtcttataa cggtcatccg     1620
cctgataacg caaagcaatt tgtcgactgg ttagaccaag cgtctgctga tgaagtaaaa     1680
ggcgttcgct actccgtatt tggatgcggc gataaaaact gggctactac gtatcaaaaa     1740
gtgcctgctt ttatcgatga aacgcttgcc gctaaagggg cagaaaacat cgctgaccgc     1800
ggtgaagcag atgcaagcga cgactttgaa ggcacatatg aagaatggcg tgaacatatg     1860
tggagtgacg tagcagccta ctttaacctc gacattgaaa acagtgaaga taataaatct     1920
actctttcac ttcaatttgt cgacagcgcc gcggatatgc cgcttgcgaa aatgcacggt     1980 gcgtttttcaa cgaacgtcgt agcaagcaaa gaacttcaac agccaggcag tgcacgaagc     2040
acgcgacatc ttgaaattga acttccaaaa gaagcttctt atcaagaagg agatcattta     2100
ggtgttattc ctcgcaacta tgaaggaata gtaaaccgtg taacagcaag gttcggccta     2160
gatgcatcac agcaaatccg tctggaagca gaagaagaaa aattagctca tttgccactc     2220
gctaaaacag tatccgtaga agagcttctg caatacgtgg agcttcaaga tcctgttacg     2280
cgcacgcagc ttcgcgcaat ggctgctaaa acggtctgcc cgccgcataa agtagagctt     2340
gaagccttgc ttgaaaagca agcctacaaa gaacaagtgc tggcaaaacg tttaacaatg     2400
cttgaactgc ttgaaaaata cccggcgtgt gaaatgaaat tcagcgaatt tatcgcccct     2460
ctgccaagca tacgcccgcg ctattactcg atttcttcat cacctcgtgt cgatgaaaaa     2520
caagcaagca tcacggtcag cgttgtctca ggagaagcgt ggagcggata tggagaatat     2580
aaaggaattg cgtcgaacta tcttgccgag ctgcaagaag gagatacgat tacgtgcttt     2640
atttccacac cgcagtcaga atttacgctg ccaaaagacc ctgaaacgcc gcttatcatg     2700
gtcggaccgg gaacaggcgt cgcgccgttt agaggctttg tgcaggcgcg caaacagcta     2760
aaagaacaag gacagtcact tggagaagca catttatact tcggctgccg ttcacctcat     2820
gaagactatc tgtatcaaga agagcttgaa aacgcccaaa gcgaaggcat cattacgctt     2880
```

```
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144

<210> SEQ ID NO 42
<211> LENGTH: 1048
<212> TYPE: PRT
<213> ORGANISM: Bacillus megaterium

<400> SEQUENCE: 42

Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
                 20                  25                  30

Ala Asp Glu Leu Gly Glu Ile Phe Lys Phe Glu Ala Pro Gly Cys Val
             35                  40                  45

Thr Arg Tyr Leu Ser Ser Gln Arg Leu Ile Lys Glu Ala Cys Asp Glu
         50                  55                  60

Ser Arg Phe Asp Lys Asn Leu Ser Gln Ala Ile Lys Phe Ala Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320
```

```
Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
            370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
            610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
```

```
                     740                 745                 750
Val Glu Leu Gln Asp Pro Val Thr Arg Thr Gln Leu Arg Ala Met Ala
                755                 760                 765

Ala Lys Thr Val Cys Pro Pro His Lys Val Glu Leu Glu Ala Leu Leu
            770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
        850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
        930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 43
<211> LENGTH: 3144
<212> TYPE: DNA
<213> ORGANISM: Bacillus megaterium

<400> SEQUENCE: 43
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgtggaaatt tgcacgtgat     240
tttgcaggag acgggttatt tacaagctgg acgcatgaaa taaattggaa aaaagcgcat     300
aatatcttac ttccaagctt tagtcagcag gcaatgaaag gctatcatgc gatgatggtc     360
```

```
gatatcgccg tgcagcttgt tcaaaagtgg gagcgtctaa atgcagatga gcatattgaa    420
gtatcggaag acatgacacg tttaacgctt gatacaattg gtctttgcgg ctttaactat    480
cgctttaaca gcttttaccg agatcagcct catccattta ttataagtat ggtccgtgca    540
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattaca    780
ttcttaattg cgggacacga aacaacaagt ggtcttttat catttgcgct gtatttctta    840
gtgaaaaatc cacatgtatt acaaaaagta gcagaagaag cagcacgagt tctagtagat    900
cctgttccaa gctacaaaca agtcaaacag cttaaatatg tcggcatggt cttaaacgaa    960
gcgctgcgct tatggccaac tgctcctgcg ttttccctat atgcaaaaga agatacggtg   1020
cttggaggag aatatccttt agaaaaaggc gacgaagtaa tggttctgat tcctcagctt   1080
caccgtgata aaacaatttg gggagacgat gtggaggagt tccgtccaga gcgttttgaa   1140
aatccaagtg cgattccgca gcatgcgttt aaaccgtttg gaaacggtca gcgtgcgtgt   1200
atcggtcagc agttcgctct tcatgaagca acgctggtac ttggtatgat gctaaaacac   1260
tttgactttg aagatcatac aaactacgag ctcgatatta agaaactttt aacgttaaaa   1320
cctgaaggct ttgtggtaaa agcaaaatcg aaaaaaattc cgcttggcgg tattccttca   1380
cctagcactg aacagtctgc taaaaaagta cgcaaaaagg cagaaaacgc tcataatacg   1440
ccgctgcttg tgctatacgg ttcaaatatg ggaacagctg aaggaacggc gcgtgattta   1500
gcagatattg caatgagcaa aggatttgca ccgcaggtcg caacgcttga ttcacacgcc   1560
ggaaatcttc cgcgcgaagg agctgtatta attgtaacgg cgtcttataa cggtcatccg   1620
cctgataacg caaagcaatt tgtcgactgg ttagaccaag cgtctgctga tgaagtaaaa   1680
ggcgttcgct actccgtatt tggatgcggc gataaaaact gggctactac gtatcaaaaa   1740
gtgcctgctt ttatcgatga aacgcttgcc gctaaagggg cagaaaacat cgctgaccgc   1800
ggtgaagcag atgcaagcga cgactttgaa ggcacatatg aagaatggcg tgaacatatg   1860
tggagtgacg tagcagccta ctttaacctc gacattgaaa acagtgaaga taataaatct   1920
actctttcac ttcaatttgt cgacagcgcc gcggatatgc cgcttgcgaa aatgcacggt   1980
gcgttttcaa cgaacgtcgt agcaagcaaa gaacttcaac agccaggcag tgcacgaagc   2040
acgcgacatc ttgaaattga acttccaaaa gaagcttctt atcaagaagg agatcattta   2100
ggtgttattc ctcgcaacta tgaaggaata gtaaaccgtg taacagcaag gttcggccta   2160
gatgcatcac agcaaatccg tctggaagca gaagaagaaa aattagctca tttgccactc   2220
gctaaaacag tatccgtaga agagcttctg caatacgtgg agcttcaaga tcctgttacg   2280
cgcacgcagc ttcgcgcaat ggctgctaaa acggtctgcc cgccgcataa agtagagctt   2340
gaagccttgc ttgaaaagca agcctacaaa gaacaagtgc tggcaaaacg tttaacaatg   2400
cttgaactgc ttgaaaaata cccggcgtgt gaaatgaaat tcagcgaatt tatcgcctt    2460
ctgccaagca tacgcccgcg ctattactcg atttcttcat cacctcgtgt cgatgaaaaa   2520
caagcaagca tcacggtcag cgttgtctca ggagaagcgt ggagcggata tggagaatat   2580
aaaggaattg cgtcgaacta tcttgccgag ctgcaagaag gagatacgat tacgtgcttt   2640
atttccacac cgcagtcaga atttacgctg ccaaaagacc ctgaaacgcc gcttatcatg   2700
gtcggaccgg gaacaggcgt cgcgccgttt agaggctttg tgcaggcgcg caaacagcta   2760
```

-continued

```
aaagaacaag gacagtcact tggagaagca catttatact tcggctgccg ttcacctcat    2820
gaagactatc tgtatcaaga agagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 44
<211> LENGTH: 1048
<212> TYPE: PRT
<213> ORGANISM: Bacillus megaterium

<400> SEQUENCE: 44

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Trp Lys Phe Ala Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
    290                 295                 300
```

```
Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
            450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720
```

-continued

```
Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
        740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                 1000                1005

Val Glu Ala Thr Leu Met Lys Ser Tyr Ala Asp Val His Gln Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045
```

<210> SEQ ID NO 45
<211> LENGTH: 3144
<212> TYPE: DNA
<213> ORGANISM: Bacillus megaterium

<400> SEQUENCE: 45

| | | |
|---|---|---|
| acaattaaag aaatgcctca gccaaaaacg tttggagagc ttaaaaattt accgttatta | 60 |
| aacacagata aaccggttca agctttgatg aaaattgcgg atgaattagg agaaatcttt | 120 |
| aaattcgagg cgcctggttg tgtaacgcgc tacttatcaa gtcagcgtct aattaaagaa | 180 |
| gcatgcgatg aatcacgctt tgataaaaac ttaagtcaag cgcttaaatt tgcacgtgat | 240 |

```
tttgcaggag acgggttatt tacaagctgg acgcatgaaa taaattggaa aaaagcgcat    300
aatatcttac ttccaagctt tagtcagcag gcaatgaaag gctatcatgc gatgatggtc    360
gatatcgccg tgcagcttgt tcaaaagtgg gagcgtctaa atgcagatga gcatattgaa    420
gtatcggaag acatgacacg tttaacgctt gatacaattg gtctttgcgg ctttaactat    480
cgctttaaca gcttttaccg agatcagcct catccattta ttataagtat ggtccgtgca    540
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattctc    780
ttcttaattg cgggacacga aacaacaagt ggtcttttat catttgcgct gtatttctta    840
gtgaaaaatc cacatgtatt acaaaaagta gcagaagaag cagcacgagt tctagtagat    900
cctgttccaa gctacaaaca agtcaaacag cttaaatatg tcggcatggt cttaaacgaa    960
gcgctgcgct tatggccaac tgctcctgcg ttttccctat atgcaaaaga agatacggtg   1020
cttggaggag aatatccttt agaaaaaggc gacgaagtaa tggttctgat tcctcagctt   1080
caccgtgata aaacaatttg gggagacgat gtggaggagt tccgtccaga gcgttttgaa   1140
aatccaagtg cgattccgca gcatgcgttt aaaccgtttg gaaacggtca gcgtgcgtgt   1200
atcggtcagc agttcgctct tcatgaagca acgctggtac ttggtatgat gctaaaacac   1260
tttgactttg aagatcatac aaactacgag ctcgatatta agaaacttt aacgttaaaa   1320 cctgaaggct ttgtggtaaa agcaaaatcg aaaaaaattc cgcttggcgg tattccttca   1380
cctagcactg aacagtctgc taaaaaagta cgcaaaaagg cagaaaacgc tcataatacg   1440
ccgctgcttg tgctatacgg ttcaaatatg gaacagctg aaggaacggc gcgtgattta   1500
gcagatattg caatgagcaa aggatttgca ccgcaggtcg caacgcttga ttcacacgcc   1560
ggaaatcttc cgcgcgaagg agctgtatta attgtaacgg cgtcttataa cggtcatccg   1620
cctgataacg caaagcaatt tgtcgactgg ttagaccaag cgtctgctga tgaagtaaaa   1680
ggcgttcgct actccgtatt tggatgcggc gataaaaact gggctactac gtatcaaaaa   1740
gtgcctgctt ttatcgatga aacgcttgcc gctaaagggg cagaaaacat cgctgaccgc   1800
ggtgaagcag atgcaagcga cgactttgaa ggcacatatg aagaatggcg tgaacatatg   1860
tggagtgacg tagcagccta ctttaacctc gacattgaaa acagtgaaga taataaatct   1920
actctttcac ttcaatttgt cgacagcgcc gcggatatgc cgcttgcgaa aatgcacggt   1980
gcgttttcaa cgaacgtcgt agcaagcaaa gaacttcaac agccaggcag tgcacgaagc   2040
acgcgacatc ttgaaattga acttccaaaa gaagcttctt atcaagaagg agatcattta   2100
ggtgttattc ctcgcaacta tgaaggaata gtaaaccgtg taacagcaag gttcggccta   2160
gatgcatcac agcaaatccg tctggaagca gaagaagaaa aattagctca tttgccactc   2220
gctaaaacag tatccgtaga agagcttctg caatacgtgg agcttcaaga tcctgttacg   2280
cgcacgcagc ttcgcgcaat ggctgctaaa acggtctgcc cgccgcataa agtagagctt   2340
gaagccttgc ttgaaaagca agcctacaaa gaacaagtgc tggcaaaacg tttaacaatg   2400
cttgaactgc ttgaaaaata cccggcgtgt gaaatgaaat tcagcgaatt tatcgcccctt   2460 ctgccaagca tacgcccgcg ctattactcg atttcttcat cacctcgtgt cgatgaaaaa   2520
caagcaagca tcacggtcag cgttgtctca ggagaagcgt ggagcggata tggagaatat   2580
aaaggaattg cgtcgaacta tcttgccgag ctgcaagaag gagatacgat tacgtgcttt   2640
```

-continued

```
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga gagcttgaa acgcccaaa gcgaaggcat cattacgctt     2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                          3144
```

<210> SEQ ID NO 46
<211> LENGTH: 1048
<212> TYPE: PRT
<213> ORGANISM: Bacillus megaterium

<400> SEQUENCE: 46

```
Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Phe Thr Ser Trp Thr His Glu Ile Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Leu Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
```

-continued

```
                275                 280                 285
Lys Val Ala Glu Glu Ala Arg Val Leu Val Asp Pro Val Pro Ser
    290                 295                 300
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Val Met Val Leu Ile Pro Gln Leu His Arg Asp Lys Thr Ile Trp Gly
            355                 360                 365
Asp Asp Val Glu Glu Phe Arg Pro Glu Arg Phe Glu Asn Pro Ser Ala
    370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
            435                 440                 445
Lys Ser Lys Lys Ile Pro Leu Gly Gly Ile Pro Ser Pro Ser Thr Glu
    450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
            515                 520                 525
Val Leu Ile Val Thr Ala Ser Tyr Asn Gly His Pro Pro Asp Asn Ala
            530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
            595                 600                 605
Phe Glu Gly Thr Tyr Glu Glu Trp Arg Glu His Met Trp Ser Asp Val
    610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Asp Met Pro Leu Ala
                645                 650                 655
Lys Met His Gly Ala Phe Ser Thr Asn Val Val Ala Ser Lys Glu Leu
            660                 665                 670
Gln Gln Pro Gly Ser Ala Arg Ser Thr Arg His Leu Glu Ile Glu Leu
            675                 680                 685
Pro Lys Glu Ala Ser Tyr Gln Glu Gly Asp His Leu Gly Val Ile Pro
    690                 695                 700
```

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
    995                 1000                1005

Val Glu Ala Thr Leu Met Lys Ser Tyr Ala Asp Val His Gln Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 47
<211> LENGTH: 3144
<212> TYPE: DNA
<213> ORGANISM: Bacillus megaterium

<400> SEQUENCE: 47
acaattaaag aaatgcctca gccaaaaacg tttggagagc ttaaaaattt accgttatta      60
aacacagata aaccggttca agctttgatg aaaattgcgg atgaattagg agaaatcttt     120

```
aaattcgagg cgcctggttg tgtaacgcgc tacttatcaa gtcagcgtct aattaaagaa    180
gcatgcgatg aatcacgctt tgataaaaac ttaagtcaag cgcttaaatt tgcacgtgat    240
tttgcaggag acgggttatt tacaagctgg acgcatgaaa taaattggaa aaaagcgcat    300
aatatcttac ttccaagctt tagtcagcag gcaatgaaag gctatcatgc gatgatggtc    360
gatatcgccg tgcagcttgt tcaaaagtgg gagcgtctaa atgcagatga gcatattgaa    420
gtatcggaag acatgacacg tttaacgctt gatacaattg gtcttttgcg ctttaactat    480
cgctttaaca gcttttaccg agatcagcct catccattta ttataagtat ggtccgtgca    540
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattaac    780
ttcttaattg cgggacacga aacaacaagt ggtcttttat catttgcgct gtatttctta    840
gtgaaaaatc cacatgtatt acaaaaagta gcagaagaag cagcacgagt tctagtagat    900
cctgttccaa gctacaaaca agtcaaacag cttaaatatg tcggcatggt cttaaacgaa    960
gcgctgcgct tatggccaac tgctcctgcg tttccctat atgcaaaaga agatacggtg   1020
cttggaggag aatatccttt agaaaaaggc gacgaagtaa tggttctgat tcctcagctt   1080
caccgtgata aacaatttg gggagacgat gtggaggagt tccgtccaga gcgttttgaa   1140
aatccaagtg cgattccgca gcatgcgttt aaaccgtttg gaaacggtca gcgtgcgtgt   1200
atcggtcagc agttcgctct tcatgaagca acgctggtac ttggtatgat gctaaaacac   1260
tttgactttg aagatcatac aaactacgag ctcgatatta aagaaacttt aacgttaaaa   1320
cctgaaggct ttgtggtaaa agcaaaatcg aaaaaaattc cgcttggcgg tattccttca   1380
cctagcactg aacagtctgc taaaaaagta cgcaaaaagg cagaaaacgc tcataatacg   1440
ccgctgcttg tgctatacgg ttcaaatatg gaacagctg aaggaacggc gcgtgattta   1500
gcagatattg caatgagcaa aggatttgca ccgcaggtcg caacgcttga ttcacacgcc   1560
ggaaatcttc cgcgcgaagg agctgtatta attgtaacgg cgtcttataa cggtcatccg   1620
cctgataacg caaagcaatt tgtcgactgg ttagaccaag cgtctgctga tgaagtaaaa   1680
ggcgttcgct actccgtatt tggatgcggc gataaaaact gggctactac gtatcaaaaa   1740
gtgcctgctt ttatcgatga aacgcttgcc gctaaagggg cagaaaacat cgctgaccgc   1800
ggtgaagcag atgcaagcga cgactttgaa ggcacatatg aagaatggcg tgaacatatg   1860
tggagtgacg tagcagccta ctttaacctc gacattgaaa acagtgaaga taataaatct   1920
actctttcac ttcaatttgt cgacagcgcc gcggatatgc cgcttgcgaa aatgcacggt   1980
gcgttttcaa cgaacgtcgt agcaagcaaa gaacttcaac agccaggcag tgcacgaagc   2040
acgcgacatc ttgaaattga acttccaaaa gaagcttctt atcaagaagg agatcattta   2100
ggtgttattc ctcgcaacta tgaaggaata gtaaaccgtg taacagcaag gttcggccta   2160
gatgcatcac agcaaatccg tctggaagca gaagaagaaa aattagctca tttgccactc   2220
gctaaaacag tatccgtaga agagcttctg caatacgtgg agcttcaaga tcctgttacg   2280
cgcacgcagc ttcgcgcaat ggctgctaaa acgtctgcc cgccgcataa agtagagctt   2340
gaagccttgc ttgaaaagca agcctacaaa gaacaagtgc tggcaaaacg tttaacaatg   2400
cttgaactgt tgaaaaaata cccggcgtgt gaaatgaaat tcagcgaatt tatcgcccttt  2460
ctgccaagca tacgcccgcg ctattactcg atttcttcat cacctcgtgt cgatgaaaaa   2520
```

-continued

```
caagcaagca tcacggtcag cgttgtctca ggagaagcgt ggagcggata tggagaatat   2580
aaaggaattg cgtcgaacta tcttgccgag ctgcaagaag gagatacgat tacgtgcttt   2640
atttccacac cgcagtcaga atttacgctg ccaaaagacc ctgaaacgcc gcttatcatg   2700
gtcggaccgg gaacaggcgt cgcgccgttt agaggctttg tgcaggcgcg caaacagcta   2760
aaagaacaag gacagtcact tggagaagca catttatact tcggctgccg ttcacctcat   2820
gaagactatc tgtatcaaga gagcttgaa aacgcccaaa gcgaaggcat cattacgctt   2880
cataccgctt tttctcgcat gccaaatcag ccgaaaacat acgttcagca cgtaatggaa   2940
caagacggca agaaattgat tgaacttctt gatcaaggag cgcacttcta tatttgcgga   3000
gacggaagcc aaatggcacc tgccgttgaa gcaacgctta tgaaaagcta tgctgacgtt   3060
caccaagtga gtgaagcaga cgctcgctta tggctgcagc agctagaaga aaaaggccga   3120
tacgcaaaag acgtgtgggc tggg                                          3144
```

<210> SEQ ID NO 48
<211> LENGTH: 1048
<212> TYPE: PRT
<213> ORGANISM: Bacillus megaterium

<400> SEQUENCE: 48

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255
```

```
Gln Ile Ile Asn Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
            275                 280                 285

Lys Val Ala Glu Ala Ala Arg Val Leu Val Asp Pro Val Pro Ser
        290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
```

-continued

|  |  |  |  | 675 |  |  |  |  | 680 |  |  |  |  | 685 |
|---|---|---|---|---|---|---|---|---|---|---|---|---|---|---|

Pro Lys Glu Ala Ser Tyr Gln Glu Gly Asp His Leu Gly Val Ile Pro
690                     695                     700

Arg Asn Tyr Glu Gly Ile Val Asn Arg Val Thr Ala Arg Phe Gly Leu
705                     710                     715                     720

Asp Ala Ser Gln Gln Ile Arg Leu Glu Ala Glu Glu Lys Leu Ala
            725                     730                     735

His Leu Pro Leu Ala Lys Thr Val Ser Val Glu Leu Leu Gln Tyr
            740                     745                     750

Val Glu Leu Gln Asp Pro Val Thr Arg Thr Gln Leu Arg Ala Met Ala
            755                     760                     765

Ala Lys Thr Val Cys Pro Pro His Lys Val Glu Leu Glu Ala Leu Leu
770                     775                     780

Glu Lys Gln Ala Tyr Lys Glu Gln Val Leu Ala Lys Arg Leu Thr Met
785                     790                     795                     800

Leu Glu Leu Leu Glu Lys Tyr Pro Ala Cys Glu Met Lys Phe Ser Glu
            805                     810                     815

Phe Ile Ala Leu Leu Pro Ser Ile Arg Pro Arg Tyr Tyr Ser Ile Ser
            820                     825                     830

Ser Ser Pro Arg Val Asp Glu Lys Gln Ala Ser Ile Thr Val Ser Val
            835                     840                     845

Val Ser Gly Glu Ala Trp Ser Gly Tyr Gly Glu Tyr Lys Gly Ile Ala
850                     855                     860

Ser Asn Tyr Leu Ala Glu Leu Gln Glu Gly Asp Thr Ile Thr Cys Phe
865                     870                     875                     880

Ile Ser Thr Pro Gln Ser Glu Phe Thr Leu Pro Lys Asp Pro Glu Thr
            885                     890                     895

Pro Leu Ile Met Val Gly Pro Gly Thr Gly Val Ala Pro Phe Arg Gly
            900                     905                     910

Phe Val Gln Ala Arg Lys Gln Leu Lys Glu Gln Gly Gln Ser Leu Gly
            915                     920                     925

Glu Ala His Leu Tyr Phe Gly Cys Arg Ser Pro His Glu Asp Tyr Leu
930                     935                     940

Tyr Gln Glu Glu Leu Glu Asn Ala Gln Ser Glu Gly Ile Ile Thr Leu
945                     950                     955                     960

His Thr Ala Phe Ser Arg Met Pro Asn Gln Pro Lys Thr Tyr Val Gln
            965                     970                     975

His Val Met Glu Gln Asp Gly Lys Lys Leu Ile Glu Leu Leu Asp Gln
            980                     985                     990

Gly Ala His Phe Tyr Ile Cys Gly Asp Gly Ser Gln Met Ala Pro Ala
            995                     1000                    1005

Val Glu Ala Thr Leu Met Lys Ser Tyr Ala Asp Val His Gln Val Ser
            1010                    1015                    1020

Glu Ala Asp Ala Arg Leu Trp Leu Gln Gln Leu Glu Glu Lys Gly Arg
1025                    1030                    1035                    1040

Tyr Ala Lys Asp Val Trp Ala Gly
            1045

<210> SEQ ID NO 49
<211> LENGTH: 3144
<212> TYPE: DNA
<213> ORGANISM: Bacillus megaterium

<400> SEQUENCE: 49

```
acaattaaag aaatgcctca gccaaaaacg tttggagagc ttaaaaattt accgttatta    60
aacacagata aaccggttca agctttgatg aaaattgcgg atgaattagg agaaatcttt   120
aaattcgagg cgcctggttg tgtaacgcgc tacttatcaa gtcagcgtct aattaaagaa   180
gcatgcgatg aatcacgctt tgataaaaac ttaagtcaag cgcttaaatt tgcacgtgat   240
tttgcaggag acgggttatt tacaagctgg acgcatgaaa taaattggaa aaaagcgcat   300
aatatcttac ttccaagctt tagtcagcag gcaatgaaag gctatcatgc gatgatggtc   360
gatatcgccg tgcagcttgt tcaaaagtgg gagcgtctaa atgcagatga gcatattgaa   420
gtatcggaag acatgacacg tttaacgctt gatacaattg gtctttgcgg ctttaactat   480
cgctttaaca gcttttaccg agatcagcct catccattta ttataagtat ggtccgtgca   540
ctggatgaag taatgaacaa gctgcagcga gcaaatccag acgacccagc ttatgatgaa   600
aacaagcgcc agtgtcaaga agatatcaag gtgatgaacg acctagtaga taaaattatt   660
gcagatcgca aagcaagggg tgaacaaagc gatgatttat aacgcagat gctaaacgga    720
aaagatccag aaacgggtga gccgcttgat gacgggaaca ttagctatca aattatttca   780
ttcttaattg cgggacacga aacaacaagt ggtcttttat catttgcgct gtatttctta   840
gtgaaaaatc cacatgtatt acaaaaagta gcagaagaag cagcacgagt tctagtagat   900
cctgttccaa gctacaaaca agtcaaacag cttaaatatg tcggcatggt cttaaacgaa   960
gcgctgcgct tatggccaac tgctcctgcg ttttccctat atgcaaaaga agatacggtg  1020
cttggaggag aatatccttt agaaaaaggc gacgaagtaa tggttctgat tcctcagctt  1080
caccgtgata aaacaatttg gggagacgat gtggaggagt tccgtccaga gcgttttgaa  1140
aatccaagtg cgattccgca gcatgcgttt aaaccgtttg gaaacggtca gcgtgcgtgt  1200
atcggtcagc agttcgctct tcatgaagca acgctggtac ttggtatgat gctaaaacac  1260
tttgactttg aagatcatac aaactacgag ctcgatatta agaaacttt aacgttaaaa   1320
cctgaaggct ttgtggtaaa agcaaaatcg aaaaaaattc cgcttggcgg tattccttca  1380
cctagcactg aacagtctgc taaaaaagta cgcaaaaagg cagaaaacgc tcataatacg  1440
ccgctgcttg tgctatacgg ttcaaatatg ggaacagctg aaggaacggc gcgtgattta  1500
gcagatattg caatgagcaa aggatttgca ccgcaggtcg caacgcttga ttcacacgcc  1560
ggaaatcttc cgcgcgaagg agctgtatta attgtaacgg cgtcttataa cggtcatccg  1620
cctgataacg caaagcaatt tgtcgactgg ttagaccaag cgtctgctga tgaagtaaaa  1680
ggcgttcgct actccgtatt tggatgcggc gataaaaact gggctactac gtatcaaaaa  1740
gtgcctgctt ttatcgatga aacgcttgcc gctaaagggg cagaaaacat cgctgaccgc  1800
ggtgaagcag atgcaagcga cgactttgaa ggcacatatg aagaatggcg tgaacatatg  1860
tggagtgacg tagcagccta ctttaacctc gacattgaaa acagtgaaga taataaatct  1920
actctttcac ttcaatttgt cgacagcgcc gcggatatgc cgcttgcgaa aatgcacggt  1980
gcgttttcaa cgaacgtcgt agcaagcaaa gaacttcaac agccaggcag tgcacgaagc  2040
acgcgacatc ttgaaattga acttccaaaa gaagcttctt atcaagaagg agatcattta  2100
ggtgttattc ctcgcaacta tgaaggaata gtaaaccgtg taacagcaag gttcggccta  2160
gatgcatcac agcaaatccg tctggaagca gaagaagaaa aattagctca tttgccactc  2220
gctaaaacag tatccgtaga agagcttctg caatacgtgg agcttcaaga tcctgttacg  2280
cgcacgcagc ttcgcgcaat ggctgctaaa acgtctgcc cgccgcataa agtgagcttt  2340
gaagccttgc ttgaaaagca agcctacaaa gaacaagtgc tggcaaaacg tttaacaatg  2400
```

-continued

```
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga gagcttgaa acgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                           3144
```

<210> SEQ ID NO 50
<211> LENGTH: 1048
<212> TYPE: PRT
<213> ORGANISM: Bacillus megaterium

<400> SEQUENCE: 50

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Cys Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
 65                  70                  75                  80

Phe Ala Gly Asp Gly Leu Phe Thr Ser Trp Thr His Glu Ile Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Ser Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190

Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
    210                 215                 220

Ala Arg Gly Glu Gln Ser Asp Asp Leu Leu Thr Gln Met Leu Asn Gly
225                 230                 235                 240
```

-continued

```
Lys Asp Pro Glu Thr Gly Glu Pro Leu Asp Asp Gly Asn Ile Ser Tyr
                245                 250                 255

Gln Ile Ile Ser Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Val Ala Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655
```

```
Lys Met His Gly Ala Phe Ser Thr Asn Val Ala Ser Lys Glu Leu
            660                 665                 670
Gln Gln Pro Gly Ser Ala Arg Ser Thr Arg His Leu Glu Ile Glu Leu
        675                 680                 685
Pro Lys Glu Ala Ser Tyr Gln Glu Gly Asp His Leu Gly Val Ile Pro
    690                 695                 700
Arg Asn Tyr Glu Gly Ile Val Asn Arg Val Thr Ala Arg Phe Gly Leu
705                 710                 715                 720
Asp Ala Ser Gln Gln Ile Arg Leu Glu Ala Glu Glu Lys Leu Ala
                725                 730                 735
His Leu Pro Leu Ala Lys Thr Val Ser Val Glu Leu Leu Gln Tyr
            740                 745                 750
Val Glu Leu Gln Asp Pro Val Thr Arg Thr Gln Leu Arg Ala Met Ala
        755                 760                 765
Ala Lys Thr Val Cys Pro Pro His Lys Val Glu Leu Glu Ala Leu Leu
    770                 775                 780
Glu Lys Gln Ala Tyr Lys Glu Gln Val Leu Ala Lys Arg Leu Thr Met
785                 790                 795                 800
Leu Glu Leu Leu Glu Lys Tyr Pro Ala Cys Glu Met Lys Phe Ser Glu
                805                 810                 815
Phe Ile Ala Leu Leu Pro Ser Ile Arg Pro Arg Tyr Tyr Ser Ile Ser
            820                 825                 830
Ser Ser Pro Arg Val Asp Glu Lys Gln Ala Ser Ile Thr Val Ser Val
        835                 840                 845
Val Ser Gly Glu Ala Trp Ser Gly Tyr Gly Glu Tyr Lys Gly Ile Ala
    850                 855                 860
Ser Asn Tyr Leu Ala Glu Leu Gln Glu Gly Asp Thr Ile Thr Cys Phe
865                 870                 875                 880
Ile Ser Thr Pro Gln Ser Glu Phe Thr Leu Pro Lys Asp Pro Glu Thr
                885                 890                 895
Pro Leu Ile Met Val Gly Pro Gly Thr Gly Val Ala Pro Phe Arg Gly
            900                 905                 910
Phe Val Gln Ala Arg Lys Gln Leu Lys Glu Gln Gly Gln Ser Leu Gly
        915                 920                 925
Glu Ala His Leu Tyr Phe Gly Cys Arg Ser Pro His Glu Asp Tyr Leu
    930                 935                 940
Tyr Gln Glu Glu Leu Glu Asn Ala Gln Ser Glu Gly Ile Ile Thr Leu
945                 950                 955                 960
His Thr Ala Phe Ser Arg Met Pro Asn Gln Pro Lys Thr Tyr Val Gln
                965                 970                 975
His Val Met Glu Gln Asp Gly Lys Lys Leu Ile Glu Leu Leu Asp Gln
            980                 985                 990
Gly Ala His Phe Tyr Ile Cys Gly Asp Gly Ser Gln Met Ala Pro Ala
        995                 1000                1005
Val Glu Ala Thr Leu Met Lys Ser Tyr Ala Asp Val His Gln Val Ser
    1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
                1045

<210> SEQ ID NO 51
<211> LENGTH: 3144
<212> TYPE: DNA
```

<213> ORGANISM: Bacillus megaterium

<400> SEQUENCE: 51

```
acaattaaag aaatgcctca gccaaaaacg tttggagagc ttaaaaattt accgttatta      60
aacacagata aaccggttca agctttgatg aaaattgcgg atgaattagg agaaatcttt     120
aaattcgagg cgcctggttg tgtaacgcgc tacttatcaa gtcagcgtct aattaaagaa     180
gcatgcgatg aatcacgctt tgataaaaac ttaagtcaag cgcttaaatt tgcacgtgat     240
tttgcaggag acgggttatt ttgtagctgg acgcatgaaa taaattggaa aaaagcgcat     300
aatatcttac ttccaagctt tagtcagcag gcaatgaaag gctatcatgc gatgatggtc     360
gatatcgccg tgcagcttgt tcaaaagtgg gagcgtctaa atgcagatga gcatattgaa     420
gtatcggaag acatgacacg tttaacgctt gataacaattg gtcttttgcgg ctttaactat     480
cgctttaaca gcttttaccg agatcagcct catccattta ttataagtat ggtccgtgca     540
ctggatgaag taatgaacaa gctgcagcga gcaaatccag acgacccagc ttatgatgaa     600
aacaagcgcc agtgtcaaga agatatcaag gtgatgaacg acctagtaga taaaattatt     660
gcagatcgca aagcaagggg tgaacaaagc gatgatttat taacgcagat gctaaacgga     720
aaagatccag aaacgggtga gccgcttgat gacgggaaca ttagctatca aattattaca     780
ttcttaattg cggacacgaa aacaacaagt ggtcttttat catttgcgct gtatttctta     840
gtgaaaaatc cacatgtatt acaaaaagta gcagaagaag cagcacgagt tctagtagat     900
cctgttccaa gctacaaaca agtcaaacag cttaaatatg tcggcatggt cttaaacgaa     960
gcgctgcgct tatggccaac tgctcctgcg ttttccctat atgcaaaaga agatacggtg    1020
cttggaggag aatatccttt agaaaaaggc gacgaagtaa tggttctgat tcctcagctt    1080
caccgtgata aaacaatttg gggagacgat gtggaggagt tccgtccaga gcgttttgaa    1140
aatccaagtg cgattccgca gcatgcgttt aaaccgtttg gaaacggtca gcgtgcgtgt    1200
atcggtcagc agttcgctct tcatgaagca acgctggtac ttggtatgat gctaaaacac    1260
tttgactttg aagatcatac aaactacgag ctcgatatta agaaactttt aacgttaaaa    1320
cctgaaggct tgtggtaaa agcaaaatcg aaaaaaattc cgcttggcgg tattccttca    1380
cctagcactg aacagtctgc taaaaaagta cgcaaaaagg cagaaaacgc tcataatacg    1440
ccgctgcttg tgctatacgg ttcaaatatg ggaacagctg aaggaacggc gcgtgattta    1500
gcagatattg caatgagcaa aggatttgca ccgcaggtcg caacgcttga ttcacacgcc    1560
ggaaatcttc cgcgcgaagg agctgtatta attgtaacgg cgtcttataa cggtcatccg    1620
cctgataacg caaagcaatt tgtcgactgg ttagaccaag cgtctgctga tgaagtaaaa    1680
ggcgttcgct actccgtatt tggatgcggc gataaaaact gggctactac gtatcaaaaa    1740
gtgcctgctt ttatcgatga aacgcttgcc gctaaagggg cagaaaacat cgctgaccgc    1800
ggtgaagcag atgcaagcga cgactttgaa ggcacatatg aagaatggcg tgaacatatg    1860
tggagtgacg tagcagccta ctttaacctc gacattgaaa acagtgaaga taataaatct    1920
actctttcac ttcaatttgt cgacagcgcc gcggatatgc cgcttgcgaa aatgcacggt    1980
gcgttttcaa cgaacgtcgt agcaagcaaa gaacttcaac agccaggcag tgcacgaagc    2040
acgcgacatc ttgaaattga acttccaaaa gaagcttctt atcaagaagg agatcattta    2100
ggtgttattc ctcgcaacta tgaaggaata gtaaaccgtg taacagcaag gttcggccta    2160
gatgcatcac agcaaatccg tctggaagca gaagaagaaa aattagctca tttgccactc    2220
gctaaaacag tatccgtaga agagcttctg caatacgtgg agcttcaaga tcctgttacg    2280
```

-continued

```
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga gagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                           3144
```

<210> SEQ ID NO 52
<211> LENGTH: 1048
<212> TYPE: PRT
<213> ORGANISM: Bacillus megaterium

<400> SEQUENCE: 52

```
Thr Ile Lys Glu Met Pro Gln Pro Lys Thr Phe Gly Glu Leu Lys Asn
 1               5                  10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Cys Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Ala Arg Asp
65                  70                  75                  80

Phe Ala Gly Asp Gly Leu Phe Cys Ser Trp Thr His Glu Ile Asn Trp
                85                  90                  95

Lys Lys Ala His Asn Ile Leu Leu Pro Ser Phe Ser Gln Gln Ala Met
           100                 105                 110

Lys Gly Tyr His Ala Met Met Val Asp Ile Ala Val Gln Leu Val Gln
       115                 120                 125

Lys Trp Glu Arg Leu Asn Ala Asp Glu His Ile Glu Val Ser Glu Asp
   130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
           180                 185                 190

Pro Asp Asp Pro Ala Tyr Asp Glu Asn Lys Arg Gln Cys Gln Glu Asp
       195                 200                 205

Ile Lys Val Met Asn Asp Leu Val Asp Lys Ile Ile Ala Asp Arg Lys
```

-continued

```
            210                 215                 220
Ala Arg Gly Glu Gln Ser Asp Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
                275                 280                 285

Lys Val Ala Glu Ala Ala Arg Val Leu Val Asp Pro Val Pro Ser
290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
                340                 345                 350

Val Met Val Leu Ile Pro Gln Leu His Arg Asp Lys Thr Ile Trp Gly
                355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
                435                 440                 445

Lys Ser Lys Lys Ile Pro Leu Gly Gly Ile Pro Ser Pro Ser Thr Glu
                450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
                500                 505                 510

Val Ala Thr Leu Asp Ser His Ala Gly Asn Leu Pro Arg Glu Gly Ala
                515                 520                 525

Val Leu Ile Val Thr Ala Ser Tyr Asn Gly His Pro Pro Asp Asn Ala
                530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
                580                 585                 590

Gly Ala Glu Asn Ile Ala Asp Arg Gly Glu Ala Asp Ala Ser Asp Asp
                595                 600                 605

Phe Glu Gly Thr Tyr Glu Glu Trp Arg Glu His Met Trp Ser Asp Val
                610                 615                 620

Ala Ala Tyr Phe Asn Leu Asp Ile Glu Asn Ser Glu Asp Asn Lys Ser
625                 630                 635                 640
```

```
Thr Leu Ser Leu Gln Phe Val Asp Ser Ala Asp Met Pro Leu Ala
            645                 650                 655

Lys Met His Gly Ala Phe Ser Thr Asn Val Val Ala Ser Lys Glu Leu
        660                 665                 670

Gln Gln Pro Gly Ser Ala Arg Ser Thr Arg His Leu Glu Ile Glu Leu
    675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Leu Leu Gln Tyr
            740                 745                 750

Val Glu Leu Gln Asp Pro Val Thr Arg Thr Gln Leu Arg Ala Met Ala
    755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
        980                 985                 990

Gly Ala His Phe Tyr Ile Cys Gly Asp Gly Ser Gln Met Ala Pro Ala
    995                 1000                1005

Val Glu Ala Thr Leu Met Lys Ser Tyr Ala Asp Val His Gln Val Ser
    1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045
```

<210> SEQ ID NO 53
<211> LENGTH: 3144
<212> TYPE: DNA
<213> ORGANISM: Bacillus megaterium

<400> SEQUENCE: 53

```
acaattaaag aaatgcctca gccaaaaacg tttggagagc ttaaaaattt accgttatta      60
aacacagata aaccggttca agctttgatg aaaattgcgg atgaattagg agaaatcttt    120
aaattcgagg cgcctggtcg tgtaacgcgc tacttatcaa gtcagcgtct aattaaagaa    180
gcatgcgatg aatcacgctt tgataaaaac ttaagtcaag cgcttaaatt tgcacgtgat    240
tttgcaggag acgggttatt tacaagctgg acgcatgaaa aaaattggaa aaaagcgcat    300
aatatcttac ttccaagctt tagtcagcag gcaatgaaag gctatcatgc gatgatggtc    360
gatatcgccg tgcagcttgt tcaaaagtgg gagcgtctaa atgcagatga gcatattgaa    420
gtaccggaag acatgacacg tttaacgctt gatacaattg gtctttgcgg ctttaactat    480
cgctttaaca gcttttaccg agatcagcct catccattta ttataagtat ggtccgtgca    540
ctggatgaag taatgaacaa gctgcagcga gcaaatccag acgacccagc ttatgatgaa    600
aacaagcgcc agtgtcaaga agatatcaag gtgatgaacg acctagtaga taaaattatt    660
gcagatcgca aagcaagggg tgaacaaagc gatgatttat taacgcagat gctaaacgga    720
aaagatccag aaacgggtga gccgcttgat gacgggaaca ttagctatca aattattaca    780
ttcttaattg cgggacacga aacaacaagt ggtcttttat catttgcgct gtatttctta    840
gtgaaaaatc cacatgtatt acaaaaagta gcagaagaag cagcacgagt tctagtagat    900
cctgttccaa gctacaaaca agtcaaacag cttaaaatatg tcggcatggt cttaaacgaa    960
gcgctgcgct tatggccaac tgctcctgcg ttttccctat atgcaaaaga agatacggtg   1020
cttggaggag aatatccttt agaaaaaggc gacgaagtaa tggttctgat tcctcagctt   1080
caccgtgata aaacaatttg gggagacgat gtggaggagt tccgtccaga gcgttttgaa   1140
aatccaagtg cgattccgca gcatgcgttt aaaccgtttg gaacggtca gcgtgcgtgt   1200
atcggtcagc agttcgctct tcatgaagca acgctggtac ttggtatgat gctaaaacac   1260
tttgactttg aagatcatac aaactacgag ctcgatatta agaaacttt aacgttaaaa   1320
cctgaaggct ttgtggtaaa agcaaaatcg aaaaaaattc cgcttggcgg tattccttca   1380
cctagcactg aacagtctgc taaaaaagta cgcaaaaagg cagaaaacgc tcataatacg   1440
ccgctgcttg tgctatacgg ttcaaatatg gaacagctg aaggaacggc gcgtgattta   1500
gcagatattg caatgagcaa aggatttgca ccgcaggtcg caacgcttga ttcacacgcc   1560
ggaaatcttc cgcgcgaagg agctgtatta attgtaacgg cgtcttataa cggtcatccg   1620
cctgataacg caaagcaatt tgtcgactgg ttagaccaag cgtctgctga tgaagtaaaa   1680
ggcgttcgct actccgtatt tggatgcggc gataaaaact gggctactac gtatcaaaaa   1740
gtgcctgctt ttatcgatga aacgcttgcc gctaaagggg cagaaaacat cgctgaccgc   1800
ggtgaagcag atgcaagcga cgactttgaa ggcacatatg aagaatggcg tgaacatatg   1860
tggagtgacg tagcagccta ctttaacctc gacattgaaa acagtgaaga taataaatct   1920
actctttcac ttcaatttgt cgacagcgcc gcggatatgc cgcttgcgaa aatgcacggt   1980
gcgttttcaa cgaacgtcgt agcaagcaaa gaacttcaac agccaggcag tgcacgaagc   2040
acgcgacatc ttgaaattga acttccaaaa gaagcttctt atcaagaagg agatcattta   2100
ggtgttattc ctcgcaacta tgaaggaata gtaaaccgtg taacagcaag gttcggccta   2160
```

-continued

```
gatgcatcac agcaaatccg tctggaagca gaagaagaaa aattagctca tttgccactc    2220
gctaaaacag tatccgtaga agagcttctg caatacgtgg agcttcaaga tcctgttacg    2280
cgcacgcagc ttcgcgcaat ggctgctaaa acggtctgcc cgccgcataa agtagagctt    2340
gaagccttgc ttgaaaagca agcctacaaa gaacaagtgc tggcaaaacg tttaacaatg    2400
cttgaactgc ttgaaaaata cccggcgtgt gaaatgaaat tcagcgaatt tatcgccctt    2460
ctgccaagca tacgcccgcg ctattactcg atttcttcat cacctcgtgt cgatgaaaaa    2520
caagcaagca tcacggtcag cgttgtctca ggagaagcgt ggagcggata tggagaatat    2580
aaaggaattg cgtcgaacta tcttgccgag ctgcaagaag gagatacgat tacgtgcttt    2640
atttccacac cgcagtcaga atttacgctg ccaaaagacc ctgaaacgcc gcttatcatg    2700
gtcggaccgg gaacaggcgt cgcgccgttt agaggctttg tgcaggcgcg caaacagcta    2760
aaagaacaag gacagtcact tggagaagca catttatact tcggctgccg ttcacctcat    2820
gaagactatc tgtatcaaga agagcttgaa aacgcccaaa gcgaaggcat cattacgctt    2880
cataccgctt tttctcgcat gccaaatcag ccgaaaacat acgttcagca cgtaatggaa    2940
caagacggca agaaattgat tgaacttctt gatcaaggag cgcacttcta tatttgcgga    3000
gacggaagcc aaatggcacc tgccgttgaa gcaacgctta tgaaaagcta tgctgacgtt    3060
caccaagtga gtgaagcaga cgctcgctta tggctgcagc agctagaaga aaaaggccga    3120
tacgcaaaag acgtgtgggc tggg                                           3144
```

<210> SEQ ID NO 54
<211> LENGTH: 1048
<212> TYPE: PRT
<213> ORGANISM: Bacillus megaterium

<400> SEQUENCE: 54

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Arg Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Ala Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Ile Ser
                165                 170                 175

Met Val Arg Ala Leu Asp Glu Val Met Asn Lys Leu Gln Arg Ala Asn
            180                 185                 190
```

-continued

```
Pro Asp Asp Pro Ala Tyr Asp Glu Asn Lys Arg Gln Cys Gln Glu Asp
        195                 200                 205

Ile Lys Val Met Asn Asp Leu Val Asp Lys Ile Ile Ala Asp Arg Lys
        210                 215                 220

Ala Arg Gly Glu Gln Ser Asp Leu Leu Thr Gln Met Leu Asn Gly
225                 230                 235                 240

Lys Asp Pro Glu Thr Gly Glu Pro Leu Asp Asp Gly Asn Ile Ser Tyr
                245                 250                 255

Gln Ile Ile Thr Phe Leu Ile Ala Gly His Glu Thr Thr Ser Gly Leu
        260                 265                 270

Leu Ser Phe Ala Leu Tyr Phe Leu Val Lys Asn Pro His Val Leu Gln
        275                 280                 285

Lys Val Ala Glu Glu Ala Ala Arg Val Leu Val Asp Pro Val Pro Ser
        290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
        340                 345                 350

Val Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
        370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
        420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
        500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
        580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
```

-continued

```
            610                 615                 620
Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                    645                 650                 655

Lys Met His Gly Ala Phe Ser Thr Asn Val Ala Ser Lys Glu Leu
                660                 665                 670

Gln Gln Pro Gly Ser Ala Arg Ser Thr Arg His Leu Glu Ile Glu Leu
                675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                    725                 730                 735

His Leu Pro Leu Ala Lys Thr Val Ser Val Glu Leu Leu Gln Tyr
                740                 745                 750

Val Glu Leu Gln Asp Pro Val Thr Arg Thr Gln Leu Arg Ala Met Ala
                755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
                835                 840                 845

Val Ser Gly Glu Ala Trp Ser Gly Tyr Gly Glu Tyr Lys Gly Ile Ala
                850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                    885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
                930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                    965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                 1000                1005

Val Glu Ala Thr Leu Met Lys Ser Tyr Ala Asp Val His Gln Val Ser
                1010                1015                1020

Glu Ala Asp Ala Arg Leu Trp Leu Gln Gln Leu Glu Glu Lys Gly Arg
1025                1030                1035                1040
```

Tyr Ala Lys Asp Val Trp Ala Gly
            1045

<210> SEQ ID NO 55
<211> LENGTH: 21
<212> TYPE: DNA
<213> ORGANISM: Artificial Sequence
<220> FEATURE:
<223> OTHER INFORMATION: Synthetic oligonucleotide primer sequence

<400> SEQUENCE: 55
ggaaacagga tccatcgatg c                                          21

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide primer sequence

<400> SEQUENCE: 56
gtgaaggaat accgccaagc                                            20

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide primer sequence

<400> SEQUENCE: 57
ggagacgggt tatttacaag c                                          21

<210> SEQ ID NO 58
<211> LENGTH: 33
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 24
<223> OTHER INFORMATION: n = A,T,C or G

<400> SEQUENCE: 58
gcttgtaaat aacccgtctc caanaaaatc acg                             33

<210> SEQ ID NO 59
<211> LENGTH: 22
<212> TYPE: DNA
<213> ORGANISM: Artificial Sequence
<220> FEATURE:
<223> OTHER INFORMATION: Synthetic oligonucleotide primer sequence

<400> SEQUENCE: 59
gcttatggcc aactgttcct gc                                         22

<210> SEQ ID NO 60
<211> LENGTH: 22
<212> TYPE: DNA
<213> ORGANISM: Artificial Sequence -continued

```
<220> FEATURE:
<223> OTHER INFORMATION: Synthetic oligonucleotide primer sequence

<400> SEQUENCE: 60
gcaggaacag ttggccataa gc                                              22
```